US007371423B2

(12) United States Patent
Søe et al.

(10) Patent No.: US 7,371,423 B2
(45) Date of Patent: *May 13, 2008

(54) METHOD FOR PREPARING FLOUR DOUGHS AND PRODUCTS MADE FROM SUCH DOUGHS USING LIPASE

(75) Inventors: Jorn Borch Søe, Mundelstrup (DK); Charlotte Horsmans Poulsen, Bradbrand (DK); Preben Rasmussen, Kirke Hyllinge (DK); Susan Mampusti Madrid, Vedboek (DK); Masoud R. Zargahi, Århus C. (DK)

(73) Assignee: Danisco, A/S, Copenhagen (DK)

( * ) Notice: Subject to any disclaimer, the term of this patent is extended or adjusted under 35 U.S.C. 154(b) by 891 days.

This patent is subject to a terminal disclaimer.

(21) Appl. No.: 10/462,527

(22) Filed: Jun. 16, 2003

(65) Prior Publication Data

US 2004/0071853 A1 Apr. 15, 2004

Related U.S. Application Data

(60) Continuation of application No. 10/040,394, filed on Jan. 9, 2002, now Pat. No. 6,852,346, which is a division of application No. 09/402,664, filed on Oct. 22, 1999, now Pat. No. 6,406,723.

(30) Foreign Application Priority Data

Apr. 9, 1997 (DK) ................................... 0400/97
Apr. 3, 1998 (WO) .................... PCT/DK98/00136

(51) Int. Cl.
A21D 10/00 (2006.01)
(52) U.S. Cl. .................... 426/549; 426/18; 426/20; 426/52; 426/653; 439/198
(58) Field of Classification Search ............... 426/18, 426/20, 52, 549, 563; 439/198
See application file for complete search history.

(56) References Cited

U.S. PATENT DOCUMENTS

| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melaschouris |
| 3,652,397 A | 3/1972 | Pardun |
| 3,677,902 A | 7/1972 | Aunstrup |
| 3,852,260 A | 12/1974 | Knutsen |
| 3,973,042 A | 8/1976 | Kosikowski et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada et al. |
| 4,399,218 A | 8/1983 | Gauhl et al. |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda et al. |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,677,160 A | 10/1997 | Oester |
| 5,695,802 A | 12/1997 | Van Den Ouweland |

(Continued)

FOREIGN PATENT DOCUMENTS

AR 249546 12/1996

(Continued)

OTHER PUBLICATIONS

*Lipase A "Amano" 6 Assay Note and Product Specificaiton*, from Amano Pharmaceutical Co., Ltd. Nagoya, Japan. Dated Aug. 27, 1985.

(Continued)

Primary Examiner—Keith Hendricks
Assistant Examiner—Vera Stulii
(74) Attorney, Agent, or Firm—Frommer Lawrence & Haug LLP; Thomas J. Kowalski; Angela M. Collison

(57) ABSTRACT

Method of improving the rheological properties of a flour dough and the quality of bread, alimentary paste products, noodles and cakes wherein glycerol oxidase or a combination of glycerol oxidase and a lipase is added to the dough and dough improving compositions comprising these enzymes. The strength of (B/C ratio) and the gluten index of the dough was improved and in the resulting products the improvements were higher specific volume, increased crumb pore homogeneity and reduced average crumb pore diameter.

15 Claims, 4 Drawing Sheets

U.S. PATENT DOCUMENTS

| | | | |
|---|---|---|---|
| 5,763,383 A | 6/1998 | Hashida | |
| 5,766,912 A | 6/1998 | Boel | |
| 5,776,741 A | 7/1998 | Pedersen | |
| 5,814,501 A | 9/1998 | Becker | |
| 5,821,102 A | 10/1998 | Berka | |
| 5,827,719 A | 10/1998 | Sandal | |
| 5,830,736 A | 11/1998 | Oxenboll | |
| 5,834,280 A | 11/1998 | Oxenboll | |
| 5,856,163 A | 1/1999 | Hashida | |
| 5,863,759 A | 1/1999 | Boel | |
| 5,869,438 A | 2/1999 | Svendsen | |
| 5,874,558 A | 2/1999 | Boel | |
| 5,879,920 A | 3/1999 | Dale | |
| 5,892,013 A | 4/1999 | Svendsen | |
| 5,914,306 A | 6/1999 | Svendsen | |
| 5,916,619 A | 6/1999 | Miyazaki | |
| 5,919,746 A | 7/1999 | Hirayama | |
| 5,929,017 A | 7/1999 | Gormsen | |
| 5,965,384 A | 10/1999 | Boel | |
| 5,965,422 A | 10/1999 | Loffler | |
| 5,976,855 A | 11/1999 | Svendsen | |
| 5,989,599 A | 11/1999 | Chmiel | |
| 5,990,069 A | 11/1999 | Andre | |
| 6,001,586 A | 12/1999 | Schellenberger | |
| 6,001,640 A | 12/1999 | Loeffler | |
| 6,020,180 A | 2/2000 | Svendsen | |
| 6,066,482 A | 5/2000 | Steffens | |
| 6,074,863 A | 6/2000 | Svendsen | |
| 6,103,505 A | 8/2000 | Clausen et al. | |
| 6,110,508 A | 8/2000 | Olesen | |
| 6,140,094 A | 10/2000 | Loffler | |
| 6,143,543 A | 11/2000 | Michelsen | |
| 6,143,545 A | 11/2000 | Clausen et al. | |
| 6,146,869 A | 11/2000 | Harris | |
| 6,156,548 A | 12/2000 | Christensen | |
| 6,180,406 B1 | 1/2001 | Stemmer | |
| 6,254,645 B1 | 7/2001 | Kellis | |
| 6,344,328 B1 | 2/2002 | Short | |
| 6,350,604 B1 | 2/2002 | Hirayama et al. | |
| 6,358,543 B1 | 3/2002 | Soe et al. | |
| 6,361,974 B1 | 3/2002 | Short | |
| 6,365,204 B1 | 4/2002 | Spendler | |
| 6,432,898 B1 | 8/2002 | Rey | |
| 6,495,357 B1 | 12/2002 | Fuglsang | |
| 6,506,588 B2 | 1/2003 | Tsutsumi | |
| 6,509,182 B2 | 1/2003 | Tsutsumi | |
| 6,511,837 B2 | 1/2003 | Tsutsumi | |
| 6,514,739 B1 | 2/2003 | Udagawa | |
| 6,558,715 B1 | 5/2003 | Rey | |
| 6,582,942 B1 | 6/2003 | Christensen | |
| 6,624,129 B1 | 9/2003 | Borch | |
| 6,645,749 B2 | 11/2003 | Vind | |
| 6,682,922 B2 | 1/2004 | Berka | |
| 6,686,189 B2 | 2/2004 | Rey | |
| 6,730,346 B2 | 5/2004 | Rey | |
| 6,815,190 B1 | 11/2004 | Abo et al. | |
| 6,852,346 B2 * | 2/2005 | Soe et al. | 426/18 |
| 2002/0098536 A1 | 7/2002 | Norinobu | |
| 2002/0110854 A1 | 8/2002 | Tsutsumi | |
| 2002/0142434 A1 | 10/2002 | Tsutsumi | |
| 2002/0168746 A1 | 11/2002 | Tsutsumi | |
| 2003/0003561 A1 | 1/2003 | Vind | |
| 2003/0028923 A1 | 2/2003 | Lardizabal | |
| 2003/0040450 A1 | 2/2003 | Rey | |
| 2003/0074695 A1 | 4/2003 | Farese | |
| 2003/0100092 A1 | 5/2003 | Berka | |
| 2003/0119164 A1 | 6/2003 | Udagawa | |
| 2003/0148495 A1 | 8/2003 | Hastrup | |
| 2003/0180418 A1 | 9/2003 | Rey | |
| 2003/0185939 A1 | 10/2003 | Nielsen | |
| 2003/0215544 A1 | 11/2003 | Nielsen | |
| 2004/0005399 A1 | 1/2004 | Chakrabarti | |
| 2004/0235106 A1 | 11/2004 | Kapeller-Libermann | |
| 2005/0059130 A1 | 3/2005 | Bojsen | |
| 2005/0059131 A1 | 3/2005 | Bisgard-Frantzen | |
| 2005/0118697 A1 | 6/2005 | Budolfsen | |
| 2005/0142647 A1 | 6/2005 | Wassell | |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CN | 97181706.5 | 12/1997 |
| DE | 28 17 087 | 11/1978 |
| DE | 2817087 | 11/1978 |
| DE | 19620649 | 11/1997 |
| DE | 69129988 | 3/1999 |
| DE | 69330066 | 10/2001 |
| DE | 69527835 | 4/2003 |
| DE | 69528070 | 6/2003 |
| DE | 69904161 | 7/2003 |
| DE | 69716711 | 9/2003 |
| DE | 69333065 | 4/2004 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA2000009991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0010296 | 4/1980 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0205208 | 12/1986 |
| EP | 0206390 | 12/1986 |
| EP | 0257388 | 3/1988 |
| EP | 0260573 | 3/1988 |
| EP | 0321811 | 6/1989 |
| EP | 0334462 | 9/1989 |
| EP | 0195311 | 6/1990 |
| EP | 0375102 | 6/1990 |
| EP | 0426211 | 5/1991 |

| | | | | | | |
|---|---|---|---|---|---|---|
| EP | 0468731 | 7/1991 | | EP | 1162889 | 2/2005 |
| EP | 0445692 | 9/1991 | | EP | 1559788 | 8/2005 |
| EP | 0449375 | 10/1991 | | EP | 1363506 | 11/2005 |
| EP | 0468731 | 1/1992 | | ES | 535608 | 9/1984 |
| EP | 0513709 | 11/1992 | | ES | 535602 | 10/1984 |
| EP | 0542351 | 5/1993 | | ES | 535609 | 3/1985 |
| EP | 0 585988 | 7/1993 | | GB | 1086550 | 10/1967 |
| EP | 0558112 | 9/1993 | | GB | 1442418 | 7/1976 |
| EP | 0258068 | 11/1993 | | GB | 1577933 | 10/1980 |
| EP | 0238023 | 12/1993 | | GB | 0028701.1 | 11/2000 |
| EP | 0575133 | 12/1993 | | GB | 2358784 | 8/2001 |
| EP | 0580252 | 1/1994 | | GB | 0301117.8 | 1/2003 |
| EP | 0 575 133 | 3/1994 | | GB | 0301118.6 | 1/2003 |
| EP | 0585988 A1 | 3/1994 | | GB | 0301119.4 | 1/2003 |
| EP | 0258068 | 8/1994 | | GB | 0301120.2 | 1/2003 |
| EP | 0622446 | 11/1994 | | GB | 0301121.0 | 1/2003 |
| EP | 0652289 | 5/1995 | | GB | 0301122.8 | 1/2003 |
| EP | 0654527 | 5/1995 | | GB | 2379165 | 3/2003 |
| EP | 0396162 | 9/1995 | | GB | 2267033 | 11/2003 |
| EP | 0585988 | 3/1996 | | GB | 0330016.7 | 12/2003 |
| EP | 0721981 | 7/1996 | | JP | 59183881 | 4/1960 |
| EP | 0 808 903 | 3/1997 | | JP | 55131340 | 10/1980 |
| EP | 0808903 | 3/1997 | | JP | 60078529 | 5/1985 |
| EP | 0776604 | 6/1997 | | JP | 62118883 | 11/1985 |
| EP | 0531104 | 8/1997 | | JP | 63042691 | 8/1986 |
| EP | 0808903 | 11/1997 | | JP | 62061590 | 3/1987 |
| EP | 0682116 | 12/1997 | | JP | 62118883 | 5/1987 |
| EP | 0812910 | 12/1997 | | JP | 62285749 | 12/1987 |
| EP | 0305216 | 3/1998 | | JP | 10203974 | 8/1988 |
| EP | 0847701 | 6/1998 | | JP | 1252294 | 10/1989 |
| EP | 548228 | 8/1998 | | JP | 2-49593 | 2/1990 |
| EP | 0548228 | 8/1998 | | JP | 2-153997 | 6/1990 |
| EP | 0702712 | 12/1998 | | JP | 04075592 | 3/1992 |
| EP | 0882797 | 12/1998 | | JP | 6014773 | 3/1992 |
| EP | 0897667 | 2/1999 | | JP | 4121186 | 4/1992 |
| EP | 0913092 | 5/1999 | | JP | 15626492 | 6/1992 |
| EP | 0913468 | 5/1999 | | JP | 04200339 | 7/1992 |
| EP | 0321811 | 12/1999 | | JP | 4300839 | 10/1992 |
| EP | 1131416 | 6/2000 | | JP | 4327536 | 11/1992 |
| EP | 0739985 | 11/2000 | | JP | 5211852 | 8/1993 |
| EP | 1057415 | 12/2000 | | JP | 6345800 | 12/1994 |
| EP | 1071734 | 1/2001 | | JP | 8268882 | 4/1995 |
| EP | 1073339 | 2/2001 | | JP | 7231788 | 9/1995 |
| EP | 0659049 | 3/2001 | | JP | 7330794 | 12/1995 |
| EP | 1103606 | 5/2001 | | JP | 8143457 | 6/1996 |
| EP | 1108360 | 6/2001 | | JP | 8266213 | 10/1996 |
| EP | 1138763 | 10/2001 | | JP | 9040689 | 2/1997 |
| EP | 1145637 | 10/2001 | | JP | 10155493 | 6/1998 |
| EP | 0191217 | 2/2002 | | JP | 10155493 A | 6/1998 |
| EP | 0869167 | 2/2002 | | JP | 11290078 | 10/1999 |
| EP | 1193314 | 4/2002 | | JP | 2000226335 | 8/2000 |
| EP | 0746618 | 8/2002 | | JP | 3553958 | 5/2004 |
| EP | 1233676 | 8/2002 | | KR | 93-700773 | 3/1993 |
| EP | 0648263 | 9/2002 | | KR | 94-10252 | 10/1994 |
| EP | 0784674 | 9/2002 | | KR | 95-700043 | 1/1995 |
| EP | 1275711 | 1/2003 | | KR | 95-702583 | 6/1995 |
| EP | 1285969 | 2/2003 | | KR | 96-704602 | 8/1996 |
| EP | 1298205 | 4/2003 | | KR | 2001-7012115 | 9/2001 |
| EP | 0635053 | 6/2003 | | KR | 2003-7008997 | 10/2003 |
| EP | 0675944 | 6/2003 | | NL | 0784674 | 12/2002 |
| EP | 0817838 | 6/2003 | | NL | 0869167 | 1/2003 |
| EP | 1280919 | 6/2003 | | NL | 1073339 | 2/2003 |
| EP | 0746608 | 8/2003 | | NL | 0746608 | 11/2003 |
| EP | 0851913 | 5/2004 | | RU | 2140751 | 6/1997 |
| EP | 1262562 | 6/2004 | | RU | 2235775 | 11/1999 |
| EP | 1433852 | 6/2004 | | RU | 2001117497 | 6/2001 |
| EP | 0977869 | 7/2004 | | TR | 200101551 | 12/1999 |
| EP | 0743017 | 9/2004 | | WO | 88/02775 | 4/1988 |
| EP | 0675949 | 10/2004 | | WO | 88/03365 | 5/1988 |
| EP | 0880590 | 10/2004 | | WO | 08/901969 | 3/1989 |
| EP | 0897423 | 10/2004 | | WO | 89/06803 | 7/1989 |
| EP | 1466980 | 10/2004 | | WO | 91/00920 | 1/1991 |
| EP | 0839186 | 11/2004 | | WO | 91/06661 | 5/1991 |

| | | |
|---|---|---|
| WO | 91/14772 | 10/1991 |
| WO | 92/05249 | 4/1992 |
| WO | 92/14830 | 9/1992 |
| WO | 92/18645 | 10/1992 |
| WO | 93/01285 | 1/1993 |
| WO | 93/11249 | 6/1993 |
| WO | WO 94/04035 | 6/1993 |
| WO | 93/12812 | 7/1993 |
| WO | 94/01541 | 1/1994 |
| WO | 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/11083 | 3/1997 |
| WO | 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | 98/08939 | 3/1998 |
| WO | 98/14594 | 4/1998 |
| WO | 98/18912 | 5/1998 |
| WO | 98/26057 | 6/1998 |
| WO | 98/31790 | 7/1998 |
| WO | 98/41623 | 9/1998 |
| WO | 98/44804 | 10/1998 |
| WO | 98/045453 | 10/1998 |
| WO | 98/45453 | 10/1998 |
| WO | 98/050532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | 00/28044 | 5/2000 |
| WO | 00/32758 | 6/2000 |
| WO | 00/34450 | 6/2000 |
| WO | 00/36114 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/61771 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | 01/34835 | 5/2001 |
| WO | 01/39602 | 6/2001 |
| WO | 01/42433 | 6/2001 |
| WO | 01/47363 | 7/2001 |
| WO | 01/66711 | 9/2001 |
| WO | 01/78524 | 10/2001 |
| WO | 01/83559 | 11/2001 |
| WO | 01/83770 | 11/2001 |
| WO | 01/92502 | 12/2001 |
| WO | 02/000852 | 1/2002 |
| WO | 02/003805 | 1/2002 |
| WO | 02/006457 | 1/2002 |
| WO | 02/014490 | 2/2002 |
| WO | 02/024881 | 3/2002 |
| WO | 02/030207 | 4/2002 |
| WO | 02/055679 | 7/2002 |
| WO | 02/062973 | 8/2002 |
| WO | 02/065854 | 8/2002 |
| WO | 02/066622 | 8/2002 |
| WO | 02/094123 | 11/2002 |
| WO | 2003/020923 | 3/2003 |
| WO | 03/040091 | 5/2003 |
| WO | 03/060112 | 7/2003 |
| WO | 03/070013 | 8/2003 |
| WO | 03/089260 | 10/2003 |
| WO | 03/097825 | 11/2003 |
| WO | 03/099016 | 12/2003 |
| WO | 03/102118 | 12/2003 |
| WO | 2003/100044 | 12/2003 |
| WO | 04/004467 | 1/2004 |
| WO | 2004/004467 | 1/2004 |
| WO | 2004/018660 | 3/2004 |
| WO | 04/053152 | 6/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | 04/097012 | 11/2004 |
| WO | 2004/111216 | 12/2004 |
| WO | 2005/003339 | 1/2005 |
| WO | 2005/005977 | 1/2005 |
| WO | 97/07205 | 2/2005 |
| WO | 2005/056782 | 6/2005 |
| WO | 2005/066347 | 7/2005 |
| WO | 2005/066351 | 7/2005 |
| WO | 2005/080540 | 9/2005 |
| WO | 2005/087918 | 9/2005 |
| WO | 2006/008508 | 1/2006 |
| WO | 2006/008653 | 1/2006 |
| WO | 2006/032279 | 3/2006 |

OTHER PUBLICATIONS

*Lipase AP "Amano", Amano Enzymes Technical Bulletin*, from Amano Pharmaceutical Co., Ltd. Nagoya, Japan dated Dec. 16, 1985.
*Lipase SP677 as a Baking Enzyme*, from Novo Nordisk Bagsvaerd Denmark, dated Mar. 17, 1994.
*Sales Range for Baking Improver and Premix Manufacturers*, from DSM Bakery Ingredients, Delft, The Netherlands.
J. Plijter and J.H. G.M. Mutsaers, *The surface rheological properties of dough and the influence of lipase on it*, Gist-brocades, Bakery Ingredients Division, Delft, The Netherlands, Oct. 1994.
*Food Enzymes*: Stalingase I., Gist-brocades Food Ingredients Division, Delft, The Netherlands.
*Product Description—PD 40084-7a Grindamyl Exel 16 Bakery Enzyme*, Danisco Specialties.
*Amano Enzymes*, Amano Enzyme Europe Ltd., Milton Keynes, United Kingdom, Sep. 1994.

Drost-Lustenberger, C. and Spendler, T. *Lipopan F BG—Application and Mechanism of a new lipase for baking*, Novozymes.

Sztajer, H. and Zboinska, E. *Microbial Lipases in Biotechnology*, Acta Biotechnol. 8 (1988) 2, 169-175.

Mohsen, S.M. et al., *Specificity of Lipase Produced by Rhyzopus Delemar and Its Utilization in Bread Making*, Egypt. J. Food Sci., 14(1):175-182 (1986).

Greenough, R.J. et al., *Safety Evaluation of a Lipase Expressed in Aspergillus oryzae*, Food and Chemical Toxicology, 34(2):161-66 (1996).

Rousseau, D. and Marangoni, A.G., *Tailoring the Textural Attributes of Butter Fat/Canola Oil Blends via Rhizopus arrhizue Lipase-Catalyzed Interesterification 2 Modification s of Physical Properties*, J. Agric. Food Chem. 46(6):2375-81 (1998).

U.S. Appl. No. 60/039,791, filed Mar. 4, 1997, Clausen et al.

Angelino, S.A.G.F., et al. ed. The Proceedings of the First European Symposium on Enzymes and Grain Processing. TNO Nutrition and Food Research Institute, Zeist, The Netherlands, 1997.

Marion D- Chapter 6, pp. 131-p. 167 of "Interactions The Keys to Cereal Quality" 1998 ISBN 0 913250-99-6 (ed. Hamer & Hosney).

Conference May 6-8, 1999 in Santorini, Greece—Lipases & Lipids Structures, Function and Biotechnological Applications—Slides presented by Charlotte Poulsen.

Marion D et al pp. 245-260 of Wheat Structure Biochemistry &Functionality (ed Schofield JP ) ISBN 085404777-8 published in 2000—(Proceedings of Conference organized by Royal Soc of Chemistry Food chemistry Group held on Apr. 10-12, 1995, in Reading, UK.).

T. Uwajima et al., Agricultrual and Biological Chemistry, 44(9), pp. 2039-2045, 1980, Properties of New Enzyme Glycerol Oxidase from *Aspergillus japomicus* AT 008.

T. Uwajima et al., Agricultural and Biological Chemistry, 43(12) pp. 2633-2634, 1979, "Some Characteristics of a New Enzyme Glycerol Oxidase".

T. Uwasjima et al, Methods in Enzymology, 89(41), pp. 243-248, "Glycerol Oxidase from *Asperigillus japonicus*".

Y. Mine, Food Research International, 29(1), 1996, pp. 81-84, "Application of the enzymatic methods to the determination of contaminated yolk in egg white".

K. Isobe et al., Journal of Molecular Catalysis B: Enzymatic 1 (1995), pp. 37-43, "A new enzymatice method for glycolaldehyde production from ethylene glycol".

S. Lin et al., Enzyme and Microbial Technology 18(1996), pp. 383-387, purification and characterization of a glycerol oxidase from *Pennicillium* sp. TS-622.

European Patent Office, Patent Abstracts of Japan, No. 06296467, Oct. 25, 1994.

European Patent Office, Patent Abstracts of Japan, No. 04200339, Jul. 21, 1992.

Abstract- XP 002077284, 12/61 (8/57 FSTA)- ( C) FSTA/IFIS, 1996.

Abstract- XP 002077285, 57/61 (53/57 FSTA) ( C) FSTA/IFIS, 1972.

Abstract- XP 002077286, 43/61 (39/57 FSTA) ( C) FSTA/IFIS, 1979.

Abstract- XP002077286, 43/61 (39/57 FSTA) ( C) FSTA/IFIS, 1979.

Abstract- XP 002077295 1/2 ( C) FSTA/IFIS, 1996.

Abstract- XP002077295 1/2 ( C) FSTA/IFIS, 1996.

DIRECT: A Newsletter from Danisco Ingredients. Issue #1. Sep. 1996. "Unique Chance for Better Bread.".

Colombo, et al. Optically Pure 1-O and 3-O-β-D-Glucosyl and Galactosyl -sn-glycerols through Lipase-Catalyzed Transformations (1995), Tetrahedron Letters, vol. 36 (27): 4865-4868.

Bilyk, et al. Lipase-Catalyzed Triglycerides Hydrolysis in Organic Solvent (1991), Journal of the American Oil Chemists Society, vol. 68 (5): 320-323.

Tsuchiya, et al. Cloning and nucleotide sequence of the mono-and diaglycerol lipase (mdlB) of *Aspergillus oryzae* (1996) FEMS Microbiology Letters vol. 143: 63-67.

Mase, et al. Purification and Characterization of a New Lipase from *Fusarium* sp. YM-30 (1995), Bioscience, Biotech, Biochemistry, vol. 59 (9): 1771-1772.

Martinez, et al. A pancreatic lipase with a phospholipase A1 activity (1996), Structure, vol. 4: 1363-1374.

Carriere, et al. Structural basis for the substrate selectivity of pancreatic lipases and some related proteins (1998), Biochimica et Biophysica Acta, vol. 1376: 417-432.

Gemel, et al. Comparison of galactolipase activity and free fatty acid levels in chloroplasts of chill-sensitive and chill-resistant plants (1987), Eur. J. Biochem., vol. 166: 229-233.

Matsuda, et al. Purification and Properties of a Lipolytic ACYL-Hydrolase from Potato Leaves (1979) Biochimica et Biophysica Acta, vol. 573: 155-165.

Strickland, et al. Inhibition of Diabrotica Larval Growth by Patatin, the Lipid Acyl Hydrolase from Potato Tubers (1995) Plant Physiol. vol. 109: 667-674.

Matos, et al. A patatin-like protein with galactolipase activity is induced by drought stress in *Vigna unguiculata* leaves (2000) Biochemical Society, vol. 28(6): 779-781.

Jacob, et al. The Effects of Galactolipid Depletion on the Structure of a Photosynthetic Membrane (1986) Journal of Cell Biology, vol. 103: 1337-1347.

Murakami, et al. Enzymatic Transformation of Glyceroglycolipids into sn-1 and sn-2 (1994) Tetrahedran vol. 50(7): 1993-2002.

Luzi, et al. Structure and Organization of the Human Galactocerebrosidase (GALC) Gene (1995) Genomics, vol. 26: 407-409.

Andersson, et al. Hydrolisis of galactolipids by human pancreatic lipolytic enzymes and duodenal contents (1995) Journal of Lipid Research, vol. 36: 1392-1400.

Sakai, et al. Human galactocerebrosidase gene: promoter analysis of the 5' flanking region and structural organization (1998) Biochimica et Biophysics Acta, vol. 1395: 62-67.

Collar, et al. Lipid Binding of Fresh and Stored Formulated Wheat Breads (2001) Food Sci Tech Int., vol. 7(6): 501-510.

Sahsah, et al. Enzymatic degradation of polar lipids in *Vigna unguiculata* leaves and influence of drought stress (1998) Physiol. Plantarum, vol. 104: 577-586.

Larsen, et al. The Effect of Ball-milling on Phospholipid Extractability and the Breadmaking Quality of Flour (1990) Journal of Science, vol. 12: 155-164.

Chung, et al. Defatted and Reconstituted Wheat Flours (1979) Cereal Chem, vol. 57(2): 111-117.

Ponte, et al. Note on the Separation and Baking Properties of Polar and Nonpolar Wheat Flour Lipids (1968) Wheat Flour Lipids: Properties, vol. 46: 325-329.

Ostrovskaya, et al. Spectral Features of the Action of Galactolipase on Native Forms of Chlorophyl (1969) Institute of Plant Physiology.

Kochubel, et al. Role of lipids in the organization of the closest surroundings of the reaction centers (1976) Institute of Plant Physiology.

Kochubei, et al Differences in the Structure of Long Wave Flourescence Molecular Aggregates in Photosystems (1975) Molekulyarnaya Biologiya, vol. 9(2): 190-193.

Sahsah, et al. Purification and characterization of a soluble lipolytic acylhydrolase from Cowpea (1994) Biochimica et Biophysics Acta, vol. 1215: 66-73.

Hirayama, et al Purification and properties of a lipid acyl-hydrolase from potato tubers (1975) Biochimica et Biophysica Acta, vol. 384: 127-137.

Sakaki, et al. Purification and Immunological Properties of Galactolipase from *Phaseolus vulgaris* Leaves (2003) Advance Research on Plant Lipids, p. 291-290.

Duan Enzymatic Aspects of Fat Digestion in the Gastrointestinal Tract.

Kim, et al. Thermal Inactivation Kinetics and Application of Phospho-and Galactolipid-Degrading Enzymes for Evaluation of Quality Changes in Frozen Vegetables (2001) Journal of Agriculture Food Chem., vol. 49: 2241-2248.

Michalski, et al. Photosynthetic Apparatus in Chilling Sensitive Plants (1980) Biochimica et Biophysics Acta, vol. 589: 84-99.

Helmsing Purification and Properties of Galactolipase (1969) Biochimica et Biophysics Acta, vol. 178: 519-533.

Krupa, et al. Requirement of Galactolipids for Photosystem 1 Activity in Lyophilized Spinach Chloroplasts (1975) Biochimica et Biophysics Acta, vol. 408: 26-34.

Sias, et al. Human Pancreatic Lipase Related Proterin 2 Is a Galactolipase (2004) Biochemistry, vol. 43: 10138-10148.

Terasaki, et al. Glycerolipid Acyl Hydrolaise Activity in the Brown Alga *Cladosiphon okamuranus* Tokida (2003) Biosci. Biotechnol. Biochem., vol. 67(9): 1986-1989.

Kaniuga Galactolipase and chilling sensitivity of plants (1997) Acta Biochimica Polonica, vol. 44 (1) : 21-36.

Kochubei, et al. Nature of Longwave Fluorescence of Particles Enriched with Photosystem I (1981) Biophysics, vol. 26(2); 299-304.

Ohm, et al. Relationships of Free Lipids with Quality Factors in Hard Winter Wheat Flours (2002) Cereal Chemistry, vol. 79(2): 274-278.

Nierle, et al. Weizenlipide (1981) Jahrgang, vol. 10: 391-395.

Lin, et al. Hard Red Spring and Durum Wheat Polar Lipids (1974) Wheat Polar Lipids, vol. 51: 34-45.

Acker, L. "Die Lipide des Getreides, ihre Zusammense und inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994.

Adhikari, B., et al., "Stickiness in Foods: A Review of Mechanisms and Test Methods", International Journal of Food Properties, vol. 4, No. 1, 2001.

Agarwal et al., "Lipase Activity of Some Fungi Isolated from Groundnut", Current Science, Dec. 5, 1984, vol. 53, No. 23.

Aires-Barros et al (1994) Isolation and purification of lipases, Cambridge Unversity Press.

Aisaka, Kazuo et al., "Production of Lipoprotein Lipase and Lipase by *Rhizopus japonicu*", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, Dissertation Abstracts International B (1987) vol. 47(9) 3597, order No. DA8624641, pp. 266.

Amano Enzyme Inc. (2004). Http://www.amano-enzyme.co.jp/english/productuse/oil_fat.html. Dato June 21, 2004.

Amano Enzymes "Enzymes for Gastrointestinal Digestion" Oct. 1997.

Amano Enzymes, Amano Enzyme Europe Ltd, Sep. 1994.

Amin, Neelam S., et al., "Direct transformation of site-saturation libraries in *Bacillus subtilis*", BioTechniques, Dec. 2003, 35:1134-1140.

Amino acid composition of lipases, no date.

Andersson, L., et al., "Hydrolysis of galactolipids by human pancreatic lipolytic enzymes and duidenal contents", Journal of Lipid Research, 1995, vol. 36, pp. 1392-1400.

Andreas Sander, Eberhand Eilers, Andrea Heilemann, Edith von Kreis.Fett/lipid 99 (1997) Nr. 4, 115-120.

Angelino, S.A.G.F., et al., "The first European Symposium on Enzymes and Grain Processing" Apr. 9, 1997.

An-I Yeh et al., "Effects of Oxido-reductants on rheological properties of wheat flour dough and comparison with some characteristics of extruded noodles", Cereal Chemistry, 1999, vol. 76, No. 5, pp. 614-620.

Application of F. oxysporum phospholipase (FoL) in baking, no date.

Arbige, Michael A et al, Novel lipase for cheddar cheese flavor development, no date.

Archer, David B., et al., "Proteolytic degradation of heterologous proteins expressed in *Aspergillus niger*", Biotechnology Letter, vol. 14, No. 5, May 1992, pp. 357-362.

Arcos J.A. et al, "Quantative Enzymatic Production of 6.O-Acylglucose Esters", Biotechnology and Bioengineering 1998 57(5).

Arpigny Jean Louis et al, "Bacterial lipolytic enzymes: Classification and properties", Biochemical Journal, vol. 343, No. 1, Oct. 1, 1999, pp. 177-183, XP002375631.

Assignment Document for Enzymatisk detergent additiv, detergent og vaskemetode, no date.

Atomi, et al.; "Microbial Lipases—from Screening to Design"; pp. 49-51, no date.

August C.A.P.A. et al. "The use of genetic engineering to obtain efficient production of porcine pancreatic phospholipase A2", Biochimica et Biophysica Acta, vol. 1089, 1991, pp. 345-351.

Aunstrup, Knud et al., "Production of Microbiol Enzymes", Microbiol Technology, vol. 1, no date.

Ausubel, Frederick M., et al., "Short Protocols in Molecular Biology- A Compendium of Methods from Current Protocols in Molecular Biology", 1995, John Wiley & Sons, Inc.

Bachmatova, I., et al., "Lipase of *Pseudomonas mendocina* 3121-1 and its Substrate Specificty", Biologija, 1995.

Bailey's Industrial Oils and Fat Products, vol. 2, 4th Edition, John Wiley and Sons, New York pp. 97-173, no date.

Bakezyme PH 800, no date.

Balashev, Konstantin, Surface studies of enzymes using Atomic force microscopy (AFM), no date.

Balcao V.M., Pavia A.L. Malcata F.X., Enzyme Microb Technhol, May 1, 1996; 18(6):392-416.

Balcao, Victor M and Malcata F. Xavier (1998), Biotechnology Advances, vol. 16, No. 2, pp. 309-341, no date.

Ballance, D.J., et al., "Transformation of *Aspergillus nidulans* by the orotidine-5'-phosphate decarboxylase gene of neurospora crassa", Biochemical and biophysical Research Communications, vol. 112, No. 1, 1983, pp. 284-289.

Ballance, Molecular Industrial Mycology, Systems and Applications for Filamentous Fungi, Leong and Berka (eds.), Marcel Dekker Inc, New York 1991, pp. 1-29.

Barbesgaard, Peder et al Applied Microbiology and Biotechnology (1992) 36: 569-572.

Barnes, P.J., "Lipids in Cereal Technology", Food and Science Technology, Academic Press, 1983.

Basrl, M., et al., "Amidination of Lipase with Hyrdophobic Imidoesters", JAOCS, vol. 69, No. 6, Jun. 1992.

Bateman A and Haft DH (2002) Brief Bioinform 3, 236-245.

Boel, Esper, et al.; "Rhizomucor miehei Triglyceride Lipase is Synthesized as a Precursor"; Novo Research Institute; vol. 23; No. 7; Jul. 1988.

Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brady, Leo, et al., "A serine protease triad forms the catalytic centre of a triacylglycerol lipase", Nature, vol. 343, 1990.

Brockerhoff, Hans, et al., "Lipolytic Enzymes", Academic Press, 1974.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor comples", Nature, vol. 351, 1991.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155.

Bulletin of the IDF 294: 1994.

Burdge, Graham C., et al., "A method for separation of phosphatidycholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Cao, Shu-Gui, et al., "Enzymatic Preparation of Monoglycerides via Glycerolysis of Fats and Oils Catalyzed by Lipase from *Pseudomonas* Species" National Laboratory of Enzyme Engineering.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, P., et al., "Technological and Biochemical effects of exogenous lipases in breadmaking", 2nd European Symposium on enzymes in Grain Processing.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4, pp. 476-482.

Chakravarti DN et al, Biol. Abstracts, 1981, vol. 72, abstract No. 012592.

Cheng Cheng et al., "Transformation of *Trichoderma viride* using the *Neurospora crassa* pyr4 gene and its use in the expression of a Taka-amylase A gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of *Pseudomonas cepacia* Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science And Technology, vol. 103, 2001, pp. 333-340.

Clausen, Kim, "New enzyme for degumming", Oils and Fats International, vol. 17, No. 4, Jun. 2001, pp. 24-25.

Cloning of rad51 and rad52 homologues from *Aspergillus oryzae* and the effect of their overexpression on homologous recombination.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-O-β-D-Glucosylk- and Galactosyl-sn-glycerols through Lipase-catalyzed Transformations", Tetrahedron Letters, vol. 36, No. 27, pp. 2865-4868, 1995.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).

Council Regulation (EC) No. 2291/94 May 12, 1994 Official Journal of the European Communities, Sep. 12, 1994, No. L316/2-7.

Courtin, Christophe M., et al., "Recent Advances in Enzymes in Grain Processing".

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, Heterologous expression of the *Aspergillus nidulans* regulatory gene nirA in *Fusarium oxysporum*, (1991) Gene 109(1), 155-60.

Daboussi et al., "Transformation of seven species of filamentous fungi using the nitrate reductase gene of *Aspergillus nidulans*", Curr. Genet., 15:453-456, 1989.

Daftary, R.D., et al., "Functional Bread-Making Properties of Wheat Flour Lipids", Food Technology, vol. 22, No. 237, Mar. 1968-1979.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Danisco, Hexose oxidase—nyt enzym med mange mulingheder (advert).

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Database accession No. P10480 -& Database UniProt 'Online!, Jul. 1, 1989.

Database accession No. Q44268 -& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database UniprotKB Jun. 1, 2003, S. Omura et al: "putative secreted hydrolase from streptomyces avermitilis" XP002376340 retrieved from Ebi, Hinxton, UK Database accession No. Q828T4 abstract.

Database UniprotKB May 1, 2000, S.D. Bentley et al: "Putative Secreted Hydrolase from *Streptomyces coelicolor*" XP002376339 retrieved from Ebi, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.
Declaration by Clive Graham Phipps Walter (Dec C).
Declaration by Dr Jorn Borch Soe (Dec F).
Declaration by Dr M Turner.
Declaration by Dr Mark Turner (Dec G).
Declaration by Henrik Pedersen (Dec A).
Declaration by Henrik Pedersen, Masoud Rajabi Zargahi and Clive Graham Phipps Walter (Dec 2).
Declaration by Janne Brunstedt (Dec D).
Declaration by Kazuko Kato, Henrik Pedersen, Masoud Rajabi Zaghari, Clive Phipps Walter, and Janne Brunstedt (Dec I).
Declaration by Kim Borch.
Declaration by Luise Erlandsen.
Declaration by Masoud Rajabi Zargahi (Dec B).
Declaration by Masoud Rajabi Zargahi (Dec E).
Declaration by Tina Spendler.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the *Rhizomuxor miehei* Triacylglyceride Lipase at 1-9 Å Resolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Dictionary of Biochemistry and Molecular Biology, Second Edition, p. 16.
Dinkci. N, Mucor miehei den elde edilen lipaz.
Direct, A Newsletter from Danisco Ingredients, Sep. 1996.
Directive 2000/36/EC. Http://europa.eu.int/scadplus/leg/en/lvb/121122b.htm. Dato: Jun. 16, 2004.
Drost-Lustenberger, C and Spendler T Lipopan F BG—Application and Mechanism of a new lipase for baking, Novozymes.
Drost-Lustenberger, Cornelia, et al., "Lipopan F BG-application and mechanism of a new lipase for bread baking", Cereal Food, 2003.
Drost-Lustenberger, Cornelia, et al., "Lipopan F BG-unlocking the natural strengthening potential in dough", Cereal Food, 2004.
Duan, Rui Dong, Fat Digestion and Absorption (2000), p. 25-46, publisher AOCS Press, Champaign III Coden 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.
Dugi KA et al., "Human hepatic and lipoprotein lipase: the loop covering the catalytic site mediates lipase substrate specificity", Journal of Biological Chemistry (1995), vol. 270, pp. 25, 396-pp. 25, 401.
Dugruix (Edited by) Crystallization of Nucleic Acids and Proteins A Practical Approach.
Dutilh & Groger, "Improvement of Product Attributes of Mayonnaise by Enzymatic Hydrolysis of Egg Yolk with Phospholipase A2", 1981 J. Sci. Food Agric. 32, 451-458.
Dybdal, L., et al., "Enzymes in Cereals Processing".
Eddine et al, "Cloning and expression analysis of NhL1, a gene encoding an extracellular lipase from the fungal pea pathogen *Nextria haematococca* MP VI (*Fusarium solani f.* sp. pisi) that is expressed in planta", Mol. Genet. Genomics (2001) 265: 215-224.
EFEMA Index of Food Emulsifiers Jan. 2004, 4th Edition.
Efthymiou CC et al. Development of domestic feta cheese.
Eliasson et al., "Cereals in Breadmaking- A molecular colloidal approach".
Ellaiah et al., "Production of lipase by immobilized cells of *Aspergillus niger*", Process Biochemistry, vol. 39, 2004, pp. 525-528.

Elyk, Alexander, et al., "Lipase-Catalyzed—", JAOCS, vol. 08, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fennema, Owen F., "Food Chemistry Second Edition, Revised and Expanded".
Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, J. Chem. Technol. Biotechnol. 75, 569-576.
Finizym Technical Information, Novo Enzymes, 1981.
Fødevarenubusteriet (2003). Bekendtgørelse om indhold af transfedtsyrer I olier og fedtstoffer. Bekendtgørelse nr. 160 af Nov. 3, 2003.
Food Enzymes: Stalingase L, Gist-brocades Food Ingredients.
Food R&D. Dairy fields ingredient technology section.
Forman, Todd, "Enzymes Used in Bread Baking: An Application Update", Technical Bulletin, vol. XXVI, Issue 10, Oct. 2004.
Fox, et al.; "Isolation and some Properties of Extracellular Heat-Stable Lipases: from *Pseudomonas fluorescens* Strain AFT 36"; Journal of Dairy Research (1988); vol. 50; pp. 77-89.
Frenken N. et al (1992) Appl. Envir. Microbiol. 58 3787-3791.
Freshzyme, Product Sheet.
Frohman, et al.;"Rapid Production of Full-Length cDNAs from Rare transcripts: Amplification using a single gene-specific oligonucleotide primer"; Proc. Natl. Acad. Sci. USA(1988); vol. 85; pp. 8998-9002.
Frost & Sullivan, U.S. Market for Enzymes for food Applications.
Fugman, Douglas A et al Biochemica et Biophysica acia 795 (1984) 191-195.
Functional Bread-Making Properties of Lipids.
Galliard T and Dennis S (1974) Phytochemistry vol. 13, pp. 1731-1735.
Galliard, "The Enzymic Breakdown of Lipids in Potato Tuber by Phospholipid- And Galactolipid- Acyl Hydrolase Activities and by Lipoxygenase", Phytochemistry, 1970, vol. 9, pp. 1725-1734.
Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Geus et al (1987) Nucleic Acids Research 15(9) p. 3743-3759.
Gilbert, E. Jane, et al., "Purification and properties of extracellular lipase from *Pseudomonal aeruginosa* EF2", Journal of General Microbiology, 1991, vol. 137, pp. 2223-2229.
Gillian, B., Turgeon et al., "Cochliobolus heterostrophus using the *Aspergillus nidulans* amdS gene", Mol Gen Genet, 201: 450-453, 1985.
Gist-brocades, Amylase P Information Sheet.
Godfrey, Tony, et al., "Industrial Enzymology Second Edition".
Goodey et al, Yeast Biotechnology, Berry et al (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase® and Lipopan™ F.
Greenough et al (1996) Food Chem Toxicology 34:161-166 and PubMed abstract in respect thereof.
Greenough R J et al, Food and Chemical Toxicology, vol. 34(2), 1996, pp. 161-166.
Grinsted Products, Grinsted Bakery News.
Grinsted, "Emulsifiers for the baking industry".
Grinsted, "Grindamyl Fungal Alpha-Amylase".
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus* and *Rhizomucor*. Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hamer, Rob J., et al., "Interaction: The Keys to Cereal Quality", American Association of Cereal.
Hanlin, Richard T., "Illustrated Genera of Ascomycetes"; The American Phytopathological Society.
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the *Neurospora crassa* nit-4 pathway-specific regulartory gene for nitrate assimilation in *Aspergillus nidulans*", Gene., vol. 100, pp. 237-240, 1991.
Hedin, Eva M.K., et al., "Selective reduction and chemical modification of oxidized lipase cysteine mutants".
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. Jan. 15, 1991; 266(2): 997-1000.
Hirayama O et al, Biochim Biophys Acta. 1975, vol. 384(1), p. 127-37.
Hirose, Yoshihiko et al., "Characteristics of Immobilized Lipase PS on Chemically Modified Ceramics", Amano Pharmaceutical.
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.
Holmquist et al., "Lipases from *Rhizomucor miehei* and *Humicola lanuginosa*: Modification of the Lid covering the active site alters enantioselectivity", Journal of Protein Chemistry, vol. 12, No. 6, 1993.
Holmquist et al., "Probing a Functional Role of Glu87 and Trp89 in the Lid of *Humicola lanuginosa* Lipase through Transesterification Reactions in Organic Solvent", Journal of Protein Chemistry, 1995, vol. 14, No. 4, pp. 217-224.
Holmquist et al., "Trp89 in the Lid of *Humicola lanuginosa* Lipase is Important for Efficient Hydrolysis of Tributyrin", Lipids, vol. 29, No. 9, 1994.
Horn T et al, (1980) Nuc Acids Res Symp Ser 225-232.
Hoshino, et al.; "Calcium Ion Regulates the Release of Lipase of *Fusarium oxysporum*"; J. Biochem (1991); vol. 110; pp. 457-461.
Hoshino, et al.; "Purification and Some Characteristics of Extracellular Lipase from *Fusarium oxysporum f.* sp. *lini*"; Biosci. Biotech. Biochem (1992); pp. 660-664.
Hoshino, Tamotsu, et al., "Purification and Some Characteristics of Extracellular Lipase from *Fusarium oxysporum*", Biosci. Biotech. Biochem., vol. 56, No. 4, pp. 660-664, 1992.
Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "*Rhizomucor miehei* Triglyceride Lipase is Processed and Secreted from Transformed *Aspergillus oryzae*", Lipids, vol. 24, No. 9, pp. 1989.
Humum et al., "Enzyme Catalysed Synthesis in Ambient Temperature Ionic Liquids", Biocatalysis and Biotransformation, vol. 19, pp. 331-338.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzymology (2nd Ed.), The Macmillan press 1996.
Ishihara et al Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Iwai, Mieko, et al., "Hydrolytic and Esterifying Actions of Crystalline Lipase of *Aspergillus niger*", Osaka Municipal Technical Research Institute, Osaka, Japan.
Izco et al. Adv Food Sci vol. 21 N 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53:609-616.
jan-Willem F. A. Simons et al., "Cloning, purification and characterisation of the lipase from *Staphylococcus epidermidis*", Eur. J. Biochem., vol. 253, pp. 675-683, 1998.
Jeng-yen Lin, Matthew, "Wheat Polar Lipids- A Theseis Submitted to the Graduate Faculty of the North Dakota State University of Agriculture and Applied Science", May 1972.
Jensen B et al "Effect and Activity of Lipases in Dough and Bread" Translation.
Jensen, B., et al., "Effekt and Wirksamkeit von Lipasen in Teig und Brot".
JJ Owens. Lecithinase Positive Bacteria in milk.
Joerger et al., "Alteration of Chain Length Selectivity of a *Rhizopus delemar* Lipase through Site-Directed Mutagenesis", Lipids, vol. 29, No. 6, 1994, pp. 377-384.
Jong et al.; "American Type Culture Collection Catalogue of Filamentous FUNGI"; Eighteenth edition (1991).

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from *Fusarium oxysporum*", Department of Chemistry, Indian Institute of Technology, vol. 25, No. 1 & 2, pp. 76-78.

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.

Kaniuga Z, Acta Biochim Pol. (1997), vol. 44(1), p. 21-35.

Kapur J & Sood ML, J. Parasit., 1986, vol. 72, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kasai, Naoya, et al., "Optically Active Chlorohydrins as Chiral C3 and C4 Building Units: Microbial Resolution and Synthetic Applications", Chirality, vol. 10, pp. 682-692.

Kawamura and Doi, J. of Bacteriology Oct. 1984, p. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al. Korean J Dairy Sci 15 (2): 103-117 1993.

Kim, Hyung Kwoun, et al., Expression and characterization of Ca2+-independent lipase from *Bacillus pumilus* B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, pp. 107-112.

Kindstedt et al, Rapid Quantative test for free oil (Oiling off) in melted Mozzarella cheese.

King et al, Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of *Rhizopus delemar* Lipase Through Mutagenesis and Molecular Modeling", Lipids, 1997, vol. 32, No. 2, pp. 123-130.

Klein, Robert R., et al., "Additive Effects of Acyl-Binding Site Mutations on the Fatty Acid Selectivity of *Rhizopus delemar* Lipase", JAOCS, vol. 74, No. 11, 1997.

Kocak et al, Effect of lipase enzyme (palatase A 750 L) on the ripening of tulum cheese.

Kocak et al, Milchwissenschaft 51(1), 1996.

Kochubei et al Role of lipids in the organization of the closest surroundings of the reaction centers(1976) Institute of Plant Physiology.

Kochubei S M et al, Biophysics (1981), vol. 26(2), p. 299-304.

Kochubei S M et al, Mol Biol (Mosk) (1975), vol. 9(2), (p. 190-3) p. 150-153.

Kochubei SM et al, Mol Biol (Mosk) (1978),(vol. 1, p. 47-54) p. 32-37.

Kolkovski et al (1991) Fish Nutrition in Practice, Biarritz (France), Jun. 24-27.

Kostal, Jan, et al., "Enhanced Arsenic Accumulation in Engineered Bacterial Cells Expressing ArsR", Applied and Environmental Microbiology, Aug. 2004, pp. 4582-4587.

Kouker, et al.; "Specific and Sensitive Plate Assay for Bacterial Lipases"; Applied and Environmental Microbiology (1987); vol. 53 (1); pp. 211-213.

Krishna, Sajja Hari, et al., "Enantioselective transesterification of a tertiary alcohol by lipase A from *Candida antarctica*", Tetrahedron: Asymmetry, vol. 13, 2002, pp. 2693-2696.

Kristensen A.C.J. (2004) Preparation of margarine and spreads by enzyme-generated emulsifiers. Master thesis, The Royal Veterinary and Agricultural University, Frederiksberg, Copenhagen.

Krog, Cereal Foods World, The American Association of Cereal Chemists, p. 10, Jan. 1979, vol. 24, No. 1, pp. 10-11.

Krupa, Zbigniew et al., "Requirement of Galactolipids for Photosystem J Activity In Lyophilized Spinach Chloroplasts", Biochimica et Biophysica Acta, 408, pp. 26-34, 1975.

KSV-5000.

Kuipers, Oscar P., et al., "Enhanced Activity and Altered Specificity of Phospholipase A2 by Deletion of a Surface Loop", Science, vol. 244, 1989.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, 1994.

Larchenkova LP et al. Effect of starter and souring temperature on reproduction of *E coli* and *lactobacili* in milk.

Larsen N G et al, Journal of Cereal Science (1990), vol. 12 (2), p. 155-164.

Lecointe et al Biotechnology Letters, vol. 18, No. 8 (August) pp. 869-874.

Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.

Lee, Kyung S., et al., The *Saccharomyces cerevisiae* PLB1 Gene Encodes a Protein Required for Lysophospholipase and Phospholipase B Activity, The Journal of Biological Chemistry, vol. 269, No. 31, Issue of Aug. 5, pp. 19725-19730.

Leggio, Leila Lo, et al., "The 1.62 A structure of *Thermoascus aurantiacus* endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of *Candida albicans*", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p. 34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Lipomod L338P.

Lipopan F: Keep the quality—cut your costs 2000 Novozymes A/S. www.enzymes.novo.dk/cgl-bin/bvisapi.dll/biotimes/one_article.jsp?id=16947&lang=en&t=b1.

Litthauer, Derek, et al., "*Pseudomonas luteola* lipase: A new member of the 320- residue *Pseudomonas lipase* family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Lo Y-C et al. Crystal structure of *Escherichia coli* Thioesterase I/ProteaseI/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.

Lozano et al., "Over-stabilization of *Candida antarctica* lipase B by ionic liquids in ester synthesis", Biotechnology Letters, vol. 23, pp. 1529-1533, 2001.

Lustenberger Abstract.

Luzi, Paola et al, Genomics (1995), vol. 26(2), p. 407-9.

Madsen J.S. & Qvist K.B. (1997) J. Food Sci. 62, 579-582.

Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions The Keys to Cereal Quality" 1998 ISBN 0 913250-99-6 (ed. Hamer & Hoseney).

Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of *Humicola lanuginosa* lipase", Protein Engineering, vol. 9, No. 6, 1996, pp. 519-524.

Martinez, Chrislaine, et al., "Engineering cysteine mutants to obtain crystallographic phases with a cutinase from *Fusarium solani* pisi", Protein Engineering, vol. 6, No. 2, pp. 157-165, 1993.

Martinez, Diego, et al., "Genome sequence of the lignocellulose degrading fungus *Phanerochaete chrysosporium* strain RP78", Nature Biology, May 2, 2004.

Mase et al., "Purification and Characterization of a new Lipase from Fusarium sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of *Penicillium notatum* phospholipase B deduced from the Cdna", Eur. J. Biochem., vol. 202, pp. 783-787, 1991.

Matos AR, Lipid Catabolism: Lipid Degradation, 2000, p. 779-781.

Matos, A.R., et al., "A patatin-like protein with galactolipase activity is induced by drought stress in *Vigna unguiculata* leaves", Biochemical Society Transactions, vol. 28, part 6, 2000.

Matos, AR et al, Febs Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus saitor*"; Biotiechonology and Applied Biochemistry (1987); vol. 9, pp. 401-409.

Matthes et al, (1984) EMBO J. 3, p. 801-805.

Max-Planck-Institut fur Kohlenforschung et al., "Controlling the enantioselectivity of enzymes by directed evolution: Practical and theoretical ramifications".

McAuley, Katherine E., et al., "Structure of a feruloyl esterase from *Aspergillus niger*", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "Further Improvements in the Yield of Monoglycerides During Enzymatic Glycerolysis of Fats and Oils".

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

McNeill, Gerald P., et al., "Solid Phase Enzymatic Glycerolysis of Beef Tallow Resulting in a High Yield of Monoglyceride".

Mechanism studies of the new lipase, Article, p. 1, No. 14.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in *Aspergillus giganteus*", Mol Genet Genomics, 2002, vol. 266, pp. 747-757.

Meyers, Robert A., "Molecular Biology and Biotechnology—A Comprehensive Desk Reference".

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al. "Covalent immobilisation of manganese peroxidases (MnP) from *Phanerochaete chrysosporium* and Bjerkandera sp. BOS55", Enzyme and Microbial Technology, vol. 32, 2003; pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of *Thermomyces lanuginosus* Lipase by Detergents", Biochemistry, vol. 44, pp. 1719-1730, 2005.

Mohsen et al., "Specificity of Lipase Produced by Rhyopus Delemar and Its Utilization in Bread Making", Egypt. J Food. Sci. vol. 14, No. 1, pp. 175-182.

Molecular Biological Methods for Bacillus—Chapter 3 (Ed. C.R. Harwood and S.M. Cutting) 1990, John Wiley and Sons Ltd, Chichester, UK.

Mølgaard, Anne, et al., "Rhamnogalacturonan acetylesterase elucidates the structure and function of a new family of hydrolases", Structure, vol. 9, No. 4, 2000.

Molochnaya Promyshlennost 1980 No. 11 21-25, 47—abstract from Food Sci & Tech Abs.

Monick John A., Alcohols, Their Chemistry, Properties and Manufacture.

Monographs for Emulsifiers for Foods, EFEMA Nov. 1985 2nd Edition.

Moore, Charles M., et al., "Metal ion homeostasis in *Bacillus subtilis*", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning The Fusicoccum Anamorph of Botryosphaneria Ribis"; vol. Xxx, pp. 117-125; Oct.-Dec. 1987.

Morinaga et al Biotechnology (1984) 2, p. 636-639.

Morten, T. & A., Letter, Rodovre, Jul. 2004.

Mukherjee, Kumar D. et al., "Enrichment of γ-linolenic acid from fungal oil by lipase-catalysed reactions", Appl. Microbiol Biotechnol (1991), vol. 35, pp. 579-584.

Murakami, Mototake, et al., "Transesterification of Oil by Fatty Acid-Modified Lipase", Technical Research Institute.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.
N.V. Nederlandsch Octrooibureau Terms and Conditions.
Nagano, et al.; "Cloning and Nucleotide Sequence of cDNA Encoding a Lipase from *Fusarium keteroporum*"; J. Biochem (1994); vol. 116; pp. 535-540.
Nagao et al, J. Biochem 124, 1124-1129, 1998.
Nagao et al, J. of Bioscience and Bioengineering vol. 89, No. 5, 446-450, 2000.
Nagao et al, J. of Molecular Catalysis B: Enzymatic 17 (2002) 125-132.
Nagao et al, JAOCS vol. 78, No. 2, 2001.
Nagao, Toshihiro et al., "Cloning and Nucleotide Sequence of CDNA Encoding a Lipase from *Fusarium heterosporum*", J. Biochem., vol. 116, pp. 535-540, 1994.
Nagao, Toshihiro et al., "Expression of Lipase cDNA from *Fusarium heterosporum* by *Saccharomyces cereviisiae:* High-Level Production and Purification", Journal of Fermentation and Bioengineering, 1996, vol. 81, No. 6, pp. 488-492.
Nagodawlthana et al., "Enzymes in Food Processing", Third Edition, 1993, Academic Press, Inc.
National Research Council (U.S.) Committee on Specifications of the Food Chemicals Codex, "Lipase Activity" in *Food Chemicals Codex* (1981) National Academy Press, Washington, D.C. pp. 492-493.
Needleman & Wunsch (1970), J. of Molecular Biology 48, 443-453.
Nelson and Long, Analytical Biochemistry (1989), 180, p. 147-151.
Nerland A H, Journal of Fish Diseases, vol. 19, No. 2, 1996, pp. 145-150.
Néron, et al., "Effects of lipase and the phosphlipase on the lipids hydrolysis during mixing in correlation with the oxygen consumption by wheat flour dough during kneading" available at http://www.cnam.fr/biochimie.
Ness, Jon. E., et al., "DNA shuffling of subgenomic sequences of subtilisin" Nature Biotechnology, vol. 17, Sep. 1999.
Nestle Research Center, Brochure for "Food Colloids 2006" in Montreux, Switzerland, Apr. 23-26, 2006.
Neugnot Virginie et al, European Journal of Biochemistry, 2002, vol. 269, pp. 1734-1745.
Newport, G., et al., "KEX2 Influences *Candida albicans* Proteinase Secretion and Hyphal Formation", The Journal of Biological Chemistry, 1997, vol. 272, No. 46, pp. 28954-28961.
Nicolas, Anne, et al., "Contribution of Cutinase Serine 42 Side Chain to the Stabilization of the Oxyanion Transition State", Biochemistry, vol. 35, pp. 398-410, 1996.
Nielsen et al., "Lipases A and B from the yeast *Candida antarctica*".
Nierle W et al, Fette Seifen Anstrichmittel (1981), vol. 83 (10), p. 391-395.
Nierle, Von W. et al. "Weizenlipide: Funktion and Einflub bei der Verarbeitung des Mehles".
Nierle, W., et al., "Versuche zur Verlangerung der Haltbarkeit von Dartoffelprodukten", Chem. Mikrobiol. Technol. Lebensm., 1975, vol. 3, pp. 172-175.
Nobutoshi M et al., Tetrahedron Letters (1991), vol. 31 (1), p. 1131-4.
Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".
Novozymes Merno—Test of lipases for EP1193314B1, Jul. 6, 2005.
Novozymes Report 2002 Annual Report.
Novozymes, "Biowhitening—a new concept for steamed bread", *BioTimes*, Jan. 2005.
Novozymes, "Breakthrough: Less Fattening Fried Food" *BioTimes*, Jun. 2001, No. 2.
Novozymes, "Enzymes for dough strengthening", 2001.
Novozymes, "Lipopan F BG- application and mechanism of a new lipase for bread baking" (Draft) *Cereal Food* (2003) (Author: Drost-Lustenberger, C. et al.).
Novozymes, "Lipopan F BG", *Cereal Foods*.
Novozymes, "Mechanism studies of the new lipase".
Novozymes, "Product Sheet for Lipopan F BG", *Cereal Food*, (2001).
Novozymes, "Product Sheet for Lipopan FS BG", *Cereal Food* (2002).
Novozymes, "Product Sheet for Lipopan S BG", *Cereal Food* (2002).
Novozymes, "Product Sheet for Noopazyme".
Novozymes, "Product Sheet for Novozym 27016" (draft);
Novozymes, "Product Sheet for Novozym 27041" (draft).
Novozymes, "Product Sheet for Novozym 27019" (draft).
Novozymes, "Product Sheet for Novozym 27080" (draft).
Novozymes, "Product Sheet for Novozym 27106".
Novozymes, "Product Sheet: Enzyme Business, Noopazyme" (draft).
Novozymes, "Product Sheet: Enzyme Business, Novozym 27019" (draft).
Novozymes, "Product Sheet: Enzyme Business, Novozym 677 BG".
Novozymes, "Revolutionizing baking", *BioTimes* (2002) pp. 6-7.
Novozymes, "Strong sales for lipase that makes dough stronger" *BioTimes*, Dec. 2003.
Novozymes, "The Novozyme Touch: Make your mark on the future".
Novozymes, "The perfect roll every time for steers", *BioTimes*, Sep. 2003.
Novozymes, "The value of innovation", *BioTimes*, Mar. 2004.
Novozymes, "The vital role of technical service in baking", *BioTimes*, Jun. 2004.
Novozymes, Lipopan 50 BG, Product Sheet.
Novozymes, Lipopan 50 BG, Product Specification.
Novozymes, Lipopan F BG, Product Data Sheet.
Novozymes, Lipopan FS BG, Product Sheet.
Novozymes. Enzymes at work.
NY metode til aktivitetsbestemme fedtnedbrydende vaskemiddelenzy.
Nylander et al., "Interaction between lipids and lipases A collection of papers presented at the European Meeting on lipid and lipase interaction at Lund University".
Ognjenovic Radomir et al, Acceleration of ripening of semi-hard cheese by proteolytic and lipolytic enzymes.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
O'Mahony et al. Hydrolysis of the lipoprotein fractions of milk by Phospholipase C.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of *Alternaria alternata* and *Fusarium oxysporum* and certain properties of their lipids", Microbios Letters, vol. 39, pp. 131-135, 1988.

Ostrovskaya L K et al, Dokl Akad Nauk SSSR, (vol. 186(4), p. 961-3) p. 59-61.

O'Sullivan et al, J Plant Physiol, vol. 313, (1987) p. 393-404.

Outtrup, Günther H., et al., "Properties and Application of a Thermostable Maltogenic Amylase Produced by a Strain of Bacillus Modified by Recombinant-DNA Techniques", Starch/Starke, vol. 36, No. 12, pp. 405-411.

Palomo, Jose M., et al., "Enzymatic production of (3S, 4R)-(−)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.

Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.

Pariza, Michael, et al., "Evaluating the safety of Microbiol Enzyme Preparations Used in Food Processing: Update for a New Century", Regulatory Toxicology and Pharmacology, vol. 33, pp. 173-186.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.

Peelman F, et al, Protein Science Mar. 1998; 7(3): 587-99.

Penninga et al, Biochemistry (1995), 3368-3376.

Persson, Mattias, et al., "Enzymatic fatty acid exchange in digalactosyldiacylglycerol", Chemistry and Physics of Lipids, vol. 104, 2000, pp. 13-21.

Peters, G.H., et al., "Active Serine Involved in the Stablization of the Active Site Loop in the *Humicola lanuginosa* Lipase", Biochemistry, 1998, vol. 37, pp. 12375-12383.

Peters, G.H., et al.; "Dynamics of *Rhizomucor miehei* lipase in a lipid or aqueous environment: Functional role of glycines"; Dept. of Biochemistry and Molecular Biology, University of Leeds.

Peters, G.H., et al.; "Essential motions in lipases and their relationship to the biological function".

Peters, Günther H., et al., "Theoretical Investigation of the Dynamics of the Active Site Lid in *Rhizomucor miehei* Lipase", Biophysical Journal, vol. 71, 1996, pp. 119-129.

Philippine Patent Application Serial No. 31068.

*Phytochemical Dictionary* "Chapter 4, Sugar Alcohols and Cyclitols".

Picon et al. Biotechnology letters vol. 17 nr 10 pp. 1051-1056.

Plijter J and JHGM Mutsaers, The surface rheological properties of dough and the influence of lipase on it, Gist-brocades, Bakery Ingredients Division, Oct. 1994.

Plou et al, J. Biotechnology 92 (2002) 55-66.

Ponte J G, Cereal Chemistry (1969), vol. 46(3), p. 325-29.

Poulsen, C.H., et al., "Effect and Functionality of Lipases in Dough and Bread", The British Library.

Poulsen, Charlotte, et al. "Purification and Characterization of a Hexose Oxidase with Excellent Strenghening Effects in Bread".

Product Data Sheet, Bakezyme P 500 BG, DSM Food Specialties.

Product Description PD 40084-7a Grindamyl Exel 16 Bakery Enzyme.

Product Sheet B1324a-GB—Lecitase$^R$ Novo, Novo Nordisk.

Product Sheet, Lipozyme® 10.000 L, Novo Nordisk.

Punt and van den Hondel, Meth. Enzym., 1992, 216:447-457.

Pyler, E.J., "Baking Science and Technology Third Edition", vol. 1, 1988.

Pyler, E.J., "Baking Science and Technology Third Edition", vol. II, 1988.

Queener et al. (1994) Ann N Y Acad Sci. 721, 178-93.

Rambosek and Leach, CRC Crit. Rev. Biotechnol., 1987, 6:357-393.

Rapp, Peter, et al., "Formation of extracellular lipases by filamentous fungi, yeasts, and bacteria", Enzyme Microb. Technol., 1992, vol. 14, November.

Rapp, Peter; "Production, regulation, and some properties of lipase activity from *Fusarium oxysporum* f. sp. *vasinfectum*"; Enzyme and Microbial Technology(1995); vol. 17; pp. 832-838.

Reetz M.T., Jaeger K.E. Chem Phys Lipids. Jun. 1998; 93(1-2): 3-14.

Reetz Manfred T, Current Opinion in Chemical Biology, Apr. 2002, vol. 6, No. 2, pp. 145-150.

Reiser J et al. (1990) Adv Biochem Eng Biotechnol. 43, 75-102.

Richardson & Hyslop, pp. 371-476 in Food Chemistry, 1985, second edition, Owen R. Fennema (ed), Manel Dekker, Inc, New York and Basel.

Richardson and Hyslop, "Enzymes: XI—Enzymes Added To Foods During Processing" in *Food Chemistry*, Marcel Dekker, Inc., New York, NY 1985.

Arskog and Joergensen, "Baking performance of prior art lipases from *Candida cylindracea* and *Aspergillus foeditus* and their actiivty on galactolipids in dough", Novozymes Report 2005.

Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.

Richardson, Toby H., et al., "A Novel, High Performance Enzyme for Starch Liquefaction", The Journal of Biological Chemistry, vol. 277, No. 29, Issue of Jul. 19, pp. 25501-26507, 2002.

Roberts et al. (1992) Gene 122(1), 155-61.

Roberts, et al.; "Extracellular Lipase Production by Fungi from Sunflower Seed"; Mycologia(1987); vol. 79(2); pp. 265-273.

Roberts, Ian N., et al., Heterologous gene expression in *Aspergillus niger*: a glucoamylase-porcine pancreatic prophospholipase A2 fusion protein is secreted and processed to yield mature enzyme.

Robertson et al, Journal of Biological Chemistry, 1994, 2146-2150.

Rodrigues, et al.; "Short Communication: Bioseparations with Permeable Particles"; Journal of Chromatography & Biomedical Applications(1995); vol. 655; pp. 233-240.

Rogalska, Ewa, et al., "Stereoselective Hydrolysis of Triglycerides by Animal and Microbial Lipases", Chirality, vol. 5, pp. 24-30, 1993.

Rose, et al.;"CODEHOP (Consensus-Degenerate Hybrid Oligonucleotide Primer) PCR primer design"; Nucleic Acids Research(2003); vol. 31(13); pp. 3763-3766.

Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.

Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.

Sahsah, Y., et al., "Enzymatic degradation of polar lipids in *Vigna unguiculata* leaves and influence of drought stress", Physiologia Plantarum, vol. 104, pp. 577-586, 1998.

Sahsah, Y., et al., "Purification and characterization of a soluble lipolytic acylhydrolase from Cowpea (vigna unguiculaga L.) leaves", Biochimica et Biophysica Acta, vol. 1215, pp. 66-73, 1994.

Saiki R.K. et al Science (1988) 239, pp. 487-491.

Saito, Kunihiko, et al., "Phospholipase B from *Penicillium notatum*", Methods in Enzymology, vol. 197.

Sakai, Norio, et al., "Human glactocerebrosidase gene: promoter analysis of the 5'-flanking region and structural organization", Biochimica et Biophysica Acta, vol. 1395, pp. 62-67, 1998.

Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.

Sales Range for Baking Improver and Premix Manufacturers from DSM Bakery Ingredients.

Sambrook et al, Chapters 1, 7, 9, 11, 12 and 13—Molecular Cloning a laboratory manual, Cold Spring Harbor Laboratory Press (1989).

Sambrook, J., et al. "A Laboratory Manual, Second Edition", Plasmid Vectors, 1989.

Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.

Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).

Saxena, et al.; "Purification Strategies for Microbial Lipases"; Journal of Microbilogical Methods (2003); pp. 1-18.

Scheib et al.; "Stereoselectivity of *Mucorales lipases* toward triradylglycerols—A simple solution to a complex problem"; Protein Science (1999); vol. 8; pp. 215-221.

Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.

Schofield, J. David, "Wheat Structure, Biochemistry and Functionality", Department of Food Science and Technology.

Scopes, Robert K., "Section 8.4: Ultrafiltration" in *Protein Purification Principles and Practice, Third Edition* (1994) Springer-Verlag, New York, p. 267-9.

Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.

Shehata PhD Thesis.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.

Shillcock, Julian C., et al., "Tension-induced fusion of bilayer membranes and vesicles", Advance Online Publication.

Shimada et al, J. of Bioscience and Bioengineering vol. 91, No. 6, 529-538 (2001).

Shimada et al, J. of Fermentation and Bioengineering vol. 75, No. 5, 349-352 (1993).

Shimada et al, JAOCS vol. 71, No. 9, (Sep. 1994).

Shin, et al.; "Butyl-Toyopearl 650 as a New Hydrophobic Adsorbent for Water-Soluable Enzyme Proteins"; Analytical Biochemistry(1984); vol. 138; pp. 259-261.

Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.

Si, Joan Qi, "Enzymes, Baking, Bread-Making".

Si, Joan Qi, "Synergistic Effect of Enzymes for Breadbaking".

Si, Joan Qi, et al. "Enzymes for bread, noodles and non-durum pasta".

Si, Joan Qi, et al., "Novamyl—A true Anti-Staling Enzyme", Cereal Food, p. 1, No. 20.

Si, Joan Qi, et al., "Synergistic Effect of Enzymes for Breadbaking".

Si, Joan Qi, "New Enzymes for the Baking Industry"; Food Tech Europe (1996) pp. 60-64.

Sias B et al, Biochemistry, (2004), vol. 43(31), p. 10138-48.

Siew W.L. & Ng W.L. (1999) Influence of diglycerides on crystalisation of palm oil, in Journal of Science of Food and Agriculture 79:722-726.

Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.; "Comparison of Intra- and extralcualr isozyme banding patterns of *Fusarium oxysporum*"; Mycol. Res. (1998); vol. 102 (9); pp. 1077-1084.

Slotboom et al Chem. Phys. Lipids 4 (1970) 15-29.

Smith, George P.; "The Progeny of sexual PCR"; Nature; vol. 370; No. 18; Aug. 4, 1994.

Smith, Timothy L., et al., "The promoter of the glucoamylase-encoding gene of *Aspergillus niger* functions in *Ustilago maydis*", Gene. 88, 259-262, 1990.

Soe, J.B., "Analyses of Monoglicerides and Other Emulsifiers by Gaschromatography".

Solares, Laura F., et al., "Enzymatic resolution of new carbonate intermediates for the synthesis of (S)-(+)-zopiclone", Tetrahedron: Asymmetry, vol. 13, 2002, pp. 2577-2582.

Sols and De Le Fuente, "On the substrate specificity of glucose oxidase", Biochem et Biophysica Acta (1957) 24:206-7.

Sonntag N.O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospholipase A2 in the symbiotic fungus" The EMBO Journal, vol. 20, No. 18, pp. 5079-5090, 2001.

Sorensen, H.R., et al., "Effects of added enzymes on the physicochemical characteristics on fresh durum-pasta".

Sosland, Josh, "Alive and kicking", Milling & Baking News, Feb. 24, 2004.

Soumanou, Mohamed M., et al., "Two-Step Enzymatic Reaction for the Synthesis of Pure Structured Triacylglycerides", JAOCS, vol. 75, No. 6, 1998.

Spargeon, Brad, "In China, a twist: Forgers file patents".

Spendler, et al., "Functionality and mechanism of a new 2nd generation lipase for baking industry"—Abstract. 2001 AACC Annual Meeting; Symposia at Charlotte, NC. Oct. 14-18, 2001.

Spradlin J E, Biocatalysis in Agric. Technol., ACS Symposium, 389(3), 24-43 (1989).

Sreekrishna K et al (1988) J Basic Microbiol. 28(4), 265-78.

Stadler et al., "Understanding Lipase Action and Selectivity", CCACAA, vol. 68, No. 3, pp. 649-674, 1995.

Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.

Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.

Stemmer, Willem P.C.; "Rapid evolution of a protein in vitro by DNA shuffling"; Affymax Research Institute, Nature, vol. 370, Aug. 4, 1994.

Sternberg, M., "Purification of Industrial Enzymes with Polyacrylic Acids", Process Biochemistry, Sep. 1976.

Strickland, James A., et al., "Inhibition of Diabrotica Larval Growth by Patatin, the Lipid Acyl Hydrolase from Potato Tubers", Plant Physiol, vol. 109, pp. 667-674, 1995.

Sudbery et al (1988) Biochem Soc Trans. 16(6), 1081-3.

Sugatani, Junko, et al., "Studies of a Phospholipase B from Penicillium Notatum Substrate Specificity and Properties of Active Site", Biochimica et Biophysica Acta, vol. 620, 1980, pp. 372-386.

Sugimoto et al., Agric. Biol. Chem. 47(6), 1201-1206 (1983).

Sugiyama et al., "Molecular cloning of a second phospholipase B gene, caPLB2 from *Candida albicans*", Medical Mycology, vol. 37, 1999.

Svendsen, A. "Engineered lipases for practical use", INFORM (1994) 5(5):619-623.

Svendsen, Allan, "Lipase protein engineering" Biochimica et Biophysica Acta, vol. 1543, 2000, pp. 223-238.

Svendsen, Allan, et al., "Biochemical properties of cloned lipases from the Pseudomonas family", Biochimica et Biophysica Acta, vol. 1259, 1995, pp. 9-17.

Sweigard, James A., et al., "Cloning and analysis of CUT1, a cutinase gene from *Magnaporthe grisea*", Mol. Gen. Genet., 232:174-182, 1992.

Swinkels et al (1993) Antonie van Leeuwenhoek 64, 187-201.

Sztajer H et al Acta Biotechnol, vol. 8, 1988, pp. 169-175.

Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.

Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.

The First European Symposium of Enzymes on Grain Processing—Proceedings.

The New Enzyme Operatives, Ingredient Technology, 50, Aug. 1997.

Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Bioctechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuchiya, Atsushi et al, Fems Microbiology Letters, vol. 143, pp. 63-67.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, "Appendix: Classification and Index of Fungi mentioned in the Text" in *Unknown*, p. 599-616.
Unknown, "Section I: Structure and Growth—Chapter 1: An Introduction to the Fungi" in *Unknown* pp. 1-16.
Unknown, *Studies on Lipase* (1964) p. 21.
Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from *Candida antarctica*", Structure 1994, vol. 2, No. 4.
Upton C et al TIBS Trends in Biochemical Sciences, Elsevier Publication (1995), vol. 20, pp. 178-179.
USDA, "Production of an Industrially Useful Fungal Lipase by a Genetically Altered Strain of *E. coli*", New Technology.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53 (23); p. 1253.
van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Den Berg. G, Regulatory status and use of lipase in various countries.
van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
van Nieuqenhuyzen, "Open Doors to baked goods".
van Oort, Maarten G et al, Biochemistry 1989 9278-9285.
van Solingen, Pieter, et al., "The cloning and characterization of the acyltransferase gene of penicillium chrysogenum", Agricultural University, Wageningen, The Netherlands.

Vaysse et al J. of Biotechnology 53 (1997) 41-46.
Villenueva, Inform, vol. 8, No. 6, Jun. 1997.
Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk mem brane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast *Torulaspora delbrueckii*", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Welter, et al; "Identification of Recombinant DNA"; pp. 424-431.
Wen-Chen Suen et al., "Improved activity and thermostability of *Candida antarctica* lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitaker, John R., et al., "Biocatalysis in Agricultural Biotechnology", ACS Symposium Series.
Whitehead, Michael, et al., "Transformation of a nitrate reductase deficient mutant of *Penicillium chrysogenum* with the corresponding *Aspergillus niger* and A. nidulans niaD genes", Mol Gen Genet, 216: 408-411, 1989.
Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.
Williams et al Protein Analysis by Integrated Sample Preparation, Chemistry, and Mass Spectrometry, Edited by Meyers.
Winnacker, Chapter 11, pp. 424-431 In From genes to clones: introduction to gene technology, VCH (1987).
Winnacker, E. "Chapter 11: Identification of Recombinant DNA" in *From Genes to Clones: Introduction to Gene Technology*, 1987 John Wiley & Sons.
Winther, Ole, et al., "Teaching computers to fold proteins", Physical Review, vol. 70, No. 030903, 2004.
Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.
Witt, Wolfgang et al., "Secretion of Phospholipase B From *Sac charomyces cerevisiae*", Biochimica et Biophysica Acta, vol. 795, 1984, pp. 117-124.
Wood et al., Eds., "Biomass, Part B, Lignin, Pectin, and Chitin", Methods in Enzymology (1988) vol. 161, Academic Press, San Diego.
Xu, Jun, et al., "Intron requirement for AFP gene expression in *Trichoderma viride*", Microbiology, 2003, vol. 149, pp. 3093-3097.
Yamaguchi et al, 1991, Gene 103:61-67.
Yamane et al., "High-Yield Diacylglycerol Formation by Solid-Phase Enzymatic Glycerolysis of Hydrogenated Beef Tallow", JAOCS, vol. 71, No. 3, Mar. 1994.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Yount, Nannette Y., et al., "Multidimensional signatures in antimicrobial peptides".
Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Bateman A et al, (2002) Nucleic Acids Res. 30, 276-280.

Becker T. "Separation and Purification Processes for Recovery of Industrial Enzymes" in R.K. Singh, S.S.H. Rizvi (eds): Bioseparation processes in Foods, Marcel Dekker, New York, pp. 427-445.

Bedre Brod med nyt enzym.

Bekkers et al, The use of genetic engineering to obtain efficient production of porcine pancreatic phospholipase A2 by *Saccharomyces cerevisiae*, (1991) Biochim Biophys Acta 1089(3), 345-51.

Bengtsson Olivecrona Gunilla et al. Phospholipase activity of milk lipoprotein lipase, Methods in Enzymology, vol. 197, 1991.

Bentley S D et al, Complete genome sequence of the model actinomycete *Streptomyces coelicolor* A3(2), Nature vol. 417, 2002, pp. 141-147.

Berger K.G. (1990) Recent developments in palm oil. In Oleagineux 45:437-443.

Berks, Ben C., "A common export pathway for proteins binding complex redox cofactors?" Molecular Microbiology, 1996, vol. 22, pp. 393-404.

Beucage S.L. et al, (1981) Tetrahedron Letters 22, p. 1859-1869.

Bieleski R.L., Chapter 5, Sugar Alcohols.

Bilyk, Alexander, et al., "Lipase-catalyzed triclyceride Hydrolysis in Organic Solvent", pp. 320-323, JAOCS, vol. 68, No. 5, May 1991.

Biocatalysts, Limited, Product Sheet for Lipomod(TM) 627P-L627P.

Biotekkomet falder hardt til jorden.

Birch et al., "Evidence of Multiple Extracellular Phospholipase Activities of *Aspergillus fumigatus*", Infection and Immunity, Mar. 1996, vol. 64, No. 3, 1996.

Birgitte Hugh-Jensen et al., "*Rhizomucor miehei* Triglyceride Lipase is Processed and Secreted from Transformed *Aspergillus oryzae*", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et al., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.

Bjorkling, Frederik, et al., "Lipase -mediated Formation of Peroxycarboxylic acids used in Catalytic Epoxidation of Alkenes", J. Chem. Soc., Chemical Communications, Issue 19, 1990.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Fems Microbiol. Lett., 1978, vol. 3, 85-87.

Blecker et al, Improved emulsifying and foaming of whey proteins after enzymic fat hydrolysis, (1997) J Food Science, vol. 62, No. 1.

Blumenthal, Cynthia Z., "Production of toxic metabolites in *Aspergillus niger, Aspergillus oryzae,* and *Trichoderma reesei*: justification of mycotoxin testing in food grade enzyme preparations derived from the three fungi", Regulatory Toxicology and Pharmacology, vol. 39, 2004, pp. 214-228.

* cited by examiner

BEST TRANSFORMANT

METHOD FOR PREPARING FLOUR DOUGHS AND PRODUCTS MADE FROM SUCH DOUGHS USING LIPASE

This application is a continuation of U.S. patent application Ser. No. 10/040,394, filed Jan. 9, 2002 now U.S. Pat. No. 6,852,346, which is a division of U.S patent application Ser. No.09/402,664, filed Oct. 22, 1999 now U.S Pat. No. 6,406,723.

FIELD OF THE INVENTION

The present invention relates to the field of food manufacturing, in particular to the preparation of improved bakery products and other farinaceous food products. Specifically, the invention concerns the use of glycerol oxidase as a dough strengthening agent and improvement of the quality of baked and dried products made from such improved doughs. There is also provided a method of improving the properties of doughs and baked product by combined use of glycerol oxidase and a lipase.

TECHNICAL BACKGROUND AND PRIOR ART

The "strength" or "weakness" of doughs are an important aspect of making farinaceous finished products from doughs, including baking. The "strength" or "weakness" of a dough is primarily determined by its content of protein and in particular the content and quality of the gluten protein is an important factor in that respect. Flours with a low protein content are generally characterized as "weak." Thus, the cohesive, extensible, rubbery mass which is formed by mixing water and weak flour will usually be highly extensible when subjected to stress, but it will not return to its original dimensions when the stress is removed.

Flours with a high protein content are generally characterized as "strong" flours and the mass formed by mixing such a flour and water will be less extensible than the mass formed from a weak flour, and stress which is applied during mixing will be restored without breakdown to a greater extent than is the case with a dough mass formed from a weak flour. Strong flour is generally preferred in most baking contexts because of the superior rheological and handling properties of the dough and the superior form and texture qualities of the finished baked or dried products made from the strong flour dough.

Doughs made from strong flours are generally more stable. Stability of a dough is one of the most important characteristics of flour doughs. Within the bakery and milling industries it is known to use dough "conditioners" to strengthen the dough to increase its stability and strength. Such dough conditioners are normally non-specific oxidizing agents such as e.g. iodates, peroxides, ascorbic acid, K-bromate or azodicarbonamide and they are added to dough with the aims of improving the baking performance of flour to achieve a dough with improved stretchability and thus having a desirable strength and stability. The mechanism behind this effect of oxidizing agents is that the flour proteins, in particular gluten contains thiol groups which, when they become oxidized, form disulphide bonds whereby the protein forms a more stable matrix resulting in a better dough quality and improvements of the volume and crumb structure of the baked products.

However, the use of several of the currently available non-specific oxidizing agents is either objected to by consumers or is not permitted by regulatory bodies. Hence it has been attempted to find alternatives to these conventional flour and dough additives, and the prior art has i.a. suggested the use of glucose oxidase and hexose oxidase for this purpose.

Glycerol oxidase is an oxidoreductase which is capable of oxidizing glycerol. Different types of glycerol oxidase have been described in the literature. Some of these glycerol oxidases need co-factors in order to oxidize glycerol (Shuen-Fu et al., 1996. Enzyme Micro. Technol., 18:383-387).

However, glycerol oxidase from *Aspergillus japonicus* does not require any co-factors in the oxidation of glycerol to glyceraldehyde (T. Uwajima and O. Terada, 1980. Agri. Biol. Chem. 44:2039-2045).

This glycerol oxidase has been characterized by T. Uwajima and O. Terada (Methods in Enzymology, 1982, 89:243-248) and T. Uwajima et al. (Agric. Biol. Chem., 1979, 43:2633-2634), and has a pH optimum at 7.0 and $K_m$ and $V_{max}$ are 10.4 mM and 935.6 μmol $H_2O_2$ $min^{-1}$ respectively using glycerol as substrate. The enzyme is most active on glycerol but also other substrates like dihydroxyacetone, 1,3-propanediol, D-galactose ad D-fructose are oxidized by glycerol oxidase.

Glycerol oxidase not requiring co-factors has also been isolated from *Penicillium* and characterized by Shuen-Fuh Lin et al. (Enzyme Micro. Technol., 1996, 18:383-387). This enzyme has optimum activity in the pH range from 5.5 to 6.5 at 30° C. The enzyme is stable between 20 and 40° C. but loses its activity at temperatures above 50° C.

Other potential sources for glycerol oxidase according to the invention include different fungal species as disclosed in DE-2817087-A, such as *Aspergillus oryzae, Aspergillus parasiticus, Aspergillus flavus, Neurospora crassa, Neurospora sitophila, Neurospora tetrasperma, Penicillium nigricans, Penicillium funiculosum* and *Penicillium janthinellum*.

Glycerol oxidase isolated from the above natural sources has been used for different applications. Thus, glycerol oxidase from *Aspergillus japonicus* has been used for glycoaldehyde production from ethylene glycol (Kimiyasu Isobe and Hiroshi Nishise, 1995, Journal of Molecular Catalysis B: Enzymatic, 1:37-43). Glycerol oxidase has also been used in the combination with lipoprotein lipase for the determination of contaminated yolk in egg white (Yioshinori Mie, 1996. Food Research International, 29:81-84). DE-2817087-A and U.S. Pat. No. 4,399,218 disclose the use of glycerol oxidase for the determination of glycerol.

It has now been found that the addition of a glycerol oxidase to a flour dough results in an increased resistance hereof to deformation when the dough is stretched, i.e. this enzyme confers to the dough an increased strength whereby the dough becomes less prone to mechanical deformation. Accordingly, glycerol oxidase is highly useful as a dough conditioning agent in the manufacturing of flour dough based products including not only bread products but also other products made from flour doughs such as noodles and alimentary paste products.

It has also been found that the dough strengthening effect of glycerol oxidase is potentiated significantly when it is combined with a lipase, which in itself does not affect the dough strength. Furthermore, the combined use of glycerol oxidase and lipase results in an improvement of bread quality, in particular in respect of specific volume and crumb homogeneity, which is not a simple additive effect, but reflects a synergistic effect of these two types of enzymes.

SUMMARY OF THE INVENTION

Accordingly, the invention relates in a first aspect to a method of improving the rheological properties of a flour dough and the quality of the finished product made from the dough, comprising adding to the dough 10 to 10,000 units of a glycerol oxidase per kg of flour.

In a further aspect there is provided a method of improving the rheological properties of a flour dough and the quality of the finished product made from the dough, comprising adding to the dough a glycerol oxidase and a lipase.

The invention pertains in a still further aspect to dough improving composition comprising a glycerol oxidase and at least one further dough ingredient or dough additive.

In still further aspects, the invention relates to the use of a glycerol oxidase for improving the rheological properties of a flour dough and the quality of the finished product made from the dough and to the use of a glycerol oxidase and a lipase in combination for improving the rheological properties of a flour dough and the quality of the finished product made from the dough.

DETAILED DISCLOSURE OF THE INVENTION

In one aspect, the present method provides a method of improving the rheological properties of flour doughs.

The expression "rheological properties" as used herein refers particularly to the effects of dough conditioners on dough strength and stability as the most important characteristics of flour doughs. According to American Association of Cereal Chemists (AACC) Method 36-01A the term "stability" can be defined as "the range of dough time over which a positive response is obtained and that property of a rounded dough by which it resists flattening under its own weight over a course of time". According to the same method, the term "response" is defined as "the reaction of dough to a known and specific stimulus, substance or set of conditions, usually determined by baking it in comparison with a control".

As it is mentioned above, it is generally desirable to improve the baking performance of flour to achieve a dough with improved stretchability and thus having a desirable strength and stability by adding oxidizing agents which cause the formation of protein disulphide bonds whereby the protein forms a more stable matrix resulting in a better dough quality and improvements of the volume and crumb structure of baked products.

Thus, the term "rheological properties" relates to the above physical and chemical phenomena which in combination will determine the performance of flour doughs and thereby also the quality of the resulting products.

The method comprises, as it is mentioned above, the addition of an effective amount of a glycerol oxidase to the dough. It will be understood that the addition can be either to a component of the dough recipe or to the dough resulting from mixing all of the components for the dough. In the present context, "an effective amount" is used to indicate that the amount is sufficient to confer to the dough and/or the finished product improved characteristics as defined herein. Specifically, such an amount is in the range of 10 to 10,000 units of glycerol oxidase per kg flour.

In one useful embodiment of the method according to the invention, the glycerol oxidase can, as it is described in details herein, be isolated from a bacterial species, a fungal species, a yeast species, an animal cell including a human cell or a plant cell. Examples of glycerol oxidase producing fungal species are species belonging to the *genera Aspergillus, Neurospora* and *Penicillium*, such as *A. japonicus, A. oryzae, A. parasiticus, A. flavus, Neurospora crassa, N. sitophila, N. tetrasperma, Penicillium nigricans, P. funiculosum* and *P. janthinellum*.

Glycerol oxidase can be derived as a native enzyme from natural sources such as the above.

It is one objective of the invention to provide improved bakery products. In accordance with the invention, a bakery product dough including a bread dough is prepared by mixing flour with water, a leavening agent such as yeast or a conventional chemical leavening agent, and an effective amount of glycerol oxidase under dough forming conditions. It is, however, within the scope of the invention that further components can be added to the dough mixture.

Typically, such further dough components include conventionally used dough components such as salt, sweetening agents such as sugars, syrups or artificial sweetening agents, lipid substances including shortening, margarine, butter or an animal or vegetable oil, glycerol and one or more dough additives such as emulsifying agents, starch degrading enzymes, cellulose or hemicellulose degrading enzymes, proteases, lipases, non-specific oxidizing agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fiber substances.

Conventional emulsifying agents used in making flour dough products include as examples monoglycerides, diacetyl tartaric acid esters of mono- and diglycerides of fatty acids, and lecithins e.g. obtained from soya. Among starch degrading enzymes, amylases are particularly useful as dough improving additives. Other useful starch degrading enzymes which may be added to a dough composition include glucoamylases and pullulanases. In the present context, further interesting enzymes are xylanases and oxidoreductases such as glucose oxidase, pyranose oxidase, hexose oxidase, sulfhydryl oxidase, and lipases.

A preferred flour is wheat flour, but doughs comprising flour derived from other cereal species such as from rice, maize, barley, rye and durra are also contemplated.

In accordance with the invention, the dough is prepared by admixing flour, water, the glycerol oxidase and optionally other ingredients and additives. The glycerol oxidase can be added together with any dough ingredient including the water or dough ingredient mixture or with any additive or additive mixture. The dough can be prepared by any conventional dough preparation method common in the baking industry or in any other industry making flour dough based products.

The glycerol oxidase can be added as a liquid preparation or in the form of a dry powder composition either comprising the enzyme as the sole active component or in admixture with one or more other dough ingredients or additive.

The amount of the glycerol oxidase added is an amount which results in the presence in the dough of 10 to 5,000 units (as defined in the following) such as 10 to 2,500 units per kg of flour. In useful embodiments, the amount is in the range of 20 to 1,500 units per kg of flour.

The effect-of the glycerol oxidase on the rheological properties of the dough can be measured by standard methods according to the International Association of Cereal Chemistry (ICC) and the American Association of Cereal Chemistry (AACC) including the amylograph method (ICC 126), the farinograph method (AACC 54-21) and the extensigraph method (AACC 54-10). The AACC method 54-10 defines the extensigraph in the following manner: "the extensigraph records a load-extension curve for a test piece of dough until it breaks. Characteristics of load-extension curves or extensigrams are used to assess general quality of flour and its responses to improving agents". In effect, the extensigraph method measures the relative strength of a dough. A strong dough exhibits a higher and, in some cases, a longer extensigraph curve than does a weak dough.

In a preferred embodiment of the method according to the invention, the resistance to extension of the dough in terms of the ratio between the resistance to extension (height of curve, B) and the extensibility (length of curve, C), i.e. the B/C ratio as measured by the AACC method 54-10 is increased by at least 10% relative to that of an otherwise similar dough not containing glycerol oxidase. In more preferred embodiments, the resistance to extension is increased by at least 20%, such as at least 50% and in particular by at least 100%.

It has been found that the addition of glycerol oxidase to bakery product doughs results in bakery products such as yeast leavened and chemically leavened products in which the specific volume is increased relative to an otherwise similar bakery product, prepared from a dough not containing glycerol oxidase. In this context, the expression "specific volume" is used to indicate the ratio between volume and weight of the product. It has been found that, in accordance with the above method, the specific volume can be increased significantly such as by at least 10%, preferably by at least 20%, including by at least 30%, preferably by at least 40% and more preferably by at least 50%.

The method according to the invention is highly suitable for improving the rheological properties and quality of the finished products of conventional types of yeast leavened bread products based on wheat flour, such as loaves and rolls. The method is also suitable for improving the rheological properties of doughs containing chemical leavening agents (baking powder) and the quality of products made from such doughs. Such product include as examples sponge cakes and muffins.

In one interesting aspect, the invention is used to improve the rheological properties of doughs intended for noodle products including "white noodles" and "chinese noodles" and to improve the textural qualities of the finished noodle products. A typical basic recipe for the manufacturing of noodles comprises the following ingredients: wheat flour 100 parts, salt 0.5 parts and water 33 parts. Furthermore, glycerol is often added to the noodle dough. The noodles are typically prepared by mixing the ingredients in an appropriate mixing apparatus followed by rolling out the noodle dough using an appropriate noodle machine to form the noodle strings which are subsequently air dried.

The quality of the finished noodles is assessed i.a. by their colour, cooking quality and texture. The noodles should cook as quickly as possible, remain firm after cooking and should preferably not loose any solids to the cooking water. On serving the noodles should preferably have a smooth and firm surface not showing stickiness and provide a firm "bite" and a good mouthfeel. Furthermore, it is important that the white noodles have a light colour.

Since the appropriateness of wheat flour for providing noodles having the desired textural and eating qualities may vary according to the year and the growth area, it is usual to add noodle improvers to the dough in order to compensate for sub-optimal quality of the flour. Typically, such improvers will comprise dietary fiber substances, vegetable proteins, emulsifiers and hydrocolloids such as e.g. alginates, carrageenans, pectins, vegetable gums including guar gum and locust bean gum, and amylases, and as mentioned above, glycerol.

It is therefore an important aspect of the invention that the glycerol oxidase according to the invention is useful as a noodle improving agent optionally in combination with glycerol and other components currently used to improve the quality of noodles. Thus, it is contemplated that noodles prepared in accordance with the above method will have improved properties with respect to colour, cooking and eating qualities including a firm, elastic and non-sticky texture and consistency.

In a further useful embodiment, the dough which is prepared by the method according to the invention is a dough for preparing an alimentary paste product. Such products which include as examples spaghetti and maccaroni are typically prepared from a dough comprising main ingredients such as flour, eggs or egg powder and/or water. After mixing of the ingredient, the dough is formed to the desired type of paste product and air dried. It is contemplated that the addition of glycerol oxidase to a paste dough, optionally in combination with glycerol, will have a significant improving effect on the extensibility and stability hereof resulting in finished paste product having improved textural and eating qualities.

In a useful embodiment, there is provided a dough improving method wherein at least one further enzyme is added to the dough ingredient, dough additive or the dough. In the present context, suitable enzymes include cellulases, hemicellulases, xylanases, starch degrading enzymes, oxidoreductases and proteases.

In a further aspect, the invention relates to a method of improving the rheological properties of a flour dough and the quality of the finished products made from the dough which comprises that both a glycerol oxidase and a lipase is added to the dough.

It was surprisingly found that the two types of enzymes were capable of interacting with each other under the dough conditions to an extent where the effect on improvement of the dough strength and bread quality by the enzymes was not only additive, but the effect was synergistic.

Thus, with respect to improvement of dough strength it was found that with glycerol oxidase alone, the B/C ratio as measured after 45 minutes of resting was increased by 34%, with lipase alone no effect was observed. However, when combining the two enzymes, the B/C ratio was increased by 54%, i.e. combining the glycerol oxidase with the lipase enhanced the dough strengthening effect of glycerol oxidase by more than 50%. Thus, one objective of combining glycerol oxidase and a lipase is to provide an enhancement of the dough strengthening effect of glycerol oxidase by at least 25% such as at least 50% including at least 75%, determined as described herein.

In relation to improvement of finished product, it was found that the combined addition of glycerol oxidase and a lipase resulted in a substantial synergistic effect in respect to crumb homogeneity as defined herein. Also, with respect to the specific volume of baked product a synergistic effect was found. Thus, for a bread product, the addition of lipase alone typically results in a negligible increase of the specific volume, addition of glycerol oxidase alone in an increase of about 25%, whereas a combined addition of the two enzymes results in an increase of more than 30%.

Further in relation to improvement of the finished product, it was found that the addition of lipase resulted in modification of the glycolipids, monogalactosyl diglyceride and digalactosyl diglyceride present in dough. These components were converted to the more polar components monogalactosyl monoglyceride and digalactosyl monoglyceride. As galactosyl monoglycerides are more surface active components than galactosyl diglycerides it is assumed that galactosyl monoglycerides contributed to the observed improved crumb cell structure and homogeneity. Thus, one objective of using lipase is to hydolyse at least 10% of the galactosyl diglycerides normally present in a flour dough to the corresponding galactosyl monoglycerides, such as at least 50% including at least 100%.

The details of such a method using combined addition of glycerol oxidase and lipase are, apart from the use of a lipase in combination with glycerol oxidase, substantially similar to those described above for a method according to the invention which does not require the addition of a lipase.

When using, in accordance with the invention, a lipase in combination with a glycerol oxidase, the amount of lipase is typically in the range of 10 to 100,000 lipase units (LUS) (as defined in the following) per kg flour including the range of 10 to 20,000 LUS, e.g. 100 to 15,000 LUS such as 500 to 10,000 LUS.

Lipases that are useful in the present invention can be derived from a bacterial species, a fungal species, a yeast species, an animal cell and a plant cell. Whereas the enzyme may be provided by cultivating cultures of such source organisms naturally producing lipase, it may be more convenient and cost-effective to produce it by means of genetically modified cells such as it is described in details in the following examples. In the latter case, the term "derived" may imply that a gene coding for the lipase is isolated from a source organism and inserted into a host cell capable of expressing the gene.

Thus, the enzyme may in a useful embodiment be derived from an *Aspergillus* species including as examples *A. tubigensis, A. oryzae* and *A. niger*.

Presently preferred lipases include the lipase designated Lipase 3, the production and characteristics of which is described in details in the following examples, or a mutant of this enzyme. In the present context, the term "mutant" refers to a lipase having, relative to the wild-type enzyme, an altered amino acid sequence. A further preferred lipase is the lipase found in the commercial product, GRINDAMYL™ EXEL 16.

In a further aspect of the invention there is provided a dough improving composition comprising a glycerol oxidase and at least one further dough ingredient or dough additive.

The further ingredient or additive can be any of the ingredients or additives which are described above. The composition may conveniently be a liquid preparation comprising the glycerol oxidase. However, the composition is conveniently in the form of a dry composition.

The amount of the glycerol oxidase in the composition is in the range of 10 to 10,000 units per kg flour. It will be appreciated that this indication of the amount of enzyme implies that a recommended appropriate amount of the composition will result in the above stated amount in the dough to which it is added. In specific embodiments, the amount of glycerol oxidase is in the range of 10 to 5,000 units such as 10 to 2,500 units per kg of flour. In other useful embodiments, the amount is in the range of 20 to 1,500 units per kg of flour.

In another embodiment, the dough improving composition may further comprises a lipase as defined above and in the amounts as also described above in relation to the method according to the invention.

Optionally, the composition is in the form of a complete dough additive mixture or pre-mixture for making a particular finished product and containing all of the dry ingredients and additives for such a dough. In specific embodiments, the composition is one particularly useful for preparing a baking product or in the making of a noodle product or an alimentary paste product.

In one advantageous embodiment of the above method at least one further enzyme is added to the dough. Suitable examples hereof include a cellulase, a hemicellulase, a xylanase, a starch degrading enzyme, hexose oxidase and a protease.

In a preferred advantageous embodiment, the further added enzyme is a lipase. It has been found that in accordance with the above method, the crumb homogeneity and specific volume of the bakery product can be increased significantly as compared to that of an otherwise similar bakery product prepared from a dough not containing glycerol oxidase, and from a similar bakery product prepared from a dough containing glycerol oxidase.

In a still further aspect, the present invention pertains to the use of a glycerol oxidase and a lipase in combination for improving the rheological properties of a flour dough and the quality of the finished product made from the dough.

In this connection, specific embodiments include use wherein the improvement of the rheological properties of the dough include that the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough that does not contain glycerol oxidase and use wherein the improvement of the quality of the finished product made from the dough is that the average pore diameter of the crumb of the bread made from the dough is reduced by at least 10%, relative to a bread which is made from a bread dough without addition of the lipase.

In a further embodiment, the use according to the invention, implies that the improvement of the quality of the finished product made from the dough consists in that the pore homogeneity of the crumb of the bread made from the dough is increased by at least 5%, relative to a bread which is made from a bread dough without addition of the lipase. The pore homogeneity of bread is conveniently measured by means of an image analyzer composed of a standard CCD-video camera, a video digitiser and a personal computer with WinGrain software. Using such an analyzer, the results of pore diameter in mm and pore homogeneity can be calculated as an average of measurements from 10 slices of bread. The pore homogeneity is expressed in % of pores that are larger than 0.5 times the average of pore diameter and smaller than 2 times the average diameter.

In a further embodiment, the use relates to improvement of the rheological characteristics of the dough including that the gluten index (as defined hereinbelow) in the dough is increased by at least 5%, relative to a dough without addition of a lipase, the gluten index is determined by means of a Glutomatic 2200 apparatus.

BRIEF DESCRIPTION OF THE FIGURES

The present invention is further illustrated by reference to the accompanying figures in which.

Figure 1:
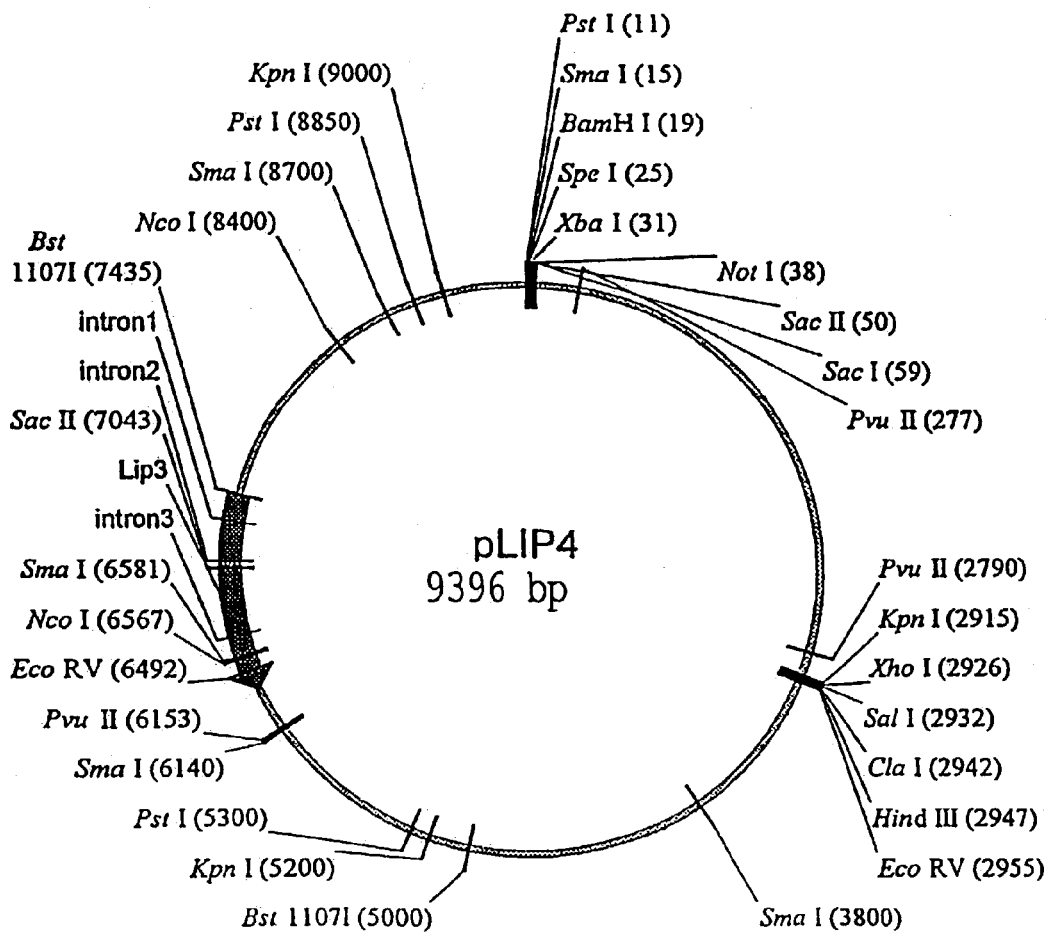
FIG. 1 shows the restriction map of the genomic clone of the lipA gene.
Figure 2:
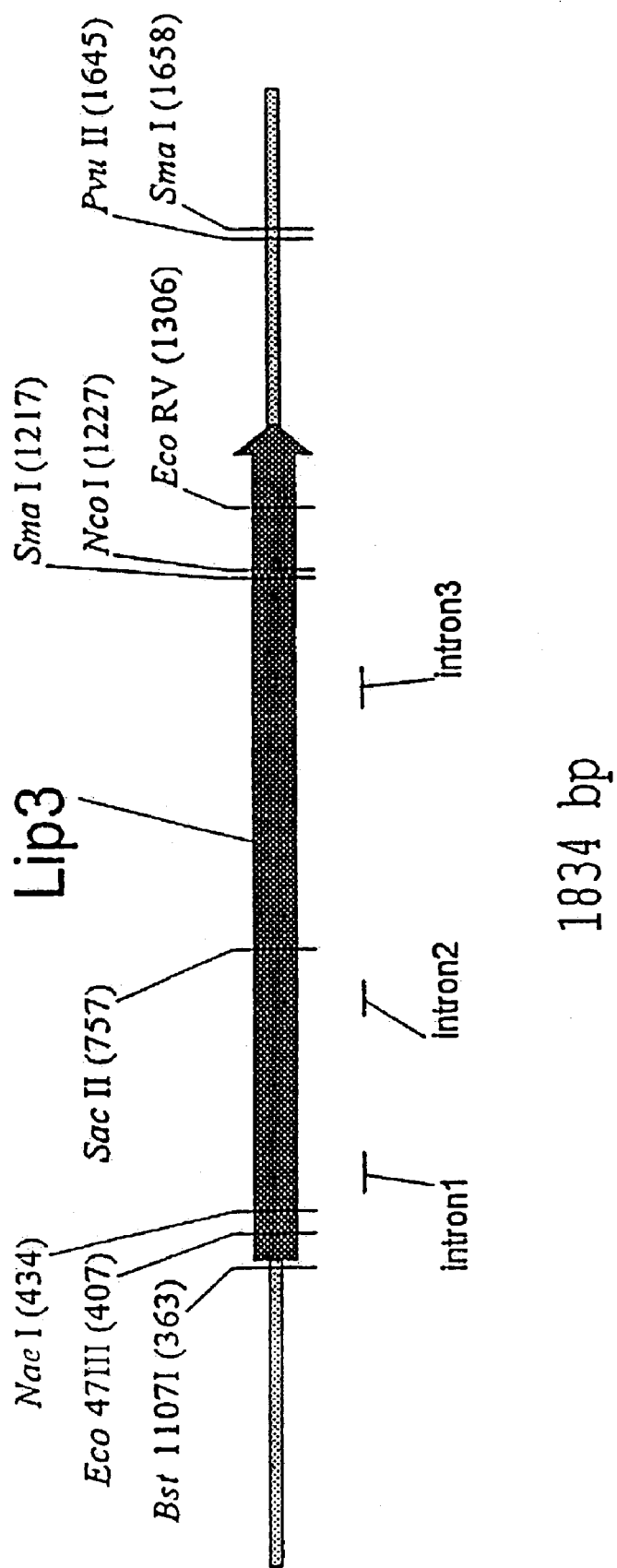
FIG. 2 shows the structure of the lipA gene encoding lipase 3.

The invention will now be described by way of illustration in the following non-limiting examples.

A. Production and Purification of Glycerol Oxidase (GLOX)

EXAMPLE 1

Production, Extraction and Purification of Glycerol Oxidase Using Different Strains and Cultivation Conditions 1. Production, Extraction and Purification of Glycerol Oxidase Using *Aspergillus japonicus* ATCC 1042 Cultivated in a Production Medium Containing 3% Glycerol The following assay for determination of glycerol oxidase activity was used:

The assay is based on the method described by Sullivan and Ikawa (Biochimica and Biophysica Acta, 1973, 309:11-22), but modified as described in the following. An assay mixture containing 150 µl 2% glycerol (in 100 mM phosphate buffer, pH 7.0), 120 µl 100 mM phosphate buffer, pH 7.0, 10 µl o-dianisidin dihydrochloride (Sigma D 3252, 3 mg/ml in H$_2$O), 10 µl peroxidase (POD) (Sigma P8125, 0.1 mg/ml in 100 mM phosphate buffer, pH 7.0) and 10 µl glycerol oxidase (GLOX) solution. The controls are made by adding buffer in place of GLOX solution. The incubation is started by the addition of glycerol. After 15 minutes of incubation at 25° C. in microtiter plates, the absorbance at 402 nm is read in a Elisa reader. A standard curve is constructed using varying concentrations of H$_2$O$_2$ in place of the enzyme solution. The reaction can be described in the following manner:

Oxidised o-dianisidine has a yellow colour absorbing at 402 nm.

One glycerol oxidase unit (U) is the amount of enzyme which catalyses the production of 1 µmole H$_2$O$_2$ per minute at 25° C., pH 7.0 at a substrate concentration of 0.2 M glycerol.

A spore suspension of *Aspergillus japonicus* ATCC 1042 was prepared by incubating *A. japonicus* on PDA medium (30° C., 7 days) and washing with 10 ml of 0.2% Tween 80. A preculture was prepared by inoculating 1 ml of the resulting spore suspension in 300 ml production medium containing 3.0% of glycerol (87%, Merck), 0.3% of yeast extract (Difco), 0.1% of meat extract (Difco), 0.1% KH$_2$PO$_4$ (Merck), 0.1% of MGSO$_4$*7H$_2$O (Merck), 0.1% antifoam (Contra spum) and 70 mg/l of chloramphenicolum (Mecobenzon) (pH adjusted to 7.2 with NaOH) in a 500 ml flask. The preculture was incubated overnight at 30° C. with shaking (200 rpm)

A 30 litre fermenter with 15 litre production medium was inoculated with 900 ml (corresponding to 3 flasks) of the resulting overnight preculture, and cultured at 30° C. for 25, hours under continuous stirring (350 rpm) and aeration (15 l/min). After culturing, the mycelia was harvested from the resulting culture broth by filtration on a Whatman GF/B filter by suction, and washed with 3 litres of deionized water. The mycelium yield was 186 g (wet weight).

A part (50 g) of the resulting mycelial mat was suspended in 700 ml of 50 mM borate buffer (pH 10.0), and disrupted by ultrasonication (Branson, Sonifer 250) at 5° C. (3×5 minutes). After disruption, the mycelia was removed by centrifugation (29,000 g for 15 minutes), the cell-free extract (700 ml) was brought to 40% saturation with ammonium sulfate and the resulting precipitate was removed by centrifugation (29,000 g for 20 minutes). The ammonium sulfate concentration was then increased to 70% saturation to precipitate the enzyme. The resulting precipitate was collected and solubilized in 100 ml of 50 mM borate buffer (pH 10.0). The crude extract was then dialysed for 24 hours against 5 l of 50 mM borate buffer (pH 10.0). After dialysis the insoluble matters in the crude extract were removed by centrifugation (18,000×g for 10 minutes). The resulting supernatant contained 8.7 units of glycerol oxidase activity per ml.

2. Production, Extraction and Purification of Glycerol Oxidase Using *Aspergillus japonicus* ATCC 1042 Cultivated in a Production Medium Containing 5% Glycerol A spore suspension of *Aspergillus japonicus* ATCC 1042 was prepared as described above. A preculture was prepared by inoculating 1 ml of the resulting spore suspension into a flask (500 ml) containing 200 ml production medium (5.0% glycerol, 0.25% yeast extract, 0.1% Malt extract, 0.7% antifoam (Contra spum), pH adjusted to 6.2 with HCl, sterilization at 121° C. for 90 minutes). The preculture was incubated 3 days at 30° C. with continuous shaking (200 rpm).

A 6 litre fermenter with 5 litre production medium as described above was inoculated with 50 ml of the resulting preculture and cultured at 30° C. for 3 days under continuous stirring (250 rpm) and aeration (5 l/min). After culturing the mycelia was harvested from the resulting culture broth by filtration on a Whatman GF/B filter by suction, and washed with 3 litre ionized water containing 0.9% NaCl.

The resulting mycelia mat was frozen in liquid nitrogen, suspended in 200 ml of 50 mM phosphate buffer (pH 7.0) and disrupted by ultrasonication (Branson, Sonifer 250) at 5° C. (4 minutes). After disruption, the mycelia was removed by filtration on a Whatman GF/A filter by suction. The enzyme in the resulting filtrate was concentrated on a AMICON® 8400 ultrafiltration unit and contained 87 units of glycerol oxidase per ml after ultrafiltration.

3. Production, Extraction and Purification of Glycerol Oxidase Using *Aspergillus japonicus* ATCC 1042 Cultivated in a Production Medium Containing 10% Glycerol A spore suspension of *Aspergillus japonicus* ATCC 1042 was prepared as described above. A 1 ml sample of the resulting spore suspension was inoculated into each of 5 flasks (500 ml) with 200 ml production medium containing 10.0% of glycerol, 0.1% of yeast extract and 0.1% of malt extract (pH adjusted to 6.2 with HCl, sterilization at 121° C. for 15 minutes). The cultures were incubated for 5 days at 30° C. with shaking (140 rpm).

The extraction and concentration of the enzyme was carried out as described above. The resulting filtrate contained 66 units of glycerol oxidase per ml after ultrafiltration.

4. Production of Glycerol Oxidase from *Penicillium Funiculosum* and *Penicillium Janthinellum*

Spore suspensions of *Penicillium funiculosum* NRRL 1132 and *Penicillium janthinellum* NRRL 2016 were prepared as described above. A 1 ml sample of each of the resulting spore suspensions was inoculated into separate flasks (1000 ml) containing 100 g wheat bran and 100 ml water (two flasks for each culture)

Glycerol oxidase was extracted by suspending the wheat bran cultures in 900 ml of 30 mM phosphate buffer (pH 6.5) containing 0.1% Triton X100 (Merck). The mycelial mat was removed from the cultivation media by filtration using a Whatman GF/B filter. The resulting mycelia mat was frozen in liquid nitrogen, suspended in 200 ml of 50 mM phosphate buffer (pH 7.0) and disrupted by ultrasonication (Branson, Sonifer 250) at 5° C. (4 minutes). After disruption, the mycelia was removed by filtration on a Whatman GF/A filter by suction. The resulting filtrate from the *Penicillium funiculosum* culture contained 7.4 units of glycerol oxidase per ml, and the resulting filtrate from the *Penicillium janthinellum* culture contained 11.3 units of glycerol oxidase per ml.

B. Production, Purification and Characterization of *Aspergillus Tubigensis* Lipase 3

Materials and Methods (i) Determination of Lipase Activity and Protein b 1. Plate Assay on Tributyrin-Containing Medium The assay is modified from Kouker and Jaeger (Appl. Environ. Microbiol., 1987, 53:211-213).

A typical protocol for this assay is as follows: 100 ml 2% agar in 50 mM sodium phosphate buffer (pH 6.3) is heated to boiling, and after cooling to about 70° C. under stirring, 5 ml 0.2% Rhodamine B is added under stirring plus 40 ml of tributyrin. The stirring is continued for 2 minutes. The mixture is then sonicated for 1 minute. After an additional 2 minutes of stirring, 20 ml of the agar mixture is poured into individual petri dishes. In the absence of lipase activity, the agar plates containing tributyrin and Rhodamine B will appear opaque and are pink coloured.

To quantify lipase activity, holes having a diameter of 3 mm are punched in the above agar and filled with 10 µl of lipase preparation. The plates are incubated for varying times at 37° C. When lipase activity is present in the applied preparation to be tested, a sharp pink/reddish zone is formed around the holes. When the plates are irradiated with UV light at 350 nm, the lipase activity is observed as halos of orange coloured fluorescence.

2. Modified Food Chemical Codex Assay for Lipase Activity

Lipase activity based on hydrolysis of tributyrin is measured according to Food Chemical Codex, Forth Edition, National Academy Press, 1996, p. 803. With the modification that the pH is 5.5 instead of 7. One LUT (lipase unit tributyrin) is defined as the amount of enzyme which can release 2 µmol butyric acid per min. under the above assay conditions.

3. p-nitrophenyl Acetate Assay

Lipase activity can also be determined colorimetrically using p-nitrophenyl acetate as a substrate e.g. using the following protocol: In a microtiter plate 10 µl of sample or blank is added followed by the addition of 250 µl substrate (0.5 mg p-nitrophenyl acetate per ml 50 mM phosphate buffer, pH 6.0).

The microtiter plate is incubated for 5 minutes at 30° C. and the absorbance at 405 nm is read using a microplate reader. 1 unit is defined as 1 µmol p-nitrophenol released per 5 minutes.

4. p-nitrophenyl Hexanoate Assay

Lipase activity can be determined by using p-nitrophenyl hexanoate as a substrate. This assay is carried out by adding 10 µl of sample preparation or blank to a microtiter plate followed by the addition of 250 µl substrate (0.5 mg p-nitrophenyl hexanoate per ml of 20 mM phosphate buffer, pH 6.). At this concentration of substrate the reaction mixture appears as a milky solution. The microtiter plate is incubated for 5 minutes at 30° C. and the absorbance at 405 nm is read in a microplate reader.

5. Titrimetric Assay of Lipase Activity

Alternatively, lipase activity is determined according to Food Chemical Codex (3rd Ed., 1981, pp 492-493) modified to sunflower-oil and pH 5.5 instead of olive oil and pH 6.5. The lipase activity is measured as LUS (lipase units sunflower) where 1 LUS is defined as the quantity of enzyme which can release 1 µmol of fatty acids per minute from sunflower oil under the above assay conditions.

6. Protein Measurement

During the course of purification of lipase as described in the following, the protein eluted from the columns was measured by determining absorbance at 280 nm. The protein in the pooled samples was determined in microtiter plates by a sensitive Bradford method according to Bio-Rad (Bio-Rad Bulletin 1177 EG, 1984). Bovine serum albumin was used as a standard.

EXAMPLE 2

Production, Purification and Characterization of Lipase 3

2.1. Production

A mutant strain of *Aspergillus tubigensis* was selected and used for the production of wild type lipase. This lipase is referred to herein as lipase 3. The strain was subjected to a fermentation in a 750 l fermenter containing 410.0 kg of tap water, 10.8 kg soy flour, 11.1 kg ammonium monohydrogenphosphate, 4.0 kg phosphoric acid (75%), 2.7 kg magnesium sulfate, 10.8 kg sunflower oil and 1.7 kg antifoam 1510. The substrate was heat treated at 121° C. for 45 minutes. The culture media was inoculated directly with $7.5 \times 10^9$ spores of the mutant strain. The strain was cultivated for three days at 38° C., pH controlled at 6.5, aeration at 290 l/min and stirring at 180 rpm the first two days and at 360 rpm the last day. The fermentate was separated using a drum filter and the culture filtrate was concentrated 3.8 times by ultrafiltration. The concentrated filtrate was preserved with potassium sorbate (0.1%) and sodium benzoate (0.2%) and used as a starting material for purification of lipase.

2.2. Purification of Lipase

A 60 ml sample of ferment (cf. 2.1) containing 557 LUS/ml, pH 5.5 was first filtered through a GF/B filter and subsequently through a 0.45 µm filter. The filtered sample was desalted using a Superdex G25 SP column (430 ml, 22×5 cm) equilibrated in 20 mM triethanolamine, pH 7.3. The flow rate was 5 ml/min. The total volume after desalting was 150 ml.

The desalted sample was applied to a Source Q30 anion exchanger column (100 ml, 5×5 cm) equilibrated in 20 mM triethanolamine, pH 7.3. The column was washed with equilibration buffer until a stable baseline was obtained.

Lipase activity was eluted with a 420 ml linear gradient from 0 to 0.35 M sodium chloride in equilibration buffer, flow rate 5 ml/min. Fractions of 10 ml were collected. Sodium acetate (100 µl of a 2M solution) was added to each fraction to adjust pH to 5.5. Fractions 26-32 (70 ml) were pooled.

To the pool from the anion exchange step was added ammonium sulfate to 1 M and the sample was applied to a Source Phenyl HIC column (20 ml, 10×2 cm) equilibrated in 20 mM sodium acetate (pH 5.5), 1 M ammonium sulfate. The column was washed with the equilibration buffer. Lipase was eluted with a 320 ml linear gradient from 1 M to 0 M ammonium sulfate in 20 mM sodium acetate (pH 5.5), flow 1.5 ml/min. Fractions of 7.5 ml were collected.

Fractions 33-41 were analyzed by SDS-PAGE using a NOVEX system with precast gels. Both electrophoresis and silver staining of the gels were done according to the manufacturer (Novex, San Diego, USA). (The same system was used for native electrophoresis and isoelectric focusing). It was found that fraction 40 and 41 contained lipase as the only protein.

2.3. Characterization of the Purified Lipase (i) Determination of Molecular Weight The apparent molecular weight of the native lipase was 37.7 kDa as measured by the above SDS-PAGE procedure. The purified lipase eluted at a molecular weight of 32.2 kDa from a Superose 12 gel filtration column (50 mM sodium phosphate, 0.2 M sodium chloride, pH 6.85, flow 0.65 ml/min) and is therefore a monomer.

The molecular weight of the lipase was also determined by matrix-assisted laser desorption ionisation (MALDI) by means of a time-of-flight (TOF) mass spectrometer (Voyager BioSpectrometry Workstation, Perspective Biosystems). Samples were prepared by mixing 0.7 µl of desalted lipase solution and 0.7 µl of a matrix solution containing sinapic acid (3.5dimethoxy-4-hydroxy cinnamic acid) in 70% acetonitrile (0.1% TFA, 10 mg/ml). 0.7 µl of the sample mixture was placed on top of a stainless steel probe tip and allowed to air-dry prior to introduction into the mass spectrometer. Spectra were obtained from at least 100 laser shots and averaged to obtain a good signal to noise ratio. The molecular mass for the lipase was found to be 30,384 Da and 30,310 Da by two independent analyses.

Digestion of the lipase with endo-β-N-acetyl-glucosamidase H (10 µl) from *Streptomyces* (Sigma) was carried out by adding 200 µl lipase and incubating at 37° C. for 2 hours. The digestion mixture was desalted using a VSWP filter and analyzed directly by MALDI mass spectrometry. A major component of deglycosylated lipase gave a mass of 29,339 Da and 29,333 Da by two independent analyses. A minor component with a mass of 29,508 Da was also observed. These values corresponds well to the later calculated theoretical value of 28,939 Da based on the complete amino acid sequence of the mature lipase.

(ii) Determination of the Isoelectric Point

The isoelectric point (pI) for the lipase was determined by isoelectric focusing and was found to be 4.1.

A calculation of the pI based on the amino acid sequence as determined in the following and shown as SEQ ID NO: 9 gave an estimated pI of 4.07.

(iii) Determination of Temperature Stability

Eppendorf tubes with 25 µl of purified lipase 3 plus 50 µl 100 mM sodium acetate buffer (pH 5.0) were incubated for 1 hour in a water bath at respectively 30, 40, 50, and 60° C. A control was treated in the same way, but left at room temperature. After 1 hour the lipase 3 activity was determined by the p-nitrophenyl acetate assay as described above.

The purified lipase had a good thermostability. It was found that the lipase maintained 60% of its activity after 1 hour at 60° C. 80% and 85% activity was maintained after 1 hour at 50° C. and 40° C. respectively.

(iv) Determination of pH Stability

Purified lipase 3 (200 µl) was added to 5 ml of 50 mM buffer solutions: (sodium phosphate, pH 8.0, 7.0 and 6.0 and sodium acetate pH 5.0, 4.0 and 3.5). The control was diluted in 5 ml of 4 mM sodium acetate pH 5.5. After four days at room temperature the residual activity was measured by the Modified Food Chemical Codex assay for lipase activity as described above. The lipase was very stable in the pH range from 4.0 to 7.0 where it maintained about 100% activity relative to the control (Table 2.1). At pH 3.5 the lipase maintained 92% activity, and at pH 8.0 95% residual activity was maintained as compared to the control.

TABLE 2.1 pH stability of lipase 3

| pH | Activity (LUT/ml) | Activity (%) |
|---|---|---|
| Control (pH 5.5) | 89.2 | 100 |
| 3.5 | 82.5 | 92 |
| 4.0 | 91.7 | 103 |
| 5.0 | 86.5 | 97 |
| 6.0 | 92.4 | 104 |
| 7.0 | 90.6 | 102 |
| 8.0 | 84.4 | 95 |

EXAMPLE 3

Amino Acid Sequencing of Lipase 3

Purified lipase enzyme was freeze-dried and 100 µg of the freeze-dried material was dissolved in 50 µl of a mixture of 8 M urea and 0.4 M ammonium hydrogencarbonate, pH 8.4. The dissolved protein was denatured and reduced for 15 minutes at 50° C. following overlay with nitrogen and addition of 5 µl 45 mM dithiothreitol. After cooling to room temperature, 5 µl of 100 mM iodoacetamide was added for the cysteine residues to be derivatized for 15 minutes at room temperature in the dark under nitrogen.

135 µl of water and 5 µg of endoproteinase Lys-C in 5 µl of water was added to the above reaction mixture and the digestion was carried out at 37° C. under nitrogen for 24 hours. The resulting peptides were separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides were rechromatographed on a Develosil C18 column (0.46×10 cm, Novo Nordisk, Bagsverd, Denmark) using the same solvent system, prior to N-terminal sequencing. Sequencing was done using an Applied Biosystems 476A sequencer using pulsed-liquid fast cycles according to the manufacturer's instructions (Applied Biosystems, California, USA).

For direct N-terminal sequencing, the purified protein was passed through a:Brownlee C2 Aquapore column (0.46×3 cm, 7 µm, Applied Biosystems, California, USA) using the same solvent system as above. N-terminal sequencing was then performed as described above. As the protein was not derivatized prior to sequencing, cysteine residues could not be determined.

The following peptide sequences were found:

```
N-terminal:          Ser-Val-Ser-Thr-Ser-Thr-Leu-Asp-Glu-  (SEQ ID NO:1)
                     Leu-Gln-Leu-Phe-Ala-Gln-Trp-Ser-Ala-
                     Ala-Ala-Tyr-X-Ser-Asn-Asn Internal peptide 1:  Val-His-Thr-Gly-Phe-Trp-Lys           (SEQ ID NO:2)

Internal peptide 2:  Ala-Trp-Glu-Ser-Ala-Ala-Asp-Glu-Leu-  (SEQ ID NO:3)
                     Thr-Ser-Lys-Ile-Lys
```

No further peptides could be purified from the HPLC fractionation presumably because they were very hydrophobic and therefore tightly bound to the reverse phase column.

A search in SWISS-PROT database release 31 for amino acid sequences with homology to the above peptides was performed and only three sequences were found.

(Boel et al., Lipids, 1988, 23:701-706) and *Penicillium camenbertii* (Yamaguchi et al., Gene, 1991, 103:61-67; Isobe and Nokihara, Febs. Lett., 1993, 320:101-106) respectively. Although the homology was not very high it was possible to position the lipase 3 peptides on these sequences as it is shown in the below Table 3.1.

TABLE 3.1

Alignment of lipase 3 peptides with known lipase sequences

```
LIP_RHIDL (SEQ ID NO: 10)  MVSFISISQGVSLCLLVSSMMLGSSAVPVSGKSGSSNTAVSASDNAALPP  50
LIP_RHIMI (SEQ ID NO: 11)  MVLKQRANYLGFLIVFFTAFLV--EAVPIKRQSNSTVDS--------LLP  40
MDLA_PENCA (SEQ ID NO: 12) MRLS-----------FFTAL-----------------SAVASLGYALPG  21
N-Terminal                 SVSTSTLDELQLFAQWSAAAYXSNN (SEQ ID NO: 20)

LIP_RHIDL    LISSRCAPPSNKGSKSDLQAEPYNMQKNTEWYESHGGNLTSIGKRDDNLV  100
LIP_RHIMI    LIPSRTSAPSSSPSTTDPEAPAM----------SRNGPLPS----DVETK  76
MDLA_PENCA   KLQSR------DVSTSELDQFEFWVQYAAASY------------------  47
             .**          . *... ..

LIP_RHIDL    GGMTLDLPSDAPPISLSSSTNSASDGGKVVAATTAQIQEFTKYAGIAATA  150
LIP_RHIMI    YGMALNATSYPDSV-----VQAMSIDGGIRAATSQEINELTYYTTLSANS  121
MDLA_PENCA   -------------------------------------YEADYTAQVGDKL  60

LIP_RHIDL    YCRSVVPGNKWDCVQCQKWVPDGKIITTFT-SLLSDTNGYVLRSDKQKTI  199
LIP_RHIMI    YCRTVIPGATWDCIHCDA-TEDLKIIKTWS-TLIYDTNAMVARGDSEKTI  169
MDLA_PENCA   SCSKG------NCPEVEA--TGATVSYDFSDSTITDTAGYIAVDHTNSAV  102

Peptide 1                      VHTGFWK (SEQ ID NO: 2)
Peptide 2                             AWESAADELTSK (SEQ ID NO: 19)

LIP_RHIDL    YLVFRGTNSFRSAITDIVFNFSDYKPVKGAKVHAGFLSSYEQVVNDYFPV  249
LIP_RHIMI    YIVFRGSSSIRNWIADLTFVPVSYPPVSGTKVHKGFLDSYGEVQNELVAT  219
MDLA_PENCA   VLAFRGSYSVRNWVADATFVHTNPGLCDGCLAELGFWSSWKLVRDDIIKE  152
             ..***. * *.  ..*  .*  . .     ..*  .. **  ...  . .

Peptide 2    IK

LIP_RHIDL    VQEQLTAHPTYKVIVTGHSLGGAQALLAGMDLYQREPRLSPKNLSIFTVG  299
LIP_RHIMI    VLDQFKQYPSYKVAVTGHSLGGATALLCALDLYQREEGLSSSNLFLYTQG  269
MDLA_PENCA   LKEVVAQNPNYELVVVGHSLGAAVATLAATDL--RGKGYPSAKLYAYA--  198
             . .  . *.*.. *.*****.* * *   **  *.  ...  .*   ..

LIP_RHIDL    GPRVGNPTFAYYVESTGPFQRTVHKRDIVPHVPPQSFGFLHPGESWIK   349
LIP_RHIMI    QPRVGDPAFANYVVSTGIPYRRTVNERDIVPHLPPAAFGFLHAGEEYWIT  319
MDLA_PENCA   SPRVGNAALAKYITAQGNNF-RFTHTNDPVPKLPLLSMGYVHVSPEYWIT  247
             ****....* *. *    . *  ....* **..*   ..*..*  * **.

LIP_RHIDL    SGTSN-V-----QICTSEIETKDCSNSIVPFTSILD-HLSYF-DINEGSC  391
LIP_RHIMI    DNSPETV-----QVCTSDLETSDCSNSIVPFTSVLD-HLSYF-GINTGLC  362
MDLA_PENCA   SPNNATVSTSDIKVIDGDVSFDGNTGTGLPLLTDFEAHIWYFVQVDAGKG  297

LIP_RHIDL    -------L      392
LIP_RHIMI    -------T      363
MDLA_PENCA   PGLPFKRV      305
```

All of the above peptides showed a low homology to the above known sequences. Especially internal peptide 2 has very low homology to the three lipases, LIP-RHIDL, LIP-RHIMI and MDLA-PENCA from *Rhizopus delamar* (Haas and Berka, Gene, 1991, 109:107-113), *Rhizomucor miehei*

EXAMPLE 4

Isolation and Purification of *Aspergillus tubigensis* Genomic DNA

The *Aspergillus tubigensis* mutant strain was grown in PDB (Difco) for 72 hours and the mycelium was harvested.

0.5-1 g of mycelium was frozen in liquid nitrogen and ground in a mortar. Following evaporation of the nitrogen, the ground mycelium was mixed with 15 ml of an extraction buffer (100 mM Tris.HCl, pH 8.0, 50 mM EDTA, 500 mM NaCl, 10 mM β-mercaptoethanol) and 1 ml 20% sodium dodecylsulfate. The mixture was vigorously mixed and incubated at 65° C. for 10 min. 5 ml 3M potassium acetate, (pH 5.1 adjusted with glacial acetic acid) was added and the mixture further incubated on ice for 20 min. The cellular debris was removed by centrifugation for 20 min. at 20,000×g and 10 ml isopropanol was added to the supernatant to precipitate (30 min at −20° C.) the extracted DNA. After further centrifugation for 15 min at 20,000×g, the DNA pellet was dissolved in 1 ml TE (10 mM Tris-HCl pH 8.0, 1 mM EDTA) and precipitated again by addition of 0.1 ml 3 M NaAc, pH 4.8 and 2.5 ml ethanol. After centrifugation for 15 min at 20,000×g the DNA pellet was washed with 1 ml 70% ethanol and dried under vacuum. Finally, the DNA was dissolved in 200 µl TE and stored at −20° C.

EXAMPLE 5

The Generation of a Fragment of the Putative Gene Coding for Lipase 3 Using PCR

To obtain a fragment of the putative gene (in the following referred to as the lipA gene) as a tag to isolate the complete gene, a PCR amplification procedure based on the information in the isolated peptide sequences was carried out.

Degenerated primers for PCR amplification of a fragment of the lipase gene were designed based on the amino acid sequence of the isolated peptides. The following three PCR primers were synthesized:
C035: TTC CAR YTN TTY GCN CAR TGG (SEQ ID NO: 5) 18 mer 256 mixture, based on the N-terminal sequence QLFAQW. (SEQ ID NO: 21)
C037: GCV GCH SWY TCC CAV GC (SEQ ID NO: 6) 17 mer 216 mixture, based on internal peptide 2 sequence AWESAA (reversed). (SEO ID NO: 22)

The oligonucleotides were synthesised on a Applied Biosystems model 392 DNA/RNA Synthesizer. To reduce the degree of degeneracy the rare Ala codon GCA and the Ser codon TCA have been excluded in design of primer C037.

With these primers the desired fragments were amplified by PCR. Using these primers it was expected that a fragment of about 300 bp should be amplified provided there are no introns in the fragment.

The following PCR reactions were set up in 0.5 ml PCR tubes to amplify a putative lipA fragment:
1. 0.5 µg total genomic DNA,
    100 pmol primer C036,
    100 µmol primer C037,
    10 µl PCR Buffer II (Perkin Elmer),
    6 µl 25 mM MgCl$_2$,
    2 µl dNTP mix (10 mM dATP, 10 mM dCTP, 10 mM dGTP, 10 mM dTT
    2 units Amplitaq polymerase (Perkin Elmer), and water to a total volume of 100 µl.
2. 0.5 µg total genomic DNA,
    100 pmol primer C035,
    100 pmol primer C036,
    10 µl PCR Buffer II (Perkin Elmer),
    6 µl 25 mM MgCl$_2$,
    2 µl dNTP mix (10 mM DATP, 10 mM dCTP, 10 mM dGTP, 10 mM dTT
    2 units Amplitaq polymerase (Perkin Elmer), and water to a total volume of 100 µl.

The reactions were performed using the following program:

| | |
|---|---|
| 94° C. | 2 min |
| 94° C. | 1 min ) |
| 40° C. | 1 min ) |
| 72° C. | 1 min ) These three steps were repeated for 30 |
| 72° C. | 5 min cycles |
| 5° C. | SOAK |

The PCR amplifications were performed in a MJ Research Inc. PTC-100 Thermocycler.

In reaction 1, three distinct bands of about 300, 360 and 400 bp, respectively could be detected. These bands were isolated and cloned using the pT7-Blue-T-vector kit (Novagene). The sizes of these fragment is in agreement with the expected size provided that the fragment contains 0, 1 or 2 introns, respectively.

The three fragments were sequenced using a "Thermo Sekvenase fluorescent labelled primer cycle sequencing Kit" (Amersham) and analyzed on a ALF sequencer (Pharmacia) according to the instructions of the manufacturer. The fragment of about 360 bp contained a sequence that was identified as a lipase and, as it contained the part of the N-terminal distal to the sequence used for primer design, it was concluded that the desired lipA gene fragment was obtained.

The sequence of the about 360 bp PCR fragment (SEQ ID NO:7) is shown in the following Table 5.1. The peptide sequence used for primer design is underlined. The remaining part of the N-terminal sequence is doubly underlined.

TABLE 5.1

(SEQ ID NO: 13)PCR-generated putative lipA sequence
(The four amino acid fragments of table 5.1 are contained in
SEQ ID NOS: 14-17)

```
         10        20        30        40        50        60
tacccggggntccattCAGTTGTTCGCGCAATGGTCTGCCGCAGCTTATTGCTCGAATA
                Q  L  F  A  Q  W  S  A  A  A  Y  C  S  N 70        80        90       100       110       120
         ATATCGACTCGAAAGAVTCCAACTTGACATGCACGGCCAACGCCTGTCCATCAGTCGAGG
 N  I  D  S  K  X  S  N  L  T  C  T  A  N  A  C  P  S  V  E 130       140       150       160       170       180
         AGGCCAGTACCACGATGCTGCTGCTGGTGGAGTTCGACCTGTATGTCACTCAGATCGCAGACATAG
 E  A  S  T  T  M  L  L  E  F  D  L  Y  V  T  Q  I  A  D  I
```

TABLE 5.1-continued (SEQ ID NO: 13)PCR-generated putative lipA sequence
(The four amino acid fragments of table 5.1 are contained in
SEQ ID NOS: 14-17)

```
          190       200       210       220       230       240
AGCACAGCTAATTGAACAGGACGAACGACTTTTGGAGGCACAGCCGGTTTCCTGGCCGCG
  E  H  S  -  L  N  R  T  N  D  F  W  R  H  S  R  F  P  G  R 250       260       270       280       290       300
                G  Q  H  Q  Q  A  A  R  G  R  L  P  G  K  Q  H  D  -  E  L 310       320       330
ATTGCTAATCYTGACTTCATCCTGGRAGATAACG
  D  C  -  X  -  L  H  P  X  R  - (SEQ ID NO: 13)
```

The finding of this sequence permitted full identification of the PCR fragment as part of the lipA gene. The stop codon found in the reading frame can be caused either by a PCR or a reading error or there can be an intron encoded in the fragment as a consensus intron start and ending signal (shown in bold). If the putative intron is removed a shift in reading frame will occur. However, an alignment of the deduced amino acid sequence and the fungal lipases shown in Table 3.1 suggested that the fragment was part of the desired gene.

EXAMPLE 6

Cloning and Characterisation of the lipA Gene (i) Construction of an *Aspergillus tubigensis* Genomic Library

*Aspergillus tubigensis* genomic DNA was digested partially with Tsp5091 (New England Biolabs Inc.). 10 µg DNA was digested in 100 µl reaction mixture containing 2 units Tsp5091. After 5, 10, 15 and 20 minutes 25 µl was removed from the reaction mixture and the digestion was stopped by addition of 1 µl 0.5 M EDTA, pH 8.0. After all four reactions had been stopped, the samples were run on a 1% agarose gel in TAE buffer (10×TAE stock containing per litre: 48.4 g Trizma base, 11.5 ml glacial acetic acid, 20 ml 0.5 M EDTA pH 8.0). HindIII-digested phage Lambda DNA was used as molecular weight marker (DNA molecular weight marker II, Boehringer, Mannheim). Fragments of a size between about 5 and 10 kb were cut out of the gel and the DNA fragments were purified using Gene Clean II Kit (Bio-101 Inc.). The purified fragments were pooled and 100 ng of the pooled fragments were ligated into 1 µg EcoRI-digested and dephosphorylated ZAP II vector (Stratagene) in a total volume of 5 µl. 2 µl of this volume was packed with Gigapack II packing extract (Stratagene) which gave a primary library of 650,000 pfu.

*E. coli* strain XL1-Blue-MRF (Stratagene) was infected with 5×50,000 pfu of the primary library. The infected bacteria were mixed with top agarose (as NZY plates but with 6 g agarose per litre instead of the agar) and plated on 5 NZY plates (13 cm). After incubation at 37° C. for 7 hours, 10 ml SM buffer (per litre: 5.8 g NaCl, 2.0 g MgCl$_2$.7H$_2$O, 50 ml 1 M Tris.HCl pH 7.5, 5.0 ml of 2% (w/v) gelatine) and incubated overnight at room temperature with gently shaking. The buffer containing washed-out phages was collected and pooled. 5% chloroform was added and after vigorous mixing the mixture was incubated 1 hour at room temperature. After centrifugation for 2 minutes at 10,000×g the upper phase containing the amplified library was collected and dimethylsulphoxide was added to 7%. Aliquots of the library was taken out in small tubes and frozen at −80° C. The frozen library contained 2.7×10$^9$ pfu/ml with about 6% without inserts.

(ii) Screening of the *Aspergillus tubigensis* Library

2×50.000 pfu were plated on large (22×22 cm) NZY plates containing a medium containing per litre: 5 g NaCl, 2 g MgSO$_4$.7H$_2$O, 5 g yeast extract, 10 g casein hydrolysatei 15 g agar, pH adjusted to 7.5 with NaOH. The medium was autoclaved and cooled to about 60° C. and poured into the plates. Per plate was used 240 ml of medium.

The inoculated NZY plates were incubated overnight at 37° C. and plaque lifts of the plates were made. Two lifts were made for each plate on Hybond N (Amersham) filters. The DNA was fixed using UV radiation for 3 min. and the filters were hybridized as described in the following using, as the probe, the above PCk fragment of about 360 bp that was labelled with $^{32}$P-dCTP using Ready-to-Go labeling kit (Pharmacia).

The filters were prehybridised for one hour at 65° C. in 25 ml prehybridisation buffer containing 6.25 ml 20×SSC (0.3 M Na$_3$citrate, 3 M NaCl), 1,25 ml 100×Denhard solution, 1.25 ml 10% SDS and 16.25 ml water. 150 µl 10 mg/ml denatured Salmon sperm DNA was added to the prehybridization buffer immediately before use. Following prehybridization, the prehybridisation buffer was discarded and the filters hybridised overnight at 65° C. in 25 ml prehybridisation buffer with the radiolabelled PCR fragment.

Next day the filters were washed according to the following procedure: 2×15 min. with 2×SSC+0.1% SDS, 15 min. with 1×SSC+0.1% SDS and 10 min. with 0.1×SSC+0.1% SDS.

All washes were done at 65° C. The sheets were autoradiographed for 16 hours and positive clones were isolated. A clone was reckoned as positive only if there was a hybridisation signal on both plaque lifts of the plate in question, Seven putative clones were isolated and four were purified by plating on small petri dishes and performing plaque lifts essentially as described above.

The purified clones were converted to plasmids using an ExAssist Kit (Stratagene).

Two sequencing primers were designed based on the about 360 bp PCR fragment. The sequencing primers were used to sequence the clones and a positive clone with the lipA gene encoding lipase 3 was found. The isolated positive clone was designated pLIP4.

(iii) Characterisation of the pLIP4 Clone

A restriction map of the clone was made. The above 360 bp PCR fragment contained a SacII site and as this site could be found in the genomic clone as well this site facilitated the construction of the map. The restriction map showing the structure of pLIP4 is shown in FIG. 1. The restriction map shows that the complete gene is present in the clone. Additionally, since promoter and terminator sequences are present, it was assumed that all the important regions is present in the clone.

A sample of *Escherichia coli* strain DH5α containing pLIP4 was deposited in accordance with the Budapest Treaty with The National Collections of Industrial and Marine Bacteria Limited (NCIMB) at 23 St. Machar Drive, Aberdeen, Scotland, United Kingdom, AB2 1RY on 24 Feb. 1997 under the accession number NCIMB 40863.

The gene was sequenced using cycle sequencing and conventional sequencing technology. The complete sequence (SEQ ID NO: 18) is shown below in Table 6.1. The sequence has been determined for both strands for the complete coding region and about 100 bp upstream and downstream of the coding region. The sequences downstream to the coding region have only been determined on one strand and contain a few uncertainties. In the sequence as shown below, the intron sequences are indicated as lowercase letters and the N-terminal and the two internal peptides (peptide 1 and peptide 2) are underlined:

TABLE 6.1

(SEQ ID NO: 18) The DNA sequence for the lipA gene and flanking sequences

```
   1  CCNDTTAATCCCCCACCGGGGTTCCCGCTCCCGGATGGAGATGGGGCCAAAACTGGCAAC

61  CCCCAGTTGCGCAACGGAACAACCGCCGACCCGGAACAAAGGATGCGGATGAGGAGATAC

121  GGTGCCTGATTGCATGGCTGGCTTCATCTGCTATCGTGACAGTGCTCTTTGGGTGAATAT

181  TGTTGTCTGACTTACCCCGCTTCTTGCTTTTTCCCCCCTGAGGCCCTGATGGGGAATCGC

241  GGTGGGTAATATGATATGGGTATAAAAGGGAGATCGGAGGTGCAGTTGGATTGAGGCAGT

301  GTGTGTGTGTGCATTGCAGAAGCCCGTTGGTCGCAAGGTTTTGGTCGCCTCGATTGTTTG

361  TATACCGCAAGATGTTCTCTGGACGGTTTGGAGTGCTTTTGACAGCGCTTGCTGCGCTGG
              M   F   S   G   R   F   G   V   L   L   T   A   L   A   A   L

421  GTGCTGCCGCGCCGGCACCGCTTGCTGTGCGGAgtaggtgtgcccgatgtgagatggttg
       G   A   A   A   P   A   P   L   A   V   R 481  gatagcactgatgaagggtgaatagGTGTCTCGACTTCCACGTTGGATGAGTTGCAATTG
                                 S   V   S   T   S   T   L   D   E   L   Q   L 541  TTCGCGCAATGGTCTGCCGCAGCTTATTGCTCGAATAATATCGACTCGAAAGACTCCAAC
       F   A   Q   W   S   A   A   A   Y   C   S   N   N   I   D   S   K   D   S   N

601  TTGACATGCACGGCCAACGCCTGTCCATCAGTCGAGGAGGCCAGTACCACGATGCTGCTG

GAGTTCGACCTgtatgtcactcagatcgcagacatagagcacagctaatttgaacagGAC
       E   F   D   L 721  GAACGACTTTGGAGGCACAGCCGGTTTCCTGGCCGCGGACAACACCAACAAGCGGCTCGT
       N   D   F   G   G   T   A   G   F   L   A   A   D   N   T   N   K   R   L   V 781  GGTCGCCTTCCGGGGAAGCAGCACGATTGAGAACTGGATTGCTAATCTTGACTTCATCCT
       V   A   F   R   G   S   S   T   I   E   N   W   I   A   N   L   D   F   I   L 841  GGAAGATAACGACGACCTCTGCACCGGCTGCAAGGTCCATACTGGTTTCTGGAAGGCATG
       E   D   N   D   D   L   C   T   G   C   K   V   H   T   G   F   W   K   A   W 901  GGAGTCCGCTGCCGACGAACTGACGAGCAAGATCAAGTCTGCGATGAGCACGTATTCGGG
       E   S   A   A   D   E   L   T   S   K   I   K   S   A   M   S   T   Y   S   G 961  CTATACCCTATACTTCACCGGGCACAGTTTGGGCGGCGCATTGGCTACGCTGGGAGCGAC
       Y   T   L   Y   F   T   G   H   S   L   G   G   A   L   A   T   L   G   A   T 1021  AGTTCTGCGAAATGACGGATATAGCGTTGAGCTGGTGAGTCCTTCACAAAGGTGATGGAG
       V   L   R   N   D   G   Y   S   V   E   L 1081  CGACAATCGGGAACAGACAGTCAATAGTACACCTATGGATGTCCTCGAATCGGAAACTAT
                                       Y   T   Y   G   C   P   R   I   G   N   Y 1141  GCGCTGGCTGAGCATATCACCAGTCAGGGATCTGGGGCCAACTTCCGTGTTACACACTTG
       A   L   A   E   H   I   T   S   Q   G   S   G   A   N   F   R   V   T   H   L 1201  AACGACATCGTCCCCCGGGTGCCACCCATGGACTTTGGATTCAGTCAGCCAAGTCCGGAA
       N   D   I   V   P   R   V   P   P   M   D   F   G   F   S   Q   P   S   P   E 1261  TACTGGATCACCAGTGGCAATGGAGCCAGTGTCACGGCGTCGGATATCGAAGTCATCGAG
       Y   W   I   T   S   G   N   G   A   S   V   T   A   S   D   I   E   V   I   E 1321  GGAATCAATTCAACGGCGGGAAATGCAGGCGAAGCAACGGTGAGCGTTGTGGCTCACTTG
       G   I   N   S   T   A   G   N   A   G   E   A   T   V   S   V   V   A   H   L
```

TABLE 6.1-continued (SEQ ID NO: 18) The DNA sequence for the lipA gene and flanking sequences

```
1381 TGGTACTTTTTTGCGATTTCCGAGTGCCTGCTATAACTAGACCGACTGTCAGATTAGTGG
      W  Y  F  F  A  I  S  E  C  L  L  -

1441 ACGGGAGAAGTGTACATAAGTAATTAGTATATAATCAGAGCAACCCAGTGGTGGTGATGG

1501 TGGTGAAAGAAGAAACACATTGAGTTCCCATTACGKAGCAGWTAAAGCACKTKKGGAGGC

1561 GCTGGTTCCTCCACTTGGCAGTTGGCGGCCATCAATCATCTTTCCTCTCCTTACTTTCGT

1621 CCACCACAACTCCCATCCTGCCAGCTGTCGCATCCCCGGGTTGCAACAACTATCGCCTCC

1681 GGGGCCTCCGTGGTTCTCCTATATTATTCCATCCGACGGCCGACGTTTCACCCTCAACCT

1741 GCGCCGCCGCAAAATCTCCCCGAGTCGGTCAACTCCCTCGAACCGCCGCCCGCATCGACC

1801 TCACGACCCCGACCGTCTGYGATYGTCCAACCG
```

(iv) Analysis of the Sequence of the Complete Gene

The peptide sequences obtained could all be found in the deduced amino acid sequence (see Table 5.1) which confirms again that the sequence found is the sequence of the lipase 3 gene. The gene was designated lipA.

The amino acid sequence was aligned with the three fungal lipases used to align the peptide sequences. The alignment is shown in Table 6.2.

TABLE 6.2

Alignment of the lipase 3 sequence with known fungal lipases

```
LIPASE 3    MFSG----------RFGVLL-----------------------TALAA   -15
MDLA_PENCA  MRLS----------FETAL-----------------------SAVAS   -14
LIP_RHIDL   MVSFISISQGVSLCLLVSSMMLGSSAVPVSGKSGSSNTAVSADNAALPP  -50
LIP_RHIMI   MVLKQRANYLGFLIVFFTAFLV--EAVPIKRQSNSTVDS--------LPP -40

LIPASE 3    L------------------------------------------------  -16
MDLA_PENCA  L------------------------------------------------  -15
LIP_RHIDL   LISSRCAPPSNKGSKSDLQAEPYNMQKNTEWYESHGGNLTSIGKRDDNLV -100
LIP_RHIMI   LIPSRTSAPSSSPSTTDPEAPAM----------SRNGPLPS----DVETK -76

LIPASE 3    --------GAAAPAPLA-----------VRSVSTSTLDELQLFAQWSAAA -47
MDLA_PENCA  --------GYALPGKLQ-----------SRDVSTSELDQFEFWVQYAAAS -46
LIP_RHIDL   GGMTLDLPSDAPPISLSSSTNSASDGGKVVAATTAQIQEFTKYAGIAATA -150
LIP_RHIMI   YGMALNATSYPDSV-----VQAMSIDGGIRAATSQEINELTYYTTLSANS -121

LIPASE 3    YCSNNIDSK-DSNLTCTANACPSVEEASTTMLLEFDLTNDFGGTAGFLAA -96
MDLA_PENCA  YYEADYTAQVGDKLSCSKGNCPEVEATGATVSYDFS-DSTITDTAGYIAV -95
LIP_RHIDL   YCRSVVP---GNKWDCVQ--CQKWVPDGKIIT---TFTSLLSDTNGYVLR -192
LIP_RHIMI   YCRTVIP---GATWDCIH--CDA-TEDLKIIK---TWSTLIYDTNAMVAR -162

LIPASE 3    DNTNKRLVVAFRGSSTIENWIANLDFILEDNDDLCTGCKVHTGFWKAWES -146
MDLA_PENCA  DHTNSAVVLAFRGSYSVRNWVADATFV-HTNPGLCDGCLAELGFWSSWKL -144
LIP_RHIDL   SDKQKTIYLVFRGTNSFRSAITDIVFNFSDYKPV-KGAKVHAGFLSSYEQ -241
LIP_RHIMI   GDSEKTIYIVFRGSSSIRNWIADLTFVPVSYPPV-SGTKVHKGFLDSYGE -211

LIPASE 3    AADELTSKIKSAMSTYSGYTLYFTGHSLGGALATLGATVL--RNDGY-SV -193
MDLA_PENCA  VRDDIIKELKEVVAQNPNYELVVVGHSLGAAVATLAATDL--RGKGYPSA -192
LIP_RHIDL   VVNDYFPVVQEQLTAHPTYKVIVTGHSLGGAQALLAGMDLYQREPRLSPK -291
LIP_RHIMI   VQNELVATVLDQFKQYPSYKVAVTGHSLGGATALLCALDLYQREEGLSSS -261

LIPASE 3    ELYTY--GCPRIGNYALAEHITSQGSGANFRVTHLNDIVPRVPPMDFGFS -241
MDLA_PENCA  KLYAY--ASPRVGNAALAKYITAQGN--NFRFTHTNDPVPKLPLLSMGYV -238
LIP_RHIDL   NLSIFTVGGPRVGNPTFAYYVESTGIPFQ-RTVHKRDIVPHVPPQSFGPL -340
LIP_RHIMI   NLFLYTQGQPRVGDPAFANYVVSTGIPYR-RTVNERDIVPHLPPAAFGFL -310

LIPASE 3    QPSPEYWITSGNGASVTASDIEVIEGINSTAGNAGEATVSVV---AHLWY -288
MDLA_PENCA  HVSPEYWITSPNNATVSTSDIKVIDGDVSFDGNTGTGLPLLTDFEAHIWY -288
LIP_RHIDL   HPGVESWIKSGTSN-VQICTSEIE------TKDCSNSIVPETSILDHLSY -383
LIP_RHIMI   HAGEEYWITDNSPETVQVCTSDLE------TSDCSNSIVPFTSVLDHLSY -354

LIPASE 3    FFAISECL--------L -297 (SEQ ID NO: 9)
MDLA_PENCA  FVQVDAGKGPGLPFKRV -305 (SEQ ID NO: 12)
```

TABLE 6.2-continued

Alignment of the lipase 3 sequence with known fungal lipases

```
LIP_RHIDL    F-DINEGSC-------L  -392  (SEQ ID NO: 10)
LIP_RHIMI    F-GINTGLC-------T  -363  (SEQ ID NO: 11)
             *   ...
```

The above alignment shows that lipase 3 is homologous to the known lipase sequences but that the homology is not very high. Deletions or insertions in the lipase 3 sequence was not observed when comparing the sequence with these three lipases. This strengthens the probability that the putative introns have been identified correctly.

A search in SWISS-PROT release 31 database was performed and it did not lead to further sequences with higher homology than that to the above known lipases (Table 6.3).

The sequence with highest homology is a mono-diacyl lipase from *Penicillium camembertii* where the identity is found to 42%. However the C-terminal of lipase 3 resembles the 2 lipases from Zygomycetes (*Rhizopus* and *Rhizomucor*) and not the *P. camembertii* enzyme.

TABLE 6.3

Alignment of coding sequence of the *lipA* gene and gene coding for mono-diacyl lipase from *Penicillium camemberti*

```
LIPASE 3      MFSGRFGVLLTALAALGAAAPAPLAVRSVSTSTLDELQLFAQWSAAAYCS     -50
              |   | | ||||| | | ||| ||       || |
MDLA_PENCA    MRLSFFTAL-SAVASLGYALPGKLQSRDVSTSELDQFEFWVQYAAASYYE     -49

LIPASE 3      NNIDSK-DSNLTCTANACPSVEEASTTMLLEFDLTNDFGGTAGFLAADNT     -99
                       |   | ||  |          ||| |||
MDLA_PENCA    ADYTAQVGDKLSCSKGNCPEVEATGATVSYDFS-DSTITDTAGYIAVDHT     -98

LIPASE 3      NKRLVVAFRGSSTIENWIANLDFILEDNDDLCTGCKVHTGFWKAWESAAD     -149
                | |||||   ||  |    | ||   |||   |
MDLA_PENCA    NSAVVLAFRGSYSVRNWVADATFV-HTNPGLCDGCLAELGFWSSWKLVRD     -147

LIPASE 3      ELTSKIKSAMSTYSGYTLYFTGHSLGGALATLGATVLRNDGY-SVELYTY     -198
                    |     ||  |||| ||| ||| || ||    || |
MDLA_PENCA    DIIKELKEVVAQNPNYELVVVGHSLGAAVATLAATDLRGKGYPSAKLYAY     -197

LIPASE 3      GCPRIGNYALAEHITSQGSGANFRVTHLNDIVPRVPPMDFGFSQPSPEYW     -248
              || ||| ||    ||| || ||   |    |  ||||| |
MDLA_PENCA    ASPRVGNAALAKYITAQGN--NFRFTHTNDPVPKLPLLSMGYVHVSPEYW     -245

LIPASE 3      ITSGNGASVTASDIEVIEGINSTAGNAGEATVSVV---AHLWYFFAISEC     -295
              |||| | ||| ||  | |        || ||
MDLA_PENCA    ITSPNNATVSTSDIKVIDGDVSFDGNTGTGLPLLTDTFEAHIWYFVQVDAG     -295

LIPASE 3      L--------L  -297  (SEQ ID NO: 9)

MDLA_PENCA    KGPGLPFKRV  -305  (SEQ ID NO: 12)
```

Identity: 126 amino acids (42.42%)

The N-terminal of the mature lipase has been determined by N-terminal sequencing to be the serine residue No. 28 of the lipase 3 precursor (SEQ ID NO:9) as shown in Table 6.4 below. Hence the amino acids No. 1 to No. 27 is the signal sequence.

TABLE 6.4

Amino acid sequence of the precursor of lipase 3 (SEQ ID NO: 9)

```
            5         10        15        20        25        30
            |         |         |         |         |         |
 1   M  F  S  G  R  F  G  V  L  L  T  A  L  A  A  L  G  A  A  A  P  A  P  L  A  V  R  S  V  S
```

TABLE 6.4-continued

Amino acid sequence of the precursor of lipase 3 (SEQ ID NO: 9)

```
 31 T S T L D E L Q L F A Q W S A A A Y C S N N I D S K D S N L
 61 T C T A N A C P S V E E A S T T M L L E F D L T N D F G G T
 91 A G F L A A D N T N K R L V V A F R G S S T I E N W I A N L
121 D F I L E D N D D L C T G C K V H T G F W K A W E S A A D E
151 L T S K I K S A M S T Y S G Y T L Y F T G H S L G G A L A T
181 L G A T V L R N D G Y S V E L Y T Y G C P R I G N Y A L A E
211 H I T S Q G S G A N F R V T H L N D I V P R V P P M D F G F
241 S Q P S P E Y W I T S G N G A S V T A S D I E V I E G I N S
271 T A G N A G E A T V S V V A H L W Y F F A I S E C L L
```

Number of residues: 297.

Residues 167-176 are recognised as a common motif for the serine lipases (PROSITE). The crystal structure for the *Rhizomucor miehei* serine lipase has been examined and the residues in the active site identified (Brady et al., Nature, 1990, 343:767-770; Derewanda et al., J. Mol. Biol., 1992, 227:818-839). The active site residues of *R. miehei* lipase have all been conserved in all the lipases and correspond to the following residues in lipase 3: serine 173, aspartic acid 228 and histidine 285.

Lipase 3 contains 7 cysteine residues. Four of these are conserved in the *P. camembertii* lipase where they form disulphide bonds (Isobe and Nokuhara, Gene, 1991, 103: 61-67). This corresponds to disulphide bonds between residue 62-67 and 131-134. In addition, two cysteine residues are homologous to two C residues which forms an additional disulphide bond in *Rhizopus* and *Rhizomucor* lipases corresponding to residues 49-295.

Two putative N-glycosylation sites were found in lipase 3 in position 59 and 269. Neither of these are conserved in the other fungal lipases.

EXAMPLE 7

Transformation of *Aspergillus tubigensis* and Overexpression of Lipase 3 in *A. tubigensis*

The protocol for transformation was based on the teachings of Buxton et al. (Gene, 1985, 37:207-214), Daboussi et al (Curr. Genet., 1989, 15:453-456) and Punt and van den Hondel, (Meth. Enzym., 1992, 216:447-457).

A multicopy lipA strain was produced by transforming the pLIP4 µl plasmid into *Aspergillus tubigensis* strain 6M 179 using cotransformation with a hygromycin resistant marker plasmid.

A screening procedure used to visualise fungal lipase after ultrathin layer isoelectric focusing was adapted to screen *Aspergillus tubigensis* transformants grown on agar plates. Screening of lipase producers on agar plates was done using 2% olive oil as the substrate for the enzyme (lipase) as well as the inducer for the lipase promoter. In addition, the plates contained a fluorescent dye, Rhodamine B. In the presence of olive oil, the transformants will be induced to secrete lipase. The lipase secreted into the agar plate will hydrolyse the olive oil causing the formation of orange fluorescent colonies that is visible upon UV radiation (350 nm). The appearence of fluorescent colonies was generally monitored after 24 hours of growth. After several days of growth, the lipase producing strains could be identified as orange fluorescent strains that are visible by eye. Under this plate screening condition, the untransformed strain gave no background fluorescence and appeared as opaque pink colonies.

Sixteen transformants that showed orange fluorescent halos were cultivated for 8 days in shake flasks containing 100 ml of minimal medium supplemented with 1% olive oil, 0.5% yeast extract and 0.2% casamino acids. The amount of lipase secreted was quantified by applying 10 µl of cell-free culture supernatant into holes punched in olive oil-Rhodamine B agar plates and incubating the plates overnight at 37° C. Five transformants with higher lipase production were found.

Figure 3:
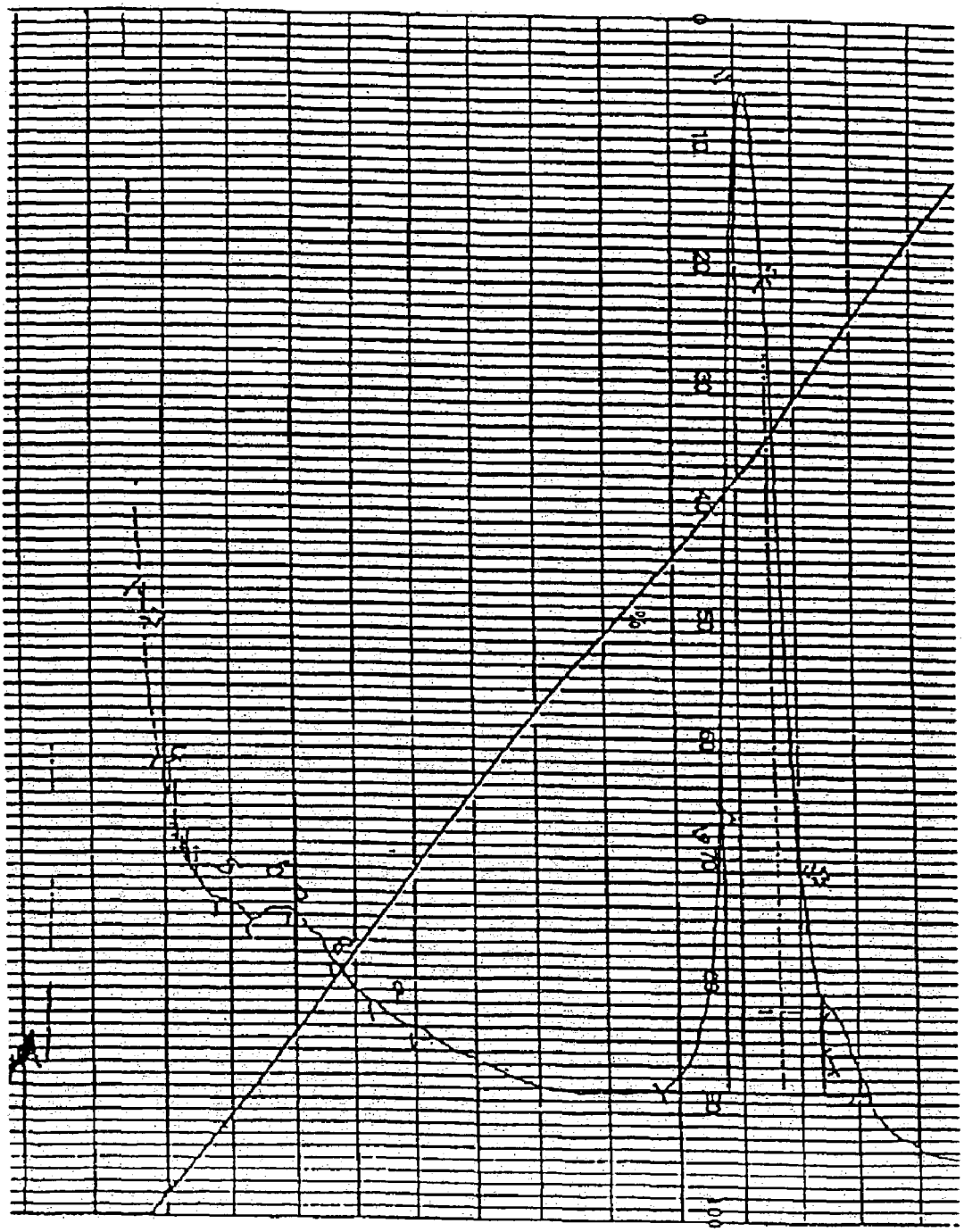
FIG. 3 shows a chromatogram of HIC fractionated culture supernatant of an *Aspergillus tubigensis* transformant with 62-fold increase of lipase 3.
Figure 4:
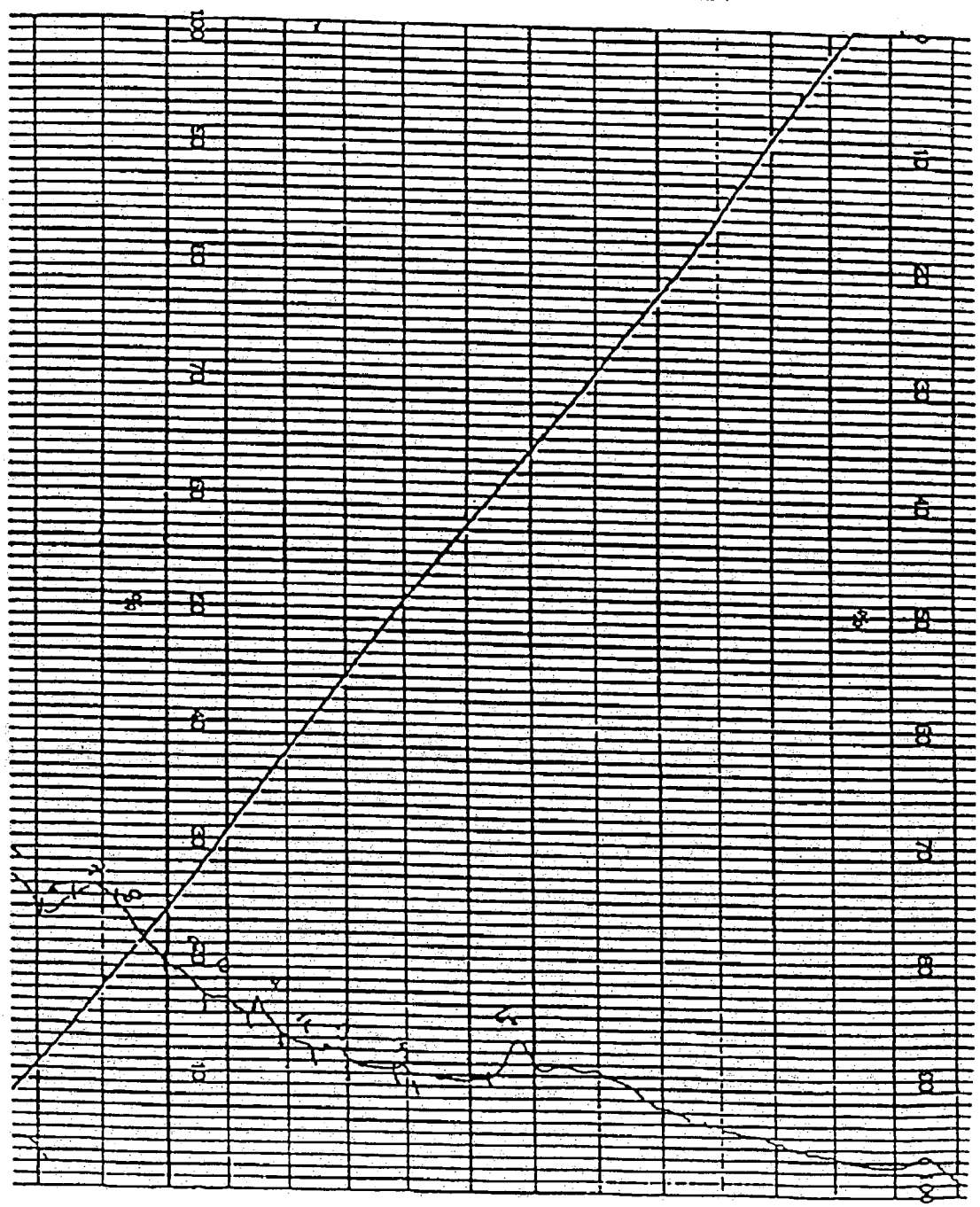
FIG. 4 shows a chromatogram of HIC fractionated culture supernatant of the untransformed *Aspergillus tubigensis* strain.

The cell-free culture supernatants from the five transformants were: desalted using NAP 5 columns (Pharmacia) and equilibrated in 1M ammonium sulfate (50 mM sodium acetate, pH 5.5). The desalted culture supernatants were fractionated by hydrophobic interaction chromatography (HIC) on a Biogel Phenyl-5 PW column (Biorad). Elution was done by a descending salt gradient of 1M to 0 M ammonium sulfate (20 mM sodium acetate, pH 5.5). A single discrete protein peak was observed after fractionation. The area of the protein peaks were calculated among the different transformants and compared with the untransformed strain. The best transformant showed a 62-fold increase in the amount of lipase after HIC fractionation. A chromatogram of the HIC fractionated culture supernatant of this transformant is shown in FIG. 3 and a similar chromatogram for the untransformed strain is shown in FIG. 4.

The fraction containing the transformed lipase was freeze-dried. The transformed lipase was carboxymethylated and subjected to N-terminal amino acid sequencing of the first 15 amino acids and it was found that the sequence of the recombinant lipase was exactly the same as the native lipase indicating correct signal sequence cleavage.

The different lipase fractions collected after HIC were separated on a 12% Tris-Glycine SDS gel-and silver staining revealed one protein band, confirming the homogeneity of the fractions. In addition, the crude extract showed a major lipase band as the only band that accumulated in the culture supernatant in very high amounts when the fungus was cultured in the olive oil-containing medium.

The recombinant lipase was analysed by matrix-assisted laser desorption ionisation (MALDI) by means of a time-of-flight (TOF) mass spectrometer as described hereinbefore. The molecular weight of the recombinant lipase was 32,237 Da.

Detection of N-linked oligosaccharides was achieved by digestion of the lipase with endo-β-N-acetyl-glucosamidase H from *Streptomyces* (Sigma). Digestion of recombinant lipase secreted into the growth medium altered the mobility of the band seen on SDS-PAGE which moved as a single band with a molecular mass of about 30 kDa.

Deglycosylated recombinant lipase generated by digestion with endoglycosidase and analysed directly by MALDI mass spectrometry gave a molecular weight of the polypeptide backbone of 29,325 Da.

C. Baking Experiments

EXAMPLE 8

Baking Experiments Using Lipase 3

8.1. Baking Procedures and Analytical Methods (i) Baking Procedure for Danish Toast Bread Flour (Danish reform flour) 2000 g, dry yeast 30 g, salt 30 g and water corresponding to 400 Brabender units+3%, was kneaded in a Hobart Mixer with hook for 2 min. at low speed and 10 min. at high speed. Dough temperature after kneading was 25° C. Resting time was 10 min. at 30° C. The dough was scaled 750 g per dough and rested again for 5 min at 33° C. and 85% RH. After moulding on a Glimik moulder, the dough were proofed in tins for 50 min at 33° C. and baked in a Wachtel oven for 40 min at 220° C. with steam injection for 16 sec. After cooling, the bread was scaled and the volume of the bread was measured by the rape seed displacement method. The specific volume is calculated by dividing the bread volume (ml) by the weight (g) of the bread.

The crumb was evaluated subjectively using a scale from 1 to 5 where 1=coarsely inhomogeneous and 5=nicely homogeneous.

Three breads baked in tins with lid were stored at 20° C. and used for firmness measurements and pore measurements by means of an Image Analyzer.

(ii) Baking Procedure for Danish Rolls

Flour (Danish reform) 1500 g, compressed yeast 90,g, sugar 24 g, salt 24 g and water corresponding to 400 Brabender units−2% were kneaded in a Hobart mixer with hook for 2 min. at low speed and 9 min at high speed. After kneading, the dough temperature was 26° C. The dough was scaled 1350 g. After resting for 10 min. at 30° C., the dough was moulded on a Fortuna moulder after which the dough was proofed for 45 min. at 34° C. and baked in a Bago oven for 18 min. at 220° C. with steam injection for 12 sec. After cooling, the rolls were scaled and the volume of the rolls was measured by the rape seed displacement method. Specific volume is calculated as described above.

(iii) Determination of Pore Homogeneity

The pore homogeneity of the bread was measured by means of an image analyzer composed of a standard CCD-video camera, a video digitiser and a personal computer with WinGrain software. For every bread, the results of pore diameter in mm and pore homogeneity were calculated as an average of measurements from 10 slices of bread. The pore homogeneity was expressed in % of pores that are larger than 0.5 times the average of pore diameter and smaller than 2 times the average diameter.

(iv) Determination of Firmness

The firmness of bread, expressed as $N/dm^2$, was measured by means of an Instron UTM model 4301 connected to a personal computer. The conditions for measurement of bread firmness were:

| Load Cell | Max. 100 N |
|---|---|
| Piston diameter | 50 mm |
| Cross head speed | 200 mm/min |
| Compression | 25% |
| Thickness of bread slice | 11 mm |

The result was an average of measurements on 10 bread slices for every bread.

(v) Determination of Gluten Index

Gluten index was measured by means of a Glutomatic 2200 from Perten Instruments (Sweden). Immediately after proofing, 15 g of dough was scaled and placed in the Glutomatic and washed with 500 ml 2% NaCl solution for 10 min. The washed dough was transferred to a Gluten Index Centrifuge 2015 and the two gluten fractions were scaled and the gluten index calculated according to the following equation:

Gluten index=(weight of gluten remaining on the sieve×100)/total-weight of gluten (vi) Extraction of Lipids from Dough 30 g of fully proofed dough was immediately frozen and freeze-dried. The freeze-dried dough was milled in a coffee mill and passed through a 235 μm screen. 4 g freeze-dried dough was scaled in a 50 ml centrifuge tube with screw lid and 20 ml water saturated n-butanol (WSB) was added. The centrifuge tube was placed in a water bath at a temperature of 100° C. for 10 min. after which the tubes were placed in a Rotamix and turned at 45 rpm for 20 min. at ambient temperature. The tubes were again placed in the water bath for 10 min. and turned on the Rotamix for another 30 min. at ambient temperature.

The tubes were centrifuged at 10,000×g for 5 min. 10 ml of the supernatant was pipetted into a vial and evaporated to dryness under nitrogen cover. This sample was used for HPLC analysis.

A similar sample was fractionated on a Bond Elut Si (Varian 1211-3036). The non-polar fraction was eluted with 10 ml cyclohexan:isopropanol:acetic acid (55:45:1) and evaporated to dryness. This sample was used for GLC analysis.

(vii) HPLC Analysis

Column: LiChrospher 100 DIOL 5 μm (Merck art. 16152) 250×4 mm with a water jacket of a temperature of 50° C.

Mobile phases:

A: heptan:isopropanol:n-butanol:tetrahydrofuran:isooctan: water (64.5:17.5:7:5:5:1)

B: isopropanol:n-butanol:tetrahydrofuran:isooctan:water (73:7:5:5:10)

The mobile phases contained 1 mmol trifluoroacetic acid per 1 mobile phase and were adjusted to pH 6.6 with ammonia.

Pump: Waters 510 equipped with a gradient controller.

| | Gradient: | | |
|---|---|---|---|
| Flow (ml/min) | Time (min) | A (%) | B (%) |
| 1.0 | 0 | 100 | 0 |
| 1.0 | 25 | 0 | 100 |
| 1.0 | 30 | 0 | 100 |
| 1.0 | 35 | 100 | 0 |
| 1.0 | 40 | 100 | 0 |

Detector: CUNOW DDL21 (evaporative light-scattering); temperature 100° C.; voltage: 600 volt; air flow: 6.0 l/min.

Injector: Hewlett Packard 1050; injection volume: 50 µl.

The samples for analysis were dissolved in 5 ml chloroform:methanol (75:25), sonicated for 10 min and filtered through a 0.45 µm filter.

(viii) GLC Analysis

Perkin Elmer 8420 Capillary Gas Chromatograph equipped with WCOT fused silica column 12.5 m×0.25 mm coated with 0.1 µm stationary phase of 5% phenyl-methyl-silicone (CP Sil 8 CB from Crompack).

Carrier: Helium
Injection: 1.5 µl with split
Detector: FID 385° C.

| | Oven program: | | | |
|---|---|---|---|---|
| | 1 | 2 | 3 | 4 |
| Oven temperature, ° C. | 80 | 200 | 240 | 360 |
| Isothermal time, min | 2 | 0 | 0 | 10 |
| Temperature rate, ° C./min | 20 | 10 | 12 | — |

Sample preparation: 50 mg non-polar fraction of wheat lipids was dissolved in 12 ml heptane:pyridine (2:1) containing 2 mg/ml heptadecane as internal standard. 500 µl of the solution was transferred to a crimp vial and 100 µl N-methyl-N-trimethylsilyl-trifluoracetamide was added. The mixture was allowed to react for 15 min at 90° C.

Calculation: Response factors for mono-, di- and triglycerides and free fatty acids were determined from reference mixtures of these components. Based on these response factors, the glycerides and the free fatty acids were calculated in wheat lipids.

8.2. Baking Experiments with Lipase 3 in Danish Toast Bread

The effect of adding lipase 3 to a dough for making Danish toast bread was evaluated. The enzyme was added as a freeze-dried preparation on maltodextrin together with the other ingredients. The results of the baking tests are shown in Tables 8.1 to 8.4.

TABLE 8.1

| | Lipase LUS/kg flour | | | |
|---|---|---|---|---|
| | 0 | 5,000 | 15,000 | 25,000 |
| Specific volume of bread | 4.43 | 4.43 | 4.22 | 4.37 |
| Firmness Day 1 | 35 | 33 | 32 | 30 |
| Firmness Day 7 | 90 | 90 | 85 | 73 |

TABLE 8.2

| | Lipase LUS/kg flour | | | |
|---|---|---|---|---|
| | 0 | 5,000 | 15,000 | 25,000 |
| Average diameter of the crumb pore, mm | 2.96 | 2.33 | 2.47 | 2.65 |
| Homogeneity of crumb pore, % | 64.9 | 73.8 | 66.0 | 67.1 |
| Porosity, % | 85.9 | 84.7 | 85.5 | 85.1 |
| Gluten index, % | 42 | 45.5 | 55 | 65 |

TABLE 8.3

| | Lipase LUS/kg flour | | | |
|---|---|---|---|---|
| | 0 | 5,000 | 15,000 | 25,000 |
| Fatty acids, % | 0.090 | 0.148 | 0.218 | 0.241 |
| Monoglycerides, % | 0.017 | 0.031 | 0.035 | 0.039 |
| Diglycerides, % | 0.020 | 0.036 | 0.040 | 0.045 |
| Triglycerides, % | 0.790 | 0.714 | 0.673 | 0.622 |

TABLE 8.4

| | Lipase LUS/kg flour | | | |
|---|---|---|---|---|
| | 0 | 5,000 | 15,000 | 25,000 |
| Monogalactosyl Diglyceride, % | 0.073 | 0.040 | 0.025 | 0.018 |
| Digalactosyl Diglyceride, % | 0.244 | 0.220 | 0.182 | 0.127 |
| Digalactosyl Monoglyceride, % | 0.008 | 0.022 | 0.044 | 0.054 |
| Phosphatidyl choline, % | 0.064 | 0.073 | 0.055 | 0.041 |
| Lysophosphatidyl choline, % | 0.164 | 0.182 | 0.171 | 0.165 |

By the addition of up to about 5,000 LUS/kg flour of the lipase no change in bread volume was observed, but at a higher dosage of lipase 3 there was a tendency to a small but not statistically significant decrease in volume (Table 8.1).

From the results in Table 8.2 it appears that lipase 3 improved the bread crumb homogeneity and that the average diameter of the crumb pores was reduced significantly. The gluten index also clearly correlated to the addition of lipase 3 as an indication of a more firm gluten caused by the modification of the wheat lipid components causing better dough stability and a more homogeneous bread pore structure. However, these modifications appeared to be optimal at the addition of 5,000 LUS/kg flour of lipase 3 whereas a higher dosage resulted in a too strong modification of the wheat gluten.

The results of the GLC and HPLC analyses (Table 8.3) clearly demonstrated that the triglycerides in the dough were hydrolysed. But more interestingly, there was also observed a modification of the glycolipids, monogalactosyl diglyceride and digalactosyl diglyceride. These components were converted to the more polar components monogalactosyl monoglyceride and digalactosyl monoglyceride. As digalactosyl monoglyceride is a more surface active component than digalactosyl diglyceride it is assumed that this component contributed to the observed improved crumb cell structure and homogeneity. It also appeared that phospholipids like phosphatidyl choline were only modified to a very small extent.

8.3. Baking Experiments with Lipase 3 in Danish Rolls

The effect of adding lipase 3 to a dough for making Danish rolls was evaluated. The enzyme was added as a freeze-dried preparation on maltodextrin together with the other ingredients. The results of the baking tests are shown in Tables 8.5 to 8.7.

TABLE 8.5

|  | Lipase 3 LUS/kg flour | | | |
|---|---|---|---|---|
|  | 0 | 10,000 | 20,000 | 30,000 |
| Specific volume of bread (45 min fermentation) | 6.86 | 7.04 | 6.35 | 6.36 |
| Specific volume of bread (65 min fermentation) | 8.30 | 8.59 | 8.23 | 8.04 |
| Subjective evaluation of crumb homogeneity | 3 | 5 | 4 | 4 |

TABLE 8.6

|  | Lipase 3 LUS/kg flour | | | |
|---|---|---|---|---|
|  | 0 | 10,000 | 20,000 | 30,000 |
| Free fatty acids, % | 0.060 | 0.126 | 0.173 | 0.211 |
| Monoglycerides, % | 0.028 | 0.050 | 0.054 | 0.063 |
| Diglycerides, % | 0.103 | 0.095 | 0.110 | 0.104 |
| Triglycerides, % | 0.705 | 0.561 | 0.472 | 0.436 |

TABLE 8.7

|  | Lipase 3 LUS/kg flour | | | |
|---|---|---|---|---|
|  | 0 | 5,000 | 15,000 | 25,000 |
| Digalactosyl Diglyceride, % | 0.204 | 0.187 | 0.154 | 0.110 |
| Digalactosyl Monoglyceride, % | 0.007 | 0.026 | 0.047 | 0.074 |
| Phosphatidyl choline, % | 0.077 | 0.078 | 0.077 | 0.063 |
| Lysophosphatidyl choline, % | 0.153 | 0.161 | 0.162 | 0.150 |

It is apparent from the results shown in Table 8.5 that the addition of lipase 3 does not significantly increase the volume of the rolls. Furthermore, lipase 3 was found to improve the homogeneity of the crumb.

The GLC and HPLC analyses of the wheat lipids, as shown in Tables 8.6 and 8.7, demonstrated the modification of these lipids.

EXAMPLE 9

Dough Improving Effect of Glycerol Oxidase and Lipase

The effect of glycerol oxidase and lipase (separately or in combination) on dough strength was studied in a dough prepared according to the AACC Method 54-10. The dough was subjected to extensiograph measurements (Barbender Extensiograph EXEK/6) also according to AACC Method 54-10 with and with out the addition of glycerol oxidase from *Aspergillus japonicus* combined with lipase from *Aspergillus oryzae* (GRINDAMYL™ EXEL 16, Bakery Enzyme, Danisco Ingredients). The dough with out addition of enzymes served as a control.

The principle of the above method is that the dough after forming is subjected to a load-extension test after resting at 30° C. for 45, 90 and 135 minutes, respectively, using an extensigraph capable of recording a load-extension curve (extensigram) which is an indication of the doughs resistance to physical deformation when stretched. From this curve, the resistance to extension, B (height of curve) and the extensibility, C (total length of curve) can be calculated. The B/C ratio (D) is an indication of the baking strength of the flour dough. The results of the experiment are summarized in Table 9.1 below.

TABLE 9.1

Extensigraph measurements of dough supplemented with glycerol oxidase and lipase

| Sample (per kg flour) | Resting time (min) | B-value | C-value | D = B/C |
|---|---|---|---|---|
| Control | 45 | 220 | 192 | 1.15 |
| 500 LUS lipase | 45 | 225 | 190 | 1.18 |
| 1000 U glycerol oxidase | 45 | 300 | 195 | 1.54 |
| 500 LUS lipase + 1000 U Glycerol oxidase | 45 | 350 | 198 | 1.77 |
| Control | 90 | 240 | 196 | 1.22 |
| 500 LUS lipase | 90 | 245 | 195 | 1.16 |
| 1000 U Glycerol oxidase | 90 | 330 | 190 | 1.74 |
| 500 LUS lipase + 1000 U Glycerol oxidase | 90 | 380 | 192 | 1.98 |
| Control | 135 | 260 | 188 | 1.38 |
| 500 LUS lipase | 135 | 265 | 190 | 1.39 |
| 1000 U Glycerol oxidase | 135 | 380 | 188 | 2.02 |
| 500 LUS lipase + 1000 U Glycerol oxidase | 135 | 410 | 190 | 2.15 |

When the results from the above experiments are compared with regard to the differences between the control dough and the glycerol oxidase supplemented dough it appears that glycerol oxidase clearly has a strengthening effect. The B/C ratio was increased by 34%, 43% and 46% after 45, 90 and 135 minutes of resting time respectively.

The addition of lipase only did not have any effect on the B/C ratio.

However, when supplementing the dough with a combination of glycerol oxidase and lipase, a further increase in the B/C ratio was seen as compared to bread prepared from dough supplemented with glycerol oxidase only. The B/C ratio was increased by 54%, 62% and 56% after 45, 90 and 135 minutes respectively. This clearly indicates that the combined use of these two enzymes in the preparation of bread products has an enhancing effect on the baking strength.

EXAMPLE 10

Improvement of the Specific Volume of Bread Prepared from Dough Supplemented with Glycerol Oxidase and Lipase The effect of using glycerol oxidase and lipase (separately or in combination) on the specific bread volume and the crumb homogeneity was tested in a baking procedure for Danish rolls with a dough prepared as described in example 8. Glycerol oxidase from *Aspergillus japonicus* and lipase 3 from *Aspergillus tubigensis* was added to the dough in different amounts. Dough without the addition of enzymes served as control. The fully proofed dough was baked at 220° C. for 18 minutes with 12 seconds steam in a Bago-oven. After cooling the rolls were weighed and the volume of the rolls were measured by the rape seed displacement method. The specific bread volume was determined as the volume of the bread (ml) divided by the weight of the bread (g). The crumb homogeneity was evaluated subjectively on a scale from 1 to 7, where 1=course inhomogeneous and 7=nice homogeneous. The results from this experiment are summarized in Table 10.1 below.

TABLE 10.1

Specific volume and crumb homogeneity in bread supplemented with lipase and glycerol

| Sample (per kg flour) | Specific volume (ml/g) | Crumb homogeneity |
|---|---|---|
| Control | 5.45 | 1 |
| 1,000 U glycerol oxidase | 6.75 | 2 |
| 10,000 LUS lipase | 5.65 | 4 |
| 10,000 LUS lipase + 1,000 U glycerol oxidase | 7.25 | 7 |

As can be seen in the above Table 10.1, the use of glycerol oxidase in the preparing of bread, significantly increased the bread volume (24%) as compared to bread prepared from a similar dough not supplemented with this enzyme. Addition of glycerol oxidase did not improve the crumb homogeneity significantly.

The use of lipase in the preparing of bread did not increase the specific volume of the bread, however a highly increased pore homogeneity was observed.

The combined use of glycerol oxidase and lipase increased the specific volume of the bread with 33% as compared to bread prepared from a similar dough not supplemented with any of the two enzymes.

In addition, the crumb homogeneity was highly improved by the combined use of lipase and glycerol oxidase as compared to the control bread and the breads prepared from dough supplemented with lipase and glycerol oxidase respectively.

This clearly indicates that the combination of lipase and glycerol oxidase in the preparation of bread has a synergistic effect and significantly enhances the shape and appearance of the finished bread product.

EXAMPLE 11

Hydrolysis of Triglycerides and Formation of Glycerol in Dough Supplemented with Lipase In order to study the hydrolysis of triglycerides and the formation of glycerol in a proofed dough supplemented with lipase, a dough for Danish rolls was prepared in the same manner as described in example 8. Different amounts of lipase (GRINDAMYL™ EXEL 16) was added to the dough, and the total lipid from the fully proofed dough was extracted and analyzed by gas chromatography as described above.

TABLE 11.1

Triglycerides and glycerol in a dough as a function of lipase addition

| Lipase addition (GRINDAMYL ™ EXEL 16) (LUS per kg flour) | Glycerol (%) | Triglycerides (%) |
|---|---|---|
| 0 | 2.2 | 7.88 |
| 500 | 2.2 | 6.22 |
| 1,250 | 2.4 | 5.99 |
| 2,500 | 2.8 | 5.37 |
| 3,750 | 2.9 | 5.47 |
| 5,000 | 3.0 | 5.55 |
| 7,500 | 3.1 | 5.03 |
| 10,000 | 3.0 | 4.39 |

From the above experiment it is clear that the addition of lipase to a dough has a hydrolyzing effect on the triglycerides present in the dough, which is seen as a decrease in the triglyceride content as function of the increased lipase addition. The resulting level of glycerol increases as a function of the lipase addition.

These results suggests, that the improvement of the B/C ratios and the specific bread volume in bread prepared from dough supplemented with both glycerol oxidase and lipase, as was seen in example 9 and 10, could be due to that lipase addition to a dough is generating glycerol which further can act as substrate for glycerol oxidase.

SUMMARY PARAGRAPHS

The present invention is defined in the claims and the accompanying description.

For convenience other aspects of the present invention are presented herein by way of numbered paragraphs.

1. A method of improving the rheological properties of a flour dough and the quality of the finished product made from the dough, comprising adding to the dough 10 to 10,000 units of a glycerol oxidase per kg of flour.
2. A method according to paragraph 1 wherein the glycerol oxidase is derived from an organism selected from the group consisting of a bacterial species, a fungal species, a yeast species, an animal cell and a plant cell.
3. A method according to paragraph 2 wherein the fungal species is selected from the group consisting of an *Aspergillus* species, a *Neurospora* species and a *Penicillium*, species.
4. A method according to paragraph 1 wherein the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough not containing glycerol oxidase.
5. A method according to paragraph 1 wherein the finished product is selected from the group consisting of a bread product, a noodle product and an alimentary paste product.
6. A method according to paragraph 1 where at least one further enzyme is added to the dough ingredients, dough additives or the dough.
7. A method according to paragraph 6 wherein the further enzyme is selected from the group consisting of a cellulase, a hemicellulase, a starch degrading enzyme, an oxidoreductase, a lipase and a protease.
8. A method of improving the rheological properties of a flour dough and the quality of the finished product made from the dough, comprising adding to the dough a glycerol oxidase and a lipase.

9. A method according to paragraph 8 wherein the amount of glycerol oxidase is in the range of 10 to 10,000 units per kg flour.

b 10. A method according to paragraph 8 wherein the glycerol oxidase is derived from an organism selected from the group consisting of a bacterial species, a fungal species, a yeast species, an animal cell and a plant cell.

11. A method according to paragraph 10 wherein the fungal species is selected from the group consisting of an Aspergillus species, a Neurospora species and a Penicillium species.

12. A method according to paragraph 8 wherein the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough not containing glycerol oxidase.

13. A method according to paragraph 8 wherein the finished product is selected from the group consisting of a bread product, a noodle product and an alimentary paste product.

14. A method according to paragraph 8 where at least one further enzyme is added to the dough ingredients, dough additives or the dough.

15. A method according to paragraph 14 wherein the further enzyme is selected from the group consisting of a cellulase, a hemicellulase, a starch degrading enzyme, an oxidoreductase, and a protease.

16. A method according to paragraph 8 wherein the amount of lipase is in the range of 10 to 100,000 LUS per kg of flour.

17. A method according to paragraph 8 wherein the lipase is derived from an organism selected from the group consisting of a bacterial species, a fungal species, a yeast species, an animal cell and a plant cell.

18. A method according to paragraph 17 wherein the lipase is derived from an *Aspergillus* species.

19. A method according to paragraph 18 wherein the *Aspergillus* species is selected from the group consisting of *A. tubigensis, A. oryzae* and *A. niger.*

20. A method according to paragraph 8 wherein at least 10% of the galactosyl diglycerides normally present in a flour dough is hydrolysed to the corresponding galactosyl monoglycerides.

21. A dough improving composition comprising a glycerol oxidase and at least one further dough ingredient or dough additive.

22. A composition according to paragraph 21 wherein the further dough additive is'selected from the group consisting of a substrate for glycerol oxidase and a lipase.

23. A composition according to paragraph 22 which is a premixture useful for preparing a baked product or in making a noodle product or an alimentary paste product.

24. A composition according to paragraph 21 which comprises an additive selected from the group consisting of an emulsifying agent and a hydrocolloid.

25. A composition according to paragraph 24 wherein the hydrocolloid is selected from the group consisting of an alginate, a carrageenan, a pectin and a vegetable gum.

26. A composition according to paragraph 21 wherein the amount of glycerol oxidase is in the range of 10 to 10,000 units per kg flour.

27. A composition according to paragraph 21 or 26, comprising as the further dough additive a lipase in an amount which is in the range of 10 to 100,000 LUS per kg flour.

28. Use of a glycerol oxidase for improving the rheological properties of a flour dough and the quality of the finished product made from the dough.

29. Use according to paragraph 28 wherein the improvement of the theological properties include that the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough not containing glycerol oxidase.

30. Use of a glycerol oxidase and a lipase in combination for improving the theological properties of a flour dough and the quality of the finished product made from the dough.

31. Use according to paragraph 30 wherein the improvement of the theological properties of the dough include that the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough that does not contain glycerol oxidase.

32. Use according to paragraph 30 wherein the improvement of the quality of the finished product made from the dough is that the average pore diameter of the crumb of the bread made from the dough is reduced by at least 10%, relative to a bread which is made from a bread dough without addition of the lipase.

33. Use according to paragraph 30 wherein the improvement of the quality of the finished product made from the dough is that the pore homogeneity of the crumb of the bread made from the dough is increased by at least 5%, relative to a bread which is made from a bread dough without addition of the lipase.

34. Use according to paragraph 30 or 31 wherein the improvement of the rheological characteristics of the dough includes that the gluten index in the dough is increased by at least 5%, relative to a dough without addition of a lipase, the gluten index is determined by means of a Glutomatic 2200 apparatus.

We claim:

1. A method of preparing a dough comprising adding to dough ingredients an enzyme that hydrolyzes compounds including a triglyceride, a glycolipid, and a phospholipid.

2. A method for preparing bread comprising preparing a dough comprising adding to dough ingredients an enzyme that hydrolyzes compounds including a triglyceride, a glycolipid, and a phospholipid; and baking the dough.

3. A dough prepared according to the method of claim 1.

4. In a dough wherein the improvement comprises the dough including an enzyme that hydrolyzes compounds including a triglyceride, a glycolipid, and a phospholipid.

5. The method of any one of claims 1-2 wherein the dough ingredients include an additional enzyme.

6. The method of claim 5, wherein the additional enzyme is a starch degrading enzyme.

7. The method of claim 6, wherein the additional enzyme is an amylase.

8. A dough produced by the method of claim 5.

9. The method of any one of claims 1-2 wherein the dough ingredients include an emulsifier.

10. A dough prepared according to the method of claim 9.

11. The dough of claim 4 wherein the dough ingredients include an additional enzyme.

12. The dough of claim 11, wherein the additional enzyme is a starch degrading enzyme.

13. The dough of claim 12, wherein the additional enzyme is an amylase.

14. The dough of claim 4, wherein the dough ingredients include an emulsifier.

15. The method of claim 9, wherein the emulsifier is selected from monoglycerides, diacetyl tartaric acid esters of mono- and diglycerides of fatty acids, and lecithins.

* * * * *

UNITED STATES PATENT AND TRADEMARK OFFICE
CERTIFICATE OF CORRECTION

PATENT NO.          : 7,371,423 B2                           Page 1 of 1
APPLICATION NO.  : 10/462527
DATED                   : May 13, 2008
INVENTOR(S)         : Jorn Borch Søe et al.

It is certified that error appears in the above-identified patent and that said Letters Patent is hereby corrected as shown below:

Title Page; should read;

ON THE FACE OF THE PATENT:

(75)          Inventors:          Jorn Borch Søe, Mundelstrup (DK);
                                           Charlotte Horsmans Poulsen, Bradband (DK);
                                           Preben Rasmussen, Kirke Hyllinge (DK);
                                           Susan Mampusti Madrid, <u>Vedbaek</u> (DK);
                                           Masoud R. Zargahi, Århus C. (DK)

Signed and Sealed this

Second Day of September, 2008

JON W. DUDAS
*Director of the United States Patent and Trademark Office*

SEQUENCE LISTING

<160> NUMBER OF SEQ ID NOS: 22

<210> SEQ ID NO 1
<211> LENGTH: 25
<212> TYPE: PRT
<213> ORGANISM: Aspergillus tubingensis
<220> FEATURE:

```
<221> NAME/KEY: MISC_FEATURE
<222> LOCATION: (22)..(22)
<223> OTHER INFORMATION: "Xaa" can be any amino acid

<400> SEQUENCE: 1

Ser Val Ser Thr Ser Thr Leu Asp Glu Leu Gln Leu Phe Ala Gln Trp
1               5                   10                  15

Ser Ala Ala Ala Tyr Xaa Ser Asn Asn
            20              25

<210> SEQ ID NO 2
<211> LENGTH: 7
<212> TYPE: PRT
<213> ORGANISM: Aspergillus tubingensis

<400> SEQUENCE: 2

Val His Thr Gly Phe Trp Lys
1               5

<210> SEQ ID NO 3
<211> LENGTH: 14
<212> TYPE: PRT
<213> ORGANISM: Aspergillus tubingensis

<400> SEQUENCE: 3

Ala Trp Glu Ser Ala Ala Asp Glu Leu Thr Ser Lys Ile Lys
1               5                   10

<210> SEQ ID NO 4
<211> LENGTH: 20
<212> TYPE: DNA
<213> ORGANISM: Artificial Sequence
<220> FEATURE:
<223> OTHER INFORMATION: PCR primer used for PCR amplification of a
      fragment of the lipase gene
<220> FEATURE:
<221> NAME/KEY: misc_feature
<222> LOCATION: (9)..(9)
<223> OTHER INFORMATION: "n" can be a or t/u or g or c
<220> FEATURE:
<221> NAME/KEY: misc_feature
<222> LOCATION: (12)..(12)
<223> OTHER INFORMATION: "n" can be a or t/u or g or c
<220> FEATURE:
<221> NAME/KEY: misc_feature
<222> LOCATION: (18)..(18)
<223> OTHER INFORMATION: "n" can be a or t/u or g or c

<400> SEQUENCE: 4
ttccaraanc cngtrtgnac                                              20

<210> SEQ ID NO 5
<211> LENGTH: 18
<212> TYPE: DNA
<213> ORGANISM: Artificial Sequence
<220> FEATURE:
<223> OTHER INFORMATION: PCR primer used for PCR amplification of a
      fragment of the lipase gene
<220> FEATURE:
<221> NAME/KEY: misc_feature
<222> LOCATION: (6)..(6)
<223> OTHER INFORMATION: "n" can be a or t/u or g or c
<220> FEATURE:
<221> NAME/KEY: misc_feature
<222> LOCATION: (12)..(12)
<223> OTHER INFORMATION: "n" can be a or t/u or g or c

<400> SEQUENCE: 5
carytnttyg cncartgg                                                18
```

<210> SEQ ID NO 6
<211> LENGTH: 17
<212> TYPE: DNA
<213> ORGANISM: Artificial Sequence
<220> FEATURE:
<223> OTHER INFORMATION: PCR primer used for PCR amplification of a fragment of the lipase gene

<400> SEQUENCE: 6
gcvgchswyt cccavgc                                                17

<210> SEQ ID NO 7
<211> LENGTH: 317
<212> TYPE: DNA
<213> ORGANISM: Aspergillus tubingensis

<400> SEQUENCE: 7
cagttgttcg cgcaatggtc tgccgcagct tattgctcga ataatatcga ctcgaaagav     60
tccaacttga catgcacggc caacgcctgt ccatcagtcg aggaggccag taccacgatg    120
ctgctggagt tcgacctgta tgtcactcag atcgcagaca tagagcacag ctaattgaac    180
aggacgaacg acttttggag gcacagccgg tttcctggcc gcggacaaca ccaacaagcg    240
gctcgtggtc gccttccggg gaagcagcac gattgagaac tggattgcta atcytgactt    300
catcctggra gataacg                                                  317

<210> SEQ ID NO 8
<211> LENGTH: 1045
<212> TYPE: DNA
<213> ORGANISM: Aspergillus tubingensis

<400> SEQUENCE: 8
atgttctctg gacggtttgg agtgcttttg acagcgcttg ctgcgctggg tgctgccgcg     60
ccggcaccgc ttgctgtgcg gagtaggtgt gcccgatgtg agatggttgg atagcactga    120
tgaagggtga ataggtgtct cgacttccac gttggatgag ttgcaattgt tcgcgcaatg    180
gtctgccgca gcttattgct cgaataatat cgactcgaaa gactccaact tgacatgcac    240
ggccaacgcc tgtccatcag tcgaggaggc cagtaccacg atgctgctgg agttcgacct    300
gtatgtcact cagatcgcag acatagagca cagctaattt gaacaggacg aacgactttg    360
gaggcacagc cggtttcctg gccgcggaca caccaacaa gcggctcgtg gtcgccttcc    420
ggggaagcag cacgattgag aactggattg ctaatcttga cttcatcctg gaagataacg    480
acgacctctg caccggctgc aaggtccata ctggtttctg gaaggcatgg gagtccgctg    540
ccgacgaact gacgagcaag atcaagtctg cgatgagcac gtattcgggc tatacccctat    600 acttcaccgg gcacagtttg ggcggcgcat tggctacgct gggagcgaca gttctgcgaa    660 atgacgggata tagcgttgag ctggtgagtc cttcacaaag gtgatggagc gacaatcggg    720
aacagacagt caatagtaca cctatggatg tcctcgaatc ggaaactatg cgctggctga    780
gcatatcacc agtcagggat ctggggccaa cttccgtgtt acacacttga acgacatcgt    840
cccccgggtg ccacccatgg actttggatt cagtcagcca agtccggaat actggatcac    900
cagtggcaat ggagccagtg tcacggcgtc ggatatcgaa gtcatcgagg gaatcaattc    960
aacggcggga aatgcaggcg aagcaacggt gagcgttgtg gctcacttgt ggtactttt    1020 tgcgatttcc gagtgcctgc tataa                                       1045

<210> SEQ ID NO 9
<211> LENGTH: 297
<212> TYPE: PRT
<213> ORGANISM: Aspergillus tubingensis

<400> SEQUENCE: 9

Met Phe Ser Gly Arg Phe Gly Val Leu Leu Thr Ala Leu Ala Ala Leu
1               5                   10                  15

Gly Ala Ala Pro Ala Pro Leu Ala Val Arg Ser Val Ser Thr Ser
            20                  25                  30

Thr Leu Asp Glu Leu Gln Leu Phe Ala Gln Trp Ser Ala Ala Ala Tyr
        35                  40                  45

Cys Ser Asn Asn Ile Asp Ser Lys Asp Ser Asn Leu Thr Cys Thr Ala
    50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Glu Asn Trp Ile Ala Asn Leu Asp Phe Ile Leu Glu Asp Asn Asp
        115                 120                 125

Asp Leu Cys Thr Gly Cys Lys Val His Thr Gly Phe Trp Lys Ala Trp
    130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Ile Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                245                 250                 255

Val Thr Ala Ser Asp Ile Glu Val Ile Glu Gly Ile Asn Ser Thr Ala
            260                 265                 270

Gly Asn Ala Gly Glu Ala Thr Val Ser Val Ala His Leu Trp Tyr
        275                 280                 285

Phe Phe Ala Ile Ser Glu Cys Leu Leu
    290                 295

<210> SEQ ID NO 10
<211> LENGTH: 392
<212> TYPE: PRT
<213> ORGANISM: Rhizopus delamar

<400> SEQUENCE: 10

Met Val Ser Phe Ile Ser Ile Ser Gln Gly Val Ser Leu Cys Leu Leu
1               5                   10                  15

Val Ser Ser Met Met Leu Gly Ser Ser Ala Val Pro Val Ser Gly Lys
            20                  25                  30

Ser Gly Ser Ser Asn Thr Ala Val Ser Ala Ser Asp Asn Ala Ala Leu

```
                35                  40                  45
Pro Pro Leu Ile Ser Ser Arg Cys Ala Pro Ser Asn Lys Gly Ser
50                  55                  60

Lys Ser Asp Leu Gln Ala Glu Pro Tyr Asn Met Gln Lys Asn Thr Glu
65                  70                  75                  80

Trp Tyr Glu Ser His Gly Gly Asn Leu Thr Ser Ile Gly Lys Arg Asp
                85                  90                  95

Asp Asn Leu Val Gly Gly Met Thr Leu Asp Leu Pro Ser Asp Ala Pro
                100                 105                 110

Pro Ile Ser Leu Ser Ser Thr Asn Ser Ala Ser Asp Gly Gly Lys
                115                 120                 125

Val Val Ala Ala Thr Thr Ala Gln Ile Gln Glu Phe Thr Lys Tyr Ala
130                 135                 140

Gly Ile Ala Ala Thr Ala Tyr Cys Arg Ser Val Val Pro Gly Asn Lys
145                 150                 155                 160

Trp Asp Cys Val Gln Cys Gln Lys Trp Val Pro Asp Gly Lys Ile Ile
                165                 170                 175

Thr Thr Phe Thr Ser Leu Leu Ser Asp Thr Asn Gly Tyr Val Leu Arg
                180                 185                 190

Ser Asp Lys Gln Lys Thr Ile Tyr Leu Val Phe Arg Gly Thr Asn Ser
                195                 200                 205

Phe Arg Ser Ala Ile Thr Asp Ile Val Phe Asn Phe Ser Asp Tyr Lys
210                 215                 220

Pro Val Lys Gly Ala Lys Val His Ala Gly Phe Leu Ser Ser Tyr Glu
225                 230                 235                 240

Gln Val Val Asn Asp Tyr Phe Pro Val Val Gln Glu Gln Leu Thr Ala
                245                 250                 255

His Pro Thr Tyr Lys Val Ile Val Thr Gly His Ser Leu Gly Gly Ala
                260                 265                 270

Gln Ala Leu Leu Ala Gly Met Asp Leu Tyr Gln Arg Glu Pro Arg Leu
                275                 280                 285

Ser Pro Lys Asn Leu Ser Ile Phe Thr Val Gly Gly Pro Arg Val Gly
290                 295                 300

Asn Pro Thr Phe Ala Tyr Tyr Val Glu Ser Thr Gly Ile Pro Phe Gln
305                 310                 315                 320

Arg Thr Val His Lys Arg Asp Ile Val Pro His Val Pro Pro Gln Ser
                325                 330                 335

Phe Gly Phe Leu His Pro Gly Val Glu Ser Trp Ile Lys Ser Gly Thr
                340                 345                 350

Ser Asn Val Gln Ile Cys Thr Ser Glu Ile Glu Thr Lys Asp Cys Ser
                355                 360                 365

Asn Ser Ile Val Pro Phe Thr Ser Ile Leu Asp His Leu Ser Tyr Phe
                370                 375                 380

Asp Ile Asn Glu Gly Ser Cys Leu
385                 390

<210> SEQ ID NO 11
<211> LENGTH: 363
<212> TYPE: PRT
<213> ORGANISM: Rhizomucor miehei

<400> SEQUENCE: 11

Met Val Leu Lys Gln Arg Ala Asn Tyr Leu Gly Phe Leu Ile Val Phe
1               5                   10                  15
```

-continued

```
Phe Thr Ala Phe Leu Val Glu Ala Val Pro Ile Lys Arg Gln Ser Asn
             20                  25                  30

Ser Thr Val Asp Ser Leu Pro Pro Leu Ile Pro Ser Arg Thr Ser Ala
         35                  40                  45

Pro Ser Ser Ser Pro Ser Thr Thr Asp Pro Glu Ala Pro Ala Met Ser
 50                  55                  60

Arg Asn Gly Pro Leu Pro Ser Asp Val Glu Thr Lys Tyr Gly Met Ala
 65                  70                  75                  80

Leu Asn Ala Thr Ser Tyr Pro Asp Ser Val Val Gln Ala Met Ser Ile
                 85                  90                  95

Asp Gly Gly Ile Arg Ala Ala Thr Ser Gln Glu Ile Asn Glu Leu Thr
            100                 105                 110

Tyr Tyr Thr Thr Leu Ser Ala Asn Ser Tyr Cys Arg Thr Val Ile Pro
        115                 120                 125

Gly Ala Thr Trp Asp Cys Ile His Cys Asp Ala Thr Glu Asp Leu Lys
    130                 135                 140

Ile Ile Lys Thr Trp Ser Thr Leu Ile Tyr Asp Thr Asn Ala Met Val
145                 150                 155                 160

Ala Arg Gly Asp Ser Glu Lys Thr Ile Tyr Ile Val Phe Arg Gly Ser
                165                 170                 175

Ser Ser Ile Arg Asn Trp Ile Ala Asp Leu Thr Phe Val Pro Val Ser
            180                 185                 190

Tyr Pro Pro Val Ser Gly Thr Lys Val His Lys Gly Phe Leu Asp Ser
        195                 200                 205

Tyr Gly Glu Val Gln Asn Glu Leu Val Ala Thr Val Leu Asp Gln Phe
    210                 215                 220

Lys Gln Tyr Pro Ser Tyr Lys Val Ala Val Thr Gly His Ser Leu Gly
225                 230                 235                 240

Gly Ala Thr Ala Leu Leu Cys Ala Leu Asp Leu Tyr Gln Arg Glu Glu
                245                 250                 255

Gly Leu Ser Ser Ser Asn Leu Phe Leu Tyr Thr Gln Gly Gln Pro Arg
            260                 265                 270

Val Gly Asp Pro Ala Phe Ala Asn Tyr Val Val Ser Thr Gly Ile Pro
        275                 280                 285

Tyr Arg Arg Thr Val Asn Glu Arg Asp Ile Val Pro His Leu Pro Pro
    290                 295                 300

Ala Ala Phe Gly Phe Leu His Ala Gly Glu Glu Tyr Trp Ile Thr Asp
305                 310                 315                 320

Asn Ser Pro Glu Thr Val Gln Val Cys Thr Ser Asp Leu Glu Thr Ser
                325                 330                 335

Asp Cys Ser Asn Ser Ile Val Pro Phe Thr Ser Val Leu Asp His Leu
            340                 345                 350

Ser Tyr Phe Gly Ile Asn Thr Gly Leu Cys Thr
        355                 360
```

<210> SEQ ID NO 12
<211> LENGTH: 305
<212> TYPE: PRT
<213> ORGANISM: Penicillium camemberti

<400> SEQUENCE: 12

```
Met Arg Leu Ser Phe Phe Thr Ala Leu Ser Ala Val Ala Ser Leu Gly
1               5                   10                  15

Tyr Ala Leu Pro Gly Lys Leu Gln Ser Arg Asp Val Ser Thr Ser Glu
             20                  25                  30
```

```
Leu Asp Gln Phe Glu Phe Trp Val Gln Tyr Ala Ala Ala Ser Tyr Tyr
         35                  40                  45

Glu Ala Asp Tyr Thr Ala Gln Val Gly Asp Lys Leu Ser Cys Ser Lys
 50                  55                  60

Gly Asn Cys Pro Glu Val Glu Ala Thr Gly Ala Thr Val Ser Tyr Asp
 65                  70                  75                  80

Phe Ser Asp Ser Thr Ile Thr Asp Thr Ala Gly Tyr Ile Ala Val Asp
                 85                  90                  95

His Thr Asn Ser Ala Val Val Leu Ala Phe Arg Gly Ser Tyr Ser Val
            100                 105                 110

Arg Asn Trp Val Ala Asp Ala Thr Phe Val His Thr Asn Pro Gly Leu
        115                 120                 125

Cys Asp Gly Cys Leu Ala Glu Leu Gly Phe Trp Ser Ser Trp Lys Leu
    130                 135                 140

Val Arg Asp Asp Ile Ile Lys Glu Leu Lys Glu Val Val Ala Gln Asn
145                 150                 155                 160

Pro Asn Tyr Glu Leu Val Val Gly His Ser Leu Gly Ala Ala Val
                165                 170                 175

Ala Thr Leu Ala Ala Thr Asp Leu Arg Gly Lys Gly Tyr Pro Ser Ala
                180                 185                 190

Lys Leu Tyr Ala Tyr Ala Ser Pro Arg Val Gly Asn Ala Ala Leu Ala
            195                 200                 205

Lys Tyr Ile Thr Ala Gln Gly Asn Asn Phe Arg Phe Thr His Thr Asn
        210                 215                 220

Asp Pro Val Pro Lys Leu Pro Leu Leu Ser Met Gly Tyr Val His Val
225                 230                 235                 240

Ser Pro Glu Tyr Trp Ile Thr Ser Pro Asn Asn Ala Thr Val Ser Thr
                245                 250                 255

Ser Asp Ile Lys Val Ile Asp Gly Asp Val Ser Phe Asp Gly Asn Thr
            260                 265                 270

Gly Thr Gly Leu Pro Leu Leu Thr Asp Phe Glu Ala His Ile Trp Tyr
        275                 280                 285

Phe Val Gln Val Asp Ala Gly Lys Gly Pro Gly Leu Pro Phe Lys Arg
    290                 295                 300

Val
305

<210> SEQ ID NO 13
<211> LENGTH: 334
<212> TYPE: DNA
<213> ORGANISM: Aspergillus tubingensis
<220> FEATURE:
<221> NAME/KEY: misc_feature
<222> LOCATION: (10)..(10)
<223> OTHER INFORMATION: "n" can be a or g or c or t/u
<220> FEATURE:
<221> NAME/KEY: CDS
<222> LOCATION: (18)..(329)
<223> OTHER INFORMATION:

<400> SEQUENCE: 13
tacccggggn tccgatt cag ttg ttc gcg caa tgg tct gcc gca gct tat      50
                    Gln Leu Phe Ala Gln Trp Ser Ala Ala Ala Tyr
                     1               5                  10 tgc tcg aat aat atc gac tcg aaa gav tcc aac ttg aca tgc acg gcc    98
Cys Ser Asn Asn Ile Asp Ser Lys Xaa Ser Asn Leu Thr Cys Thr Ala
         15                  20                  25
```

```
aac gcc tgt cca tca gtc gag gag gcc agt acc acg atg ctg ctg gag      146
Asn Ala Cys Pro Ser Val Glu Glu Ala Ser Thr Thr Met Leu Leu Glu
         30                  35                  40 ttc gac ctg tat gtc act cag atc gca gac ata gag cac agc taa ttg      194
Phe Asp Leu Tyr Val Thr Gln Ile Ala Asp Ile Glu His Ser     Leu
 45                  50                  55 aac agg acg aac gac ttt tgg agg cac agc cgg ttt cct ggc cgc gga      242
Asn Arg Thr Asn Asp Phe Trp Arg His Ser Arg Phe Pro Gly Arg Gly
         60                  65                  70 caa cac caa caa gcg gct cgt ggt cgc ctt ccg ggg aag cag cac gat      290
Gln His Gln Gln Ala Ala Arg Gly Arg Leu Pro Gly Lys Gln His Asp
 75                  80                  85                  90 tga gaa ctg gat tgc taa tcy tga ctt cat cct ggr aga taacg            334
    Glu Leu Asp Cys     Xaa     Leu His Pro Xaa Arg
                         95                  100
```

<210> SEQ ID NO 14
<211> LENGTH: 57
<212> TYPE: PRT
<213> ORGANISM: Aspergillus tubingensis
<220> FEATURE:
<221> NAME/KEY: misc_feature
<222> LOCATION: (20)..(20)
<223> OTHER INFORMATION: The 'Xaa' at location 20 stands for Glu, or
      Asp.
<220> FEATURE:
<221> NAME/KEY: misc_feature
<222> LOCATION: (10)..(10)
<223> OTHER INFORMATION: "n" can be a or g or c or t/u

<400> SEQUENCE: 14

Gln Leu Phe Ala Gln Trp Ser Ala Ala Ala Tyr Cys Ser Asn Asn Ile
 1               5                  10                  15

Asp Ser Lys Xaa Ser Asn Leu Thr Cys Thr Ala Asn Ala Cys Pro Ser
                 20                  25                  30

Val Glu Glu Ala Ser Thr Thr Met Leu Leu Glu Phe Asp Leu Tyr Val
             35                  40                  45

Thr Gln Ile Ala Asp Ile Glu His Ser
         50                  55

<210> SEQ ID NO 15
<211> LENGTH: 33
<212> TYPE: PRT
<213> ORGANISM: Aspergillus tubingensis
<220> FEATURE:
<221> NAME/KEY: misc_feature
<222> LOCATION: (10)..(10)
<223> OTHER INFORMATION: "n" can be a or g or c or t/u

<400> SEQUENCE: 15

Leu Asn Arg Thr Asn Asp Phe Trp Arg His Ser Arg Phe Pro Gly Arg
 1               5                  10                  15

Gly Gln His Gln Gln Ala Ala Arg Gly Arg Leu Pro Gly Lys Gln His
                 20                  25                  30

Asp

<210> SEQ ID NO 16
<211> LENGTH: 4
<212> TYPE: PRT
<213> ORGANISM: Aspergillus tubingensis
<220> FEATURE:
<221> NAME/KEY: misc_feature
<222> LOCATION: (10)..(10)
<223> OTHER INFORMATION: "n" can be a or g or c or t/u -continued

```
<400> SEQUENCE: 16

Glu Leu Asp Cys
1

<210> SEQ ID NO 17
<211> LENGTH: 5
<212> TYPE: PRT
<213> ORGANISM: Aspergillus tubingensis
<220> FEATURE:
<221> NAME/KEY: misc_feature
<222> LOCATION: (4)..(4)
<223> OTHER INFORMATION: The 'Xaa' at location 4 stands for Gly.
<220> FEATURE:
<221> NAME/KEY: misc_feature
<222> LOCATION: (10)..(10)
<223> OTHER INFORMATION: "n" can be a or g or c or t/u

<400> SEQUENCE: 17

Leu His Pro Xaa Arg
1               5

<210> SEQ ID NO 18
<211> LENGTH: 1833
<212> TYPE: DNA
<213> ORGANISM: Aspergillus tubingensis
<220> FEATURE:
<221> NAME/KEY: misc_feature
<222> LOCATION: (3)..(3)
<223> OTHER INFORMATION: n can be a or g or c or t/u
<220> FEATURE:
<221> NAME/KEY: exon
<222> LOCATION: (372)..(453)
<223> OTHER INFORMATION:
<220> FEATURE:
<221> NAME/KEY: exon
<222> LOCATION: (506)..(672)
<223> OTHER INFORMATION:
<220> FEATURE:
<221> NAME/KEY: exon
<222> LOCATION: (719)..(1054)
<223> OTHER INFORMATION:
<220> FEATURE:
<221> NAME/KEY: exon
<222> LOCATION: (1108)..(1413)
<223> OTHER INFORMATION:

<400> SEQUENCE: 18
ccndttaatc ccccaccggg gttcccgctc ccggatggag atggggccaa aactggcaac      60
ccccagttgc gcaacggaac aaccgccgac ccggaacaaa ggatgcggat gaggagatac    120
ggtgcctgat tgcatggctg gcttcatctg ctatcgtgac agtgctcttt gggtgaatat    180
tgttgtctga cttacccccgc ttcttgcttt ttcccccctg aggccctgat ggggaatcgc   240
ggtgggtaat atgatatggg tataaaaggg agatcggagg tgcagttgga ttgaggcagt    300
gtgtgtgtgt gcattgcaga agcccgttgg tcgcaaggtt ttggtcgcct cgattgtttg    360
tataccgcaa g atg ttc tct gga cgg ttt gga gtg ctt ttg aca gcg ctt     410
            Met Phe Ser Gly Arg Phe Gly Val Leu Leu Thr Ala Leu
              1               5                  10 gct gcg ctg ggt gct gcc gcg ccg gca ccg ctt gct gtg cgg a             453
Ala Ala Leu Gly Ala Ala Ala Pro Ala Pro Leu Ala Val Arg
    15                  20                  25 gtaggtgtgc ccgatgtgag atggttggat agcactgatg aagggtgaat ag gt  gtc     510
                                                        Ser Val tcg act tcc acg ttg gat gag ttg caa ttg ttc gcg caa tgg tct gcc      558
Ser Thr Ser Thr Leu Asp Glu Leu Gln Leu Phe Ala Gln Trp Ser Ala
30                  35                  40                  45
```

```
                                                           -continued gca gct tat tgc tcg aat aat atc gac tcg aaa gac tcc aac ttg aca       606
Ala Ala Tyr Cys Ser Asn Asn Ile Asp Ser Lys Asp Ser Asn Leu Thr
             50                  55                  60 tgc acg gcc aac gcc tgt cca tca gtc gag gag gcc agt acc acg atg       654
Cys Thr Ala Asn Ala Cys Pro Ser Val Glu Glu Ala Ser Thr Thr Met
 65                  70                  75 ctg ctg gag ttc gac ctg tatgtcactc agatcgcaga catagagcac              702
Leu Leu Glu Phe Asp Leu
         80 agctaatttg aacagg acg aac gac ttt gga ggc aca gcc ggt ttc ctg gcc     754
               Thr Asn Asp Phe Gly Gly Thr Ala Gly Phe Leu Ala
                    85                  90                  95 gcg gac aac acc aac aag cgg ctc gtg gtc gcc ttc cgg gga agc agc       802
Ala Asp Asn Thr Asn Lys Arg Leu Val Val Ala Phe Arg Gly Ser Ser
                100                 105                 110 acg att gag aac tgg att gct aat ctt gac ttc atc ctg gaa gat aac       850
Thr Ile Glu Asn Trp Ile Ala Asn Leu Asp Phe Ile Leu Glu Asp Asn
                115                 120                 125 gac gac ctc tgc acc ggc tgc aag gtc cat act ggt ttc tgg aag gca       898
Asp Asp Leu Cys Thr Gly Cys Lys Val His Thr Gly Phe Trp Lys Ala
        130                 135                 140 tgg gag tcc gct gcc gac gaa ctg acg agc aag atc aag tct gcg atg       946
Trp Glu Ser Ala Ala Asp Glu Leu Thr Ser Lys Ile Lys Ser Ala Met
    145                 150                 155 agc acg tat tcg ggc tat acc cta tac ttc acc ggg cac agt ttg ggc       994
Ser Thr Tyr Ser Gly Tyr Thr Leu Tyr Phe Thr Gly His Ser Leu Gly
160                 165                 170                 175 ggc gca ttg gct acg ctg gga gcg aca gtt ctg cga aat gac gga tat      1042
Gly Ala Leu Ala Thr Leu Gly Ala Thr Val Leu Arg Asn Asp Gly Tyr
                180                 185                 190 agc gtt gag ctg gtgagtcctt cacaaaggtg atggagcgac aatcgggaac          1094
Ser Val Glu Leu
            195 agacagtcaa tag tac acc tat gga tgt cct cga atc gga aac tat gcg       1143
               Tyr Thr Tyr Gly Cys Pro Arg Ile Gly Asn Tyr Ala
                                200                 205 ctg gct gag cat atc acc agt cag gga tct ggg gcc aac ttc cgt gtt      1191
Leu Ala Glu His Ile Thr Ser Gln Gly Ser Gly Ala Asn Phe Arg Val
        210                 215                 220 aca cac ttg aac gac atc gtc ccc cgg gtg cca ccc atg gac ttt gga      1239
Thr His Leu Asn Asp Ile Val Pro Arg Val Pro Pro Met Asp Phe Gly
    225                 230                 235 ttc agt cag cca agt ccg gaa tac tgg atc acc agt ggc aat gga gcc      1287
Phe Ser Gln Pro Ser Pro Glu Tyr Trp Ile Thr Ser Gly Asn Gly Ala
240                 245                 250                 255 agt gtc acg gcg tcg gat atc gaa gtc atc gag gga atc aat tca acg      1335
Ser Val Thr Ala Ser Asp Ile Glu Val Ile Glu Gly Ile Asn Ser Thr
                260                 265                 270 gcg gga aat gca ggc gaa gca acg gtg agc gtt gtg gct cac ttg tgg      1383
Ala Gly Asn Ala Gly Glu Ala Thr Val Ser Val Val Ala His Leu Trp
        275                 280                 285 tac ttt ttt gcg att tcc gag tgc ctg cta taactagacc gactgtcaga        1433
Tyr Phe Phe Ala Ile Ser Glu Cys Leu Leu
    290                 295 ttagtggacg ggagaagtgt acataagtaa ttagtatata atcagagcaa cccagtggtg    1493
gtgatggtgg tgaaagaaga aacacattga gttcccatta cgkagcagwt aaagcacktk    1553
kggaggcgct ggttcctcca cttggcagtt ggcggccatc aatcatcttt cctctcctta    1613
ctttcgtcca ccacaactcc catcctgcca gctgtcgcat ccccgggttg caacaactat    1673
```

```
cgcctccggg gcctccgtgg ttctcctata ttattccatc cgacggccga cgtttcaccc    1733
tcaacctgcg ccgccgcaaa atctccccga gtcggtcaac tccctcgaac cgccgcccgc    1793
atcgacctca cgaccccgac cgtctgygat ygtccaaccg                           1833
```

<210> SEQ ID NO 19
<211> LENGTH: 14
<212> TYPE: PRT
<213> ORGANISM: Artificial Sequence
<220> FEATURE:
<223> OTHER INFORMATION: selected lipase 3 peptide

<400> SEQUENCE: 19

Ala Trp Glu Ser Ala Ala Asp Glu Leu Thr Ser Lys Ile Lys
1               5                   10

<210> SEQ ID NO 20
<211> LENGTH: 25
<212> TYPE: PRT
<213> ORGANISM: Artificial Sequence
<220> FEATURE:
<223> OTHER INFORMATION: N terminal lipase 3 peptide
<220> FEATURE:
<221> NAME/KEY: MISC_FEATURE
<222> LOCATION: (22)..(22)
<223> OTHER INFORMATION: "x" can be any amino acid

<400> SEQUENCE: 20

Ser Val Ser Thr Ser Thr Leu Asp Glu Leu Gln Leu Phe Ala Gln Trp
1               5                   10                  15

Ser Ala Ala Ala Tyr Xaa Ser Asn Asn
            20                  25

<210> SEQ ID NO 21
<211> LENGTH: 6
<212> TYPE: PRT
<213> ORGANISM: Artificial Sequence
<220> FEATURE:
<223> OTHER INFORMATION: portion of N-terminal lipase peptide used in
      synthesizing PCR primer C036

<400> SEQUENCE: 21

Gln Leu Phe Ala Gln Trp
1               5

<210> SEQ ID NO 22
<211> LENGTH: 6
<212> TYPE: PRT
<213> ORGANISM: Artificial Sequence
<220> FEATURE:
<223> OTHER INFORMATION: portion of N-terminal lipase peptide used in
      synthesizing PCR primer C037

<400> SEQUENCE: 22

Ala Trp Glu Ser Ala Ala
1               5